United States Patent
Greinacher et al.

(10) Patent No.: US 8,084,216 B2
(45) Date of Patent: Dec. 27, 2011

(54) SCREENING METHODS FOR TRANSFUSION RELATED ACUTE LUNG INJURY (TRALI)

(75) Inventors: Andreas Greinacher, Suederholz (DE); Jan Wesche, Greifswald (DE); Juergen Bux, Hagen (DE); Angelika Reil, Hagen (DE)

(73) Assignees: Ernst-Moritz-Arndt-Universität Greifswald, Greifswald (DE); DRK Blutspendedienst West GmbH, Hagen (DE)

( * ) Notice: Subject to any disclaimer, the term of this patent is extended or adjusted under 35 U.S.C. 154(b) by 0 days.

(21) Appl. No.: 12/553,487

(22) Filed: Sep. 3, 2009

(65) Prior Publication Data

US 2010/0055706 A1    Mar. 4, 2010

(30) Foreign Application Priority Data

Sep. 4, 2008   (DE) .................. 10 2008 045 696

(51) Int. Cl.
- *G01N 33/53* (2006.01)
- *A61K 38/00* (2006.01)
- *C07K 14/00* (2006.01)

(52) U.S. Cl. .................. 435/7.1; 530/300; 530/350

(58) Field of Classification Search .................. None
See application file for complete search history.

(56) References Cited

U.S. PATENT DOCUMENTS

| | | |
|---|---|---|
| 6,943,235 B1 | 9/2005 | Afar et al. |
| 7,220,823 B2 | 5/2007 | Afar et al. |
| 7,227,008 B2 | 6/2007 | Afar et al. |
| 7,303,895 B1 | 12/2007 | O'Regan et al. |
| 7,303,985 B2 | 12/2007 | Deng et al. |
| 7,306,796 B2 | 12/2007 | Afar et al. |
| 7,368,531 B2 | 5/2008 | Rosen et al. |
| 7,411,051 B2 | 8/2008 | Rosen et al. |
| 2003/0219777 A1 | 11/2003 | Shang et al. |
| 2007/0015209 A1 | 1/2007 | Carey et al. |
| 2007/0083334 A1 | 4/2007 | Mintz et al. |

FOREIGN PATENT DOCUMENTS

| | | |
|---|---|---|
| EP | 1074617 | 2/2001 |
| WO | WO-00/58473 | 10/2000 |
| WO | WO-01/32704 | 5/2001 |
| WO | WO-2004/041152 | 5/2004 |

OTHER PUBLICATIONS

Davoren et al., TRALI due to granulocyte-agglutinating human neutrophil antigen-3a (5b) alloantibodies in donor plasma: A report of 2 fatalities. *Transfusion*, 43: 641-5 (2003).

Genbank Accession No: NP-065161, solute carrier family 44, member 2 isoform 1 [*Homo sapiens*], Feb. 15, 2009.

Nair et al. Identification and characterization of choline transporter-like protein 2, an inner ear glycoprotein of 68 and 72 kDa that is the target of antibody-induced hearing loss. J. Neurosci. 24(7): 1772-1779 (2004).

O'Regan et al., An electric lobe suppressor for a yeast choline transport mutation belongs to a new family of transporter-like proteins. *Proc. Natl. Acad. Sci. USA*, 97: 1835-40 (2000).

Silliman et al., Donor antibodies to HNA-3a implicated in TRALI reactions prime neutrophils and causes PMN-mediated damage to human pulmonary microvascular endothelial cells in a two-event in vitro model. *Blood*, 109: 1752-5 (2007).

SNP Cluster Report, rs2288904, <http://www.ncbi.nlm.nih.gov/projects/SNP>.

Yu et al., Large-scale concatenation cDNA sequencing. *Genome Res.* 7(4): 353-8 (1997).

International Search Report and Written Opinion of the International Searching Authority, European Patent Office, PCT/EP2009/006386, dated Nov. 30, 2009.

*Primary Examiner* — Michail Belyavskyi

(74) *Attorney, Agent, or Firm* — Marshall, Gerstein & Borun LLP

(57) ABSTRACT

The invention relates to the discovery that HNA-3a and HNA-3b are antigens within a polypeptide sequence that is highly similar to the CTL2 amino acid sequence. This invention provides methods and kits for screening for HNA-3a and HNA-3b specific antibodies, HNA-3a and HNA-3b polypeptides and HNA-3a and HNA-3b nucleic acids in a sample of a biological tissue intended for transplantation.

14 Claims, No Drawings

SEQUENCE LISTING

<160> NUMBER OF SEQ ID NOS: 53

<210> SEQ ID NO 1
<211> LENGTH: 706
<212> TYPE: PRT
<213> ORGANISM: Homo sapiens
<220> FEATURE:
<221> NAME/KEY: MISC_FEATURE
<223> OTHER INFORMATION: HNA-3a protein

<400> SEQUENCE: 1

```
Met Gly Asp Glu Arg Pro His Tyr Tyr Gly Lys His Gly Thr Pro Gln
1               5                   10                  15

Lys Tyr Asp Pro Thr Phe Lys Gly Pro Ile Tyr Asn Arg Gly Cys Thr
            20                  25                  30

Asp Ile Ile Cys Cys Val Phe Leu Leu Leu Ala Ile Val Gly Tyr Val
        35                  40                  45

Ala Val Gly Ile Ile Ala Trp Thr His Gly Asp Pro Arg Lys Val Ile
    50                  55                  60

Tyr Pro Thr Asp Ser Arg Gly Glu Phe Cys Gly Gln Lys Gly Thr Lys
65                  70                  75                  80

Asn Glu Asn Lys Pro Tyr Leu Phe Tyr Phe Asn Ile Val Lys Cys Ala
                85                  90                  95

Ser Pro Leu Val Leu Leu Glu Phe Gln Cys Pro Thr Pro Gln Ile Cys
            100                 105                 110

Val Glu Lys Cys Pro Asp Arg Tyr Leu Thr Tyr Leu Asn Ala Arg Ser
        115                 120                 125

Ser Arg Asp Phe Glu Tyr Tyr Lys Gln Phe Cys Val Pro Gly Phe Lys
    130                 135                 140

Asn Asn Lys Gly Val Ala Glu Val Leu Arg Asp Gly Asp Cys Pro Ala
145                 150                 155                 160

Val Leu Ile Pro Ser Lys Pro Leu Ala Arg Arg Cys Phe Pro Ala Ile
                165                 170                 175

His Ala Tyr Lys Gly Val Leu Met Val Gly Asn Glu Thr Thr Tyr Glu
            180                 185                 190

Asp Gly His Gly Ser Arg Lys Asn Ile Thr Asp Leu Val Glu Gly Ala
        195                 200                 205

Lys Lys Ala Asn Gly Val Leu Glu Ala Arg Gln Leu Ala Met Arg Ile
    210                 215                 220

Phe Glu Asp Tyr Thr Val Ser Trp Tyr Trp Ile Ile Gly Leu Val
225                 230                 235                 240

Ile Ala Met Ala Met Ser Leu Leu Phe Ile Ile Leu Arg Phe Leu
                245                 250                 255

Ala Gly Ile Met Val Trp Val Met Ile Ile Met Val Ile Leu Val Leu
            260                 265                 270

Gly Tyr Gly Ile Phe His Cys Tyr Met Glu Tyr Ser Arg Leu Arg Gly
        275                 280                 285

Glu Ala Gly Ser Asp Val Ser Leu Val Asp Leu Gly Phe Gln Thr Asp
    290                 295                 300

Phe Arg Val Tyr Leu His Leu Arg Gln Thr Trp Leu Ala Phe Met Ile
305                 310                 315                 320

Ile Leu Ser Ile Leu Glu Val Ile Ile Leu Leu Leu Ile Phe Leu
                325                 330                 335

Arg Lys Arg Ile Leu Ile Ala Ile Ala Leu Ile Lys Glu Ala Ser Arg
            340                 345                 350

Ala Val Gly Tyr Val Met Cys Ser Leu Leu Tyr Pro Leu Val Thr Phe
        355                 360                 365

Phe Leu Leu Cys Leu Cys Ile Ala Tyr Trp Ala Ser Thr Ala Val Phe
    370                 375                 380

Leu Ser Thr Ser Asn Glu Ala Val Tyr Lys Ile Phe Asp Asp Ser Pro
385                 390                 395                 400

Cys Pro Phe Thr Ala Lys Thr Cys Asn Pro Glu Thr Phe Pro Ser Ser
                405                 410                 415

Asn Glu Ser Arg Gln Cys Pro Asn Ala Arg Cys Gln Phe Ala Phe Tyr
            420                 425                 430
```

```
Gly Gly Glu Ser Gly Tyr His Arg Ala Leu Leu Gly Leu Gln Ile Phe
            435                 440                 445

Asn Ala Phe Met Phe Phe Trp Leu Ala Asn Phe Val Leu Ala Leu Gly
        450                 455                 460

Gln Val Thr Leu Ala Gly Ala Phe Ala Ser Tyr Tyr Trp Ala Leu Arg
465                 470                 475                 480

Lys Pro Asp Asp Leu Pro Ala Phe Pro Leu Phe Ser Ala Phe Gly Arg
                485                 490                 495

Ala Leu Arg Tyr His Thr Gly Ser Leu Ala Phe Gly Ala Leu Ile Leu
                500                 505                 510

Ala Ile Val Gln Ile Ile Arg Val Ile Leu Glu Tyr Leu Asp Gln Arg
            515                 520                 525

Leu Lys Ala Ala Glu Asn Lys Phe Ala Lys Cys Leu Met Thr Cys Leu
        530                 535                 540

Lys Cys Cys Phe Trp Cys Leu Glu Lys Phe Ile Lys Phe Leu Asn Arg
545                 550                 555                 560

Asn Ala Tyr Ile Met Ile Ala Ile Tyr Gly Thr Asn Phe Cys Thr Ser
                565                 570                 575

Ala Arg Asn Ala Phe Phe Leu Leu Met Arg Asn Ile Ile Arg Val Ala
                580                 585                 590

Val Leu Asp Lys Val Thr Asp Phe Leu Phe Leu Leu Gly Lys Leu Leu
            595                 600                 605

Ile Val Gly Ser Val Gly Ile Leu Ala Phe Phe Phe Thr His Arg
        610                 615                 620

Ile Arg Ile Val Gln Asp Thr Ala Pro Pro Leu Asn Tyr Tyr Trp Val
625                 630                 635                 640

Pro Ile Leu Thr Val Ile Val Gly Ser Tyr Leu Ile Ala His Gly Phe
                645                 650                 655

Phe Ser Val Tyr Gly Met Cys Val Asp Thr Leu Phe Leu Cys Phe Leu
                660                 665                 670

Glu Asp Leu Glu Arg Asn Asp Gly Ser Ala Glu Arg Pro Tyr Phe Met
            675                 680                 685

Ser Ser Thr Leu Lys Lys Leu Leu Asn Lys Thr Asn Lys Ala Ala
        690                 695                 700

Glu Ser
705

<210> SEQ ID NO 2
<211> LENGTH: 706
<212> TYPE: PRT
<213> ORGANISM: Homo sapiens
<220> FEATURE:
<221> NAME/KEY: MISC_FEATURE
<223> OTHER INFORMATION: HNA-3b protein

<400> SEQUENCE: 2

Met Gly Asp Glu Arg Pro His Tyr Tyr Gly Lys His Gly Thr Pro Gln
1               5                   10                  15

Lys Tyr Asp Pro Thr Phe Lys Gly Pro Ile Tyr Asn Arg Gly Cys Thr
            20                  25                  30

Asp Ile Ile Cys Cys Val Phe Leu Leu Leu Ala Ile Val Gly Tyr Val
        35                  40                  45

Ala Val Gly Ile Ile Ala Trp Thr His Gly Asp Pro Arg Lys Val Ile
    50                  55                  60

Tyr Pro Thr Asp Ser Arg Gly Glu Phe Cys Gly Gln Lys Gly Thr Lys
65                  70                  75                  80
```

-continued

```
Asn Glu Asn Lys Pro Tyr Leu Phe Tyr Phe Asn Ile Val Lys Cys Ala
                 85                  90                  95
Ser Pro Leu Val Leu Leu Glu Phe Gln Cys Pro Thr Pro Gln Ile Cys
            100                 105                 110
Val Glu Lys Cys Pro Asp Arg Tyr Leu Thr Tyr Leu Asn Ala Arg Ser
        115                 120                 125
Ser Arg Asp Phe Glu Tyr Tyr Lys Gln Phe Cys Val Pro Gly Phe Lys
130                 135                 140
Asn Asn Lys Gly Val Ala Glu Val Leu Gln Asp Gly Asp Cys Pro Ala
145                 150                 155                 160
Val Leu Ile Pro Ser Lys Pro Leu Ala Arg Arg Cys Phe Pro Ala Ile
                165                 170                 175
His Ala Tyr Lys Gly Val Leu Met Val Gly Asn Glu Thr Thr Tyr Glu
            180                 185                 190
Asp Gly His Gly Ser Arg Lys Asn Ile Thr Asp Leu Val Glu Gly Ala
        195                 200                 205
Lys Lys Ala Asn Gly Val Leu Glu Ala Arg Gln Leu Ala Met Arg Ile
210                 215                 220
Phe Glu Asp Tyr Thr Val Ser Trp Tyr Trp Ile Ile Gly Leu Val
225                 230                 235                 240
Ile Ala Met Ala Met Ser Leu Leu Phe Ile Ile Leu Leu Arg Phe Leu
                245                 250                 255
Ala Gly Ile Met Val Trp Val Met Ile Ile Met Val Ile Leu Val Leu
            260                 265                 270
Gly Tyr Gly Ile Phe His Cys Tyr Met Glu Tyr Ser Arg Leu Arg Gly
        275                 280                 285
Glu Ala Gly Ser Asp Val Ser Leu Val Asp Leu Gly Phe Gln Thr Asp
290                 295                 300
Phe Arg Val Tyr Leu His Leu Arg Gln Thr Trp Leu Ala Phe Met Ile
305                 310                 315                 320
Ile Leu Ser Ile Leu Glu Val Ile Ile Leu Leu Ile Phe Leu
                325                 330                 335
Arg Lys Arg Ile Leu Ile Ala Ile Ala Leu Ile Lys Glu Ala Ser Arg
            340                 345                 350
Ala Val Gly Tyr Val Met Cys Ser Leu Leu Tyr Pro Leu Val Thr Phe
        355                 360                 365
Phe Leu Leu Cys Leu Cys Ile Ala Tyr Trp Ala Ser Thr Ala Val Phe
370                 375                 380
Leu Ser Thr Ser Asn Glu Ala Val Tyr Lys Ile Phe Asp Asp Ser Pro
385                 390                 395                 400
Cys Pro Phe Thr Ala Lys Thr Cys Asn Pro Glu Thr Phe Pro Ser Ser
                405                 410                 415
Asn Glu Ser Arg Gln Cys Pro Asn Ala Arg Cys Gln Phe Ala Phe Tyr
            420                 425                 430
Gly Gly Glu Ser Gly Tyr His Arg Ala Leu Leu Gly Leu Gln Ile Phe
        435                 440                 445
Asn Ala Phe Met Phe Phe Trp Leu Ala Asn Phe Val Leu Ala Leu Gly
450                 455                 460
Gln Val Thr Leu Ala Gly Ala Phe Ala Ser Tyr Tyr Trp Ala Leu Arg
465                 470                 475                 480
Lys Pro Asp Asp Leu Pro Ala Phe Pro Leu Phe Ser Ala Phe Gly Arg
                485                 490                 495
Ala Leu Arg Tyr His Thr Gly Ser Leu Ala Phe Gly Ala Leu Ile Leu
```

```
                500             505             510
Ala Ile Val Gln Ile Ile Arg Val Ile Leu Glu Tyr Leu Asp Gln Arg
            515                 520                 525
Leu Lys Ala Ala Glu Asn Lys Phe Ala Lys Cys Leu Met Thr Cys Leu
        530                 535                 540
Lys Cys Cys Phe Trp Cys Leu Glu Lys Phe Ile Lys Phe Leu Asn Arg
545                 550                 555                 560
Asn Ala Tyr Ile Met Ile Ala Ile Tyr Gly Thr Asn Phe Cys Thr Ser
                565                 570                 575
Ala Arg Asn Ala Phe Phe Leu Leu Met Arg Asn Ile Ile Arg Val Ala
            580                 585                 590
Val Leu Asp Lys Val Thr Asp Phe Leu Phe Leu Gly Lys Leu Leu
        595                 600                 605
Ile Val Gly Ser Val Gly Ile Leu Ala Phe Phe Phe Thr His Arg
        610                 615                 620
Ile Arg Ile Val Gln Asp Thr Ala Pro Pro Leu Asn Tyr Tyr Trp Val
625                 630                 635                 640
Pro Ile Leu Thr Val Ile Val Gly Ser Tyr Leu Ile Ala His Gly Phe
                645                 650                 655
Phe Ser Val Tyr Gly Met Cys Val Asp Thr Leu Phe Leu Cys Phe Leu
                660                 665                 670
Glu Asp Leu Glu Arg Asn Asp Gly Ser Ala Glu Arg Pro Tyr Phe Met
            675                 680                 685
Ser Ser Thr Leu Lys Lys Leu Leu Asn Lys Thr Asn Lys Lys Ala Ala
        690                 695                 700
Glu Ser
705

<210> SEQ ID NO 3
<211> LENGTH: 2121
<212> TYPE: DNA
<213> ORGANISM: Homo sapiens
<220> FEATURE:
<221> NAME/KEY: misc_feature
<223> OTHER INFORMATION: HNA-3a DNA

<400> SEQUENCE: 3 atggggacg agcggcccca ctactacggg aaacacggaa cgccacagaa gtatgatccc    60
actttcaaag gacccattta caatagggc tgcacggata tcatatgctg tgtgttcctg   120
ctcctggcca ttgtgggcta cgtggctgta ggcatcatag cctggactca tgagacccct   180
cgaaaggtga tctaccccac tgatagccgg ggcgagttct gcgggcagaa gggcacaaaa   240
aacgagaaca aacccatcct gttttatttc aacattgtga atgtgccag cccctggtt    300 ctgctggaat ccaatgtcc cactccccag atctgcgtgg aaaaatgccc cgaccgctac   360
ctcacgtacc tgaatgctcg cagctcccgg gactttgagt actataagca gttctgtgtt   420
cctggcttca gaacaataa aggagtggct gaggtgcttc gagatggtga ctgccctgct   480
gtcctcatcc ccagcaaacc cttggcccgg agatgcttcc ccgctatcca cgcctacaag   540
ggtgtcctga tggtgggcaa tgagacgacc tatgaggatg gcatggctc ccggaaaaac   600 atcacagacc tggtgggagg cgccaagaaa gccaatggag tcctagaggc gcggcaactc   660
gccatgcgca tatttgaaga ttacaccgtc tcttggtact ggattatcat aggcctggtc   720
attgccatgg cgatgagcct cctgttcatc atcctgcttc gcttcctggc tggtattatg   780
gtctgggtga tgatcatcat ggtgattctg gtgctgggct acggaatatt tcactgctac   840
```

| atggagtact | cccgactgcg | tggtgaggcc | ggctctgatg | tctctttggt | ggacctcggc | 900 |
| tttcagacgg | atttccgggt | gtacctgcac | ttacggcaga | cctggttggc | ctttatgatc | 960 |
| attctgagta | tccttgaagt | cattatcatc | ttgctgctca | tctttctccg | gaagagaatt | 1020 |
| ctcatcgcga | ttgcactcat | caaagaagcc | agcagggctg | tgggatacgt | catgtgctcc | 1080 |
| ttgctctacc | cactggtcac | cttcttcttg | ctgtgcctct | gcatcgccta | ctgggccagc | 1140 |
| actgctgtct | tcctgtccac | ttccaacgaa | gcggtctata | agatctttga | tgacagcccc | 1200 |
| tgcccattta | ctgcgaaaac | ctgcaaccca | gagaccttcc | cctcctccaa | tgagtcccgc | 1260 |
| caatgcccca | atgcccgttg | ccagttcgcc | ttctacggtg | gtgagtcggg | ctaccaccgg | 1320 |
| gccctgctgg | gcctgcagat | cttcaatgcc | ttcatgttct | tctggttggc | caacttcgtg | 1380 |
| ctggcgctgg | ccaggtcac | gctggccggg | gcctttgcct | cctactactg | ggccctgcgc | 1440 |
| aagccggacg | acctgccggc | cttcccgctc | ttctctgcct | ttggccgggc | gctcaggtac | 1500 |
| cacacaggct | ccctggcctt | tggcgcgctc | atcctggcca | ttgtgcagat | catccgtgtg | 1560 |
| atactcgagt | acctggatca | gcggctgaaa | gctgcagaga | acaagtttgc | caagtgcctc | 1620 |
| atgacctgtc | tcaaatgctg | cttctggtgc | ctggagaagt | tcatcaaatt | ccttaatagg | 1680 |
| aatgcctaca | tcatgattgc | catctacggc | accaatttct | gcacctcggc | caggaatgcc | 1740 |
| ttcttcctgc | tcatgagaaa | catcatcaga | gtggctgtcc | tggataaagt | tactgacttc | 1800 |
| ctcttcctgt | tgggcaaact | tctgatcgtt | ggtagtgtgg | ggatcctggc | tttcttcttc | 1860 |
| ttcacccacc | gtatcaggat | cgtgcaggat | acagcaccac | ccctcaatta | ttactgggtt | 1920 |
| cctatactga | cggtgatcgt | tggctcctac | ttgattgcac | acggtttctt | cagcgtctat | 1980 |
| ggcatgtgtg | tggacacgct | gttcctctgc | ttcttggagg | acctggagag | gaatgacggc | 2040 |
| tcggccgaga | ggccttactt | catgtcttcc | accctcaaga | aacccttgaa | caagaccaac | 2100 |
| aagaaggcag | cggagtcctg | a | | | | 2121 |

```
<210> SEQ ID NO 4
<211> LENGTH: 2121
<212> TYPE: DNA
<213> ORGANISM: Homo sapiens
<220> FEATURE:
<221> NAME/KEY: misc_feature
<223> OTHER INFORMATION: HNA-3b DNA

<400> SEQUENCE: 4
```

| atgggggacg | agcggcccca | ctactacggg | aaacacggaa | cgccacagaa | gtatgatccc | 60 |
| actttcaaag | gacccattta | caataggggc | tgcacggata | tcatatgctg | tgtgttcctg | 120 |
| ctcctggcca | ttgtgggcta | cgtggctgta | ggcatcatag | cctggactca | tggagaccct | 180 |
| cgaaaggtga | tctaccccac | tgatagccgg | ggcgagttct | gcgggcagaa | gggcacaaaa | 240 |
| aacgagaaca | aaccctatct | gttttatttc | aacattgtga | atgtgccag | cccctggtt | 300 |
| ctgctggaat | ccaatgtcc | cactccccag | atctgcgtgg | aaaaatgccc | cgaccgctac | 360 |
| ctcacgtacc | tgaatgctcg | cagctcccgg | gactttgagt | actataagca | gttctgtgtt | 420 |
| cctggcttca | agaacaataa | aggagtggct | gaggtgcttc | aagatggtga | ctgccctgct | 480 |
| gtcctcatcc | ccagcaaacc | cttggccggg | agatgcttcc | ccgctatcca | cgcctacaag | 540 |
| ggtgtcctga | tggtgggcaa | tgagacgacc | tatgaggatg | gcatggctc | ccggaaaaac | 600 |
| atcacagacc | tggtgagggg | cgccaagaaa | gccaatggag | tcctagaggc | gcggcaactc | 660 |
| gccatgcgca | tatttgaaga | ttacaccgtc | tcttggtact | ggattatcat | aggcctggtc | 720 |
| attgccatgg | cgatgagcct | cctgttcatc | atcctgcttc | gcttcctggc | tggtattatg | 780 |

```
gtctgggtga tgatcatcat ggtgattctg gtgctgggct acggaatatt tcactgctac    840
atggagtact cccgactgcg tggtgaggcc ggctctgatg tctctttggt ggacctcggc    900
tttcagacgg atttccgggt gtacctgcac ttacggcaga cctggttggc ctttatgatc    960
attctgagta tccttgaagt cattatcatc ttgctgctca tctttctccg aagagaatt    1020 ctcatcgcga ttgcactcat caaagaagcc agcagggctg tgggatacgt catgtgctcc   1080
ttgctctacc cactggtcac cttcttcttg ctgtgcctct gcatcgccta ctgggccagc   1140
actgctgtct tcctgtccac ttccaacgaa gcggtctata agatctttga tgacagcccc   1200
tgcccattta ctgcgaaaac ctgcaaccca gagaccttcc cctcctccaa tgagtcccgc   1260
caatgcccca atgcccgttg ccagttcgcc ttctacggtg gtgagtcggg ctaccaccgg   1320
gccctgctgg gcctgcagat cttcaatgcc ttcatgttct tctggttggc caacttcgtg   1380
ctggcgctgg ccaggtcac gctggccggg gccttttgcct cctactactg ggccctgcgc   1440
aagccggacg acctgccggc cttcccgctc ttctctgcct tggccgggc gctcaggtac   1500 cacacaggct ccctggcctt tggcgcgctc atcctggcca ttgtgcagat catccgtgtg   1560
atactcgagt acctggatca gcggctgaaa gctgcagaga acaagtttgc caagtgcctc   1620
atgacctgtc tcaaatgctg cttctggtgc ctggagaagt tcatcaaatt ccttaatagg   1680
aatgcctaca tcatgattgc catctacggc accaatttct gcacctcggc caggaatgcc   1740
ttcttcctgc tcatgagaaa catcatcaga gtggctgtcc tggataaagt tactgacttc   1800
ctcttcctgt gggcaaact tctgatcgtt ggtagtgtgg ggatcctggc tttcttcttc   1860
ttcacccacc gtatcaggat cgtgcaggat acagcaccac ccctcaatta ttactgggtt   1920
cctatactga cggtgatcgt tggctcctac ttgattgcac acggtttctt cagcgtctat   1980
ggcatgtgtg tggacacgct gttcctctgc ttcttggagg acctggagag gaatgacggc   2040
tcggccgaga ggccttactt catgtcttcc accctcaaga aacccttgaa caagaccaac   2100
aagaaggcag cggagtcctg a                                             2121
```

<210> SEQ ID NO 5
<211> LENGTH: 1977
<212> TYPE: DNA
<213> ORGANISM: Homo sapiens
<220> FEATURE:
<221> NAME/KEY: misc_feature
<223> OTHER INFORMATION: FCgamma receptor IIIb DNA (HNA-1)

<400> SEQUENCE: 5

```
cactccagtg tggcatcatg tggcagctgc tcctcccaac tgctctgcta cttctagttt     60
cagctggcat gcggactgaa gatctcccaa aggctgtggt gttcctggag cctcaatggt    120
acagggtgct cgagaaggac agtgtgactc tgaagtgcca gggagcctac tcccctgagg    180
acaattccac acagtggttt cacaatgaga acctcatctc aagccaggcc tcgagctact    240
tcattgacgc tgccacagtc gacgacagtg agagtacag gtgccagaca aacctctcca    300
ccctcagtga cccggtgcag ctagaagtcc atgtcggctg gctgttgctc aggcccctc    360 ggtgggtgtt caaggaggaa gaccctattc acctgaggtg tcacagctgg aagaacactg    420
ctctgcataa ggtcacatat ttacagaatg caaagacag gaagtatttt catcataatt    480
ctgacttcca cattccaaaa gccacactca agatagcgg ctcctacttc tgcaggggggc    540 ttgttgggag taaaaatgtg tcttcagaga ctgtgaacat caccatcact caaggtttgg    600
cagtgtcaac catctcatca ttctctccac ctgggtacca agtctctttc tgcttggtga    660
```

-continued

```
tggtactcct ttttgcagtg gacacaggac tatatttctc tgtgaagaca acatttgaa      720 gctcaacaag agactggaag gaccataaac ttaaatggag aaaggaccct caagacaaat     780 gaccccatc ccatgggagt aataagagca gtggcagcag catctctgaa catttctctg     840
gatttgcaac cccatcatcc tcaggcctct ctacaagcag caggaaacat agaactcaga     900
gccagatcct ttatccaact ctcgattttt ccttggtctc cagtggaagg gaaaagccca     960
tgatcttcaa gcagggaagc cccagtgagt agctgcattc ctagaaattg aagtttcaga    1020
gctacacaaa cacttttttct gtcccaacca ttccctcaca gtaaaacaac aatacaggct    1080
agggatggta atcctttaaa catacaaaaa ttgctcgtat tataaattac ccagtttaga    1140
ggggaaaaaa gaaataatt attcctaaac aaatggataa gtagaattaa tgattgaggc     1200
aggaccctac agagtgtggg aactgctggg gatctagaga attcagtggg accaatgaaa    1260
gcatggctga gaaatagcag ggtagtccag gatagtctaa gggaggtgtt cccatctgag    1320
cccagagata agggtgtctt cctagaacat tagccgtagt ggaattaaca ggaaatcatg    1380
agggtgacgt agaattgagt cttccagggg actctatcag aactggacca tttccaagta    1440
tataacgatg agccctctaa tgctaggagt agcaaatggt cctaggaagg ggactgagga    1500
ttggggtggg ggtggggtgg aaaagaaagt acagaacaaa ccctgtgtca ctgtcccaag    1560
ttaagctaag tgaacagaac tatctcagca tcagaatgag aatgagaaag cctgagaaga    1620
aagaaccaac cacaagcaca caggaaggaa agcgcaggag gtgaaaatgc tttcttggcc    1680
agggtagtaa gaattagagg ttaatgcagg gactgtaaaa ccacctttc tgcttcaatg     1740 tctagttcct gtatagcttt gttcattgca tttattaaac aaatgttgta taccaatac    1800 taaatgtact actgagcttc actgagttac gctgtgaaac tttcaaatcc ttcttcagtc    1860
agttccaatg aggtggggat ggagaagaca attgttgctt atgaaaaaaa gctttagctg    1920
tctcctgttt tgtaagcttt cagtgcaaca tttcttggtt ccaataaagc attttac      1977
```

<210> SEQ ID NO 6
<211> LENGTH: 233
<212> TYPE: PRT
<213> ORGANISM: Homo sapiens
<220> FEATURE:
<221> NAME/KEY: MISC_FEATURE
<223> OTHER INFORMATION: FCgamma receptor IIIb protein (HNA-1)

<400> SEQUENCE: 6

```
Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Asn Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Val Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
```

```
                130                 135                 140
Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
                195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230
```

<210> SEQ ID NO 7
<211> LENGTH: 2364
<212> TYPE: DNA
<213> ORGANISM: Homo sapiens
<220> FEATURE:
<221> NAME/KEY: misc_feature
<223> OTHER INFORMATION: CD177 DNA (HNA-2)

<400> SEQUENCE: 7

```
ctgctgaaaa agcagaaaga gattaccagc cacagacggg tcatgagcgc ggtattactg      60
ctggccctcc tggggttcat cctcccactg ccaggagtgc aggcgctgct ctgccagttt     120
gggacagttc agcatgtgtg gaaggtgtcc gacctgcccc ggcaatggac ccctaagaac     180
accagctgcg acagcggctt ggggtgccag gacacgttga tgctcattga gagcggaccc     240
caagtgagcc tggtgctctc caagggctgc acggaggcca aggaccagga gccccgcgtc     300
actgagcacc ggatgggccc cggcctctcc ctgatctcct acaccttcgt gtgccgccag     360
gaggacttct gcaacaacct cgttaactcc ctcccgcttt gggccccaca gccccccagca    420 gacccaggat ccttgaggtg cccagtctgc ttgtctatgg aaggctgtct ggaggggaca     480
acagaagaga tctgccccaa ggggaccaca cactgttatg atggcctcct caggctcagg     540
ggaggaggca tcttctccaa tctgagagtc cagggatgca tgccccagcc agtttgcaac     600
ctgctcaatg ggacacagga aattgggccc gtgggtatga ctgagaactg cgatatgaaa     660
gattttctga cctgtcatcg ggggaccacc attatgacac acggaaactt ggctcaagaa     720
cccactgatt ggaccacatc gaataccgag atgtgcgagg tggggcaggt gtgtcaggag     780
acgctgctgc tcctagatgt aggactcaca tcaaccctgg tggggacaaa aggctgcagc     840
actgttgggg ctcaaaattc ccagaagacc accatccact cagcccctcc tggggtgctt     900
gtggcctcct atacccactt ctgctcctcg gacctgtgca atagtgccag cagcagcagc     960
gttctgctga actccctccc tcctcaagct gccctgtcc caggagaccg gcagtgtcct    1020
acctgtgtgc agccccttgg aacctgttca agtggctccc ccgaatgac ctgccccagg    1080 ggcgccactc attgttatga tgggtacatt catctctcag gaggtgggct gtccaccaaa    1140
atgagcattc agggctgcgt ggcccaacct tccagcttct gttgaaccca ccagacaa      1200 atcgggatct tctctgcgcg tgagaagcgt gatgtgcagc ctcctgcctc tcagcatgag    1260
ggaggtgggg ctgagggcct ggagtctctc acttgggggg tggggctggc actgccccca    1320
gcgctgtggt ggggagtggt ttgcccttcc tgctaactct attaccccca cgattcttca    1380
ccgctgctga ccaccacac tcaacctccc tctgacctca taacctaatg gccttggaca    1440
ccagattctt tcccattctg tccatgaatc atcttcccca cacacaatca ttcatatcta    1500
```

-continued

```
ctcacctaac agcaacactg gggagagcct ggagcatccg gacttgccct atgggagagg      1560
ggacgctgga ggagtggctg catgtatctg ataatacaga ccctgtcctt tctcccagtg      1620
ctgggatttc tccatgtgag ggggcagcag gacacccagg gatctagcgt ggggaggag       1680 aggagcctaa tgagaaaatg accatctaaa gcctgccctt cattggtctg gttcacgtct      1740
ccaaaccagc ttggatggta gcagagactt cagggtgctc cagccaaacg tatttgggca      1800
tcaccatgac ctgggagggg aagatgcact gagacgtatg aggcttccag cctagcagcc      1860
agggccctag cacaaacagg aggctcgccc catctgagca actgcaggag aggttagtac      1920
agtcatgcat tgcttaacga cagggacgtg tcgttagaaa tgtgtcgtta ggtgatttta      1980
tgaccatagg aacattgtag cgtgcactta caccaaccca gatggtacag cccaatacac      2040
acccaggatg gacgctagag tcgactgctc ctaggctaca agcctgcagt gcatgttatg      2100
gtgtgaatac tgcaggcaat cttaacacca cggcaagtat ttgtgcatct acacacatct      2160
aaacatagaa aaggtacagc ataaatacac tattgtcatc tcagcagacc accgttctat      2220
acgcaattcg tcgctgaccc aaacgttgct atgtagcatc tgcgtatcgt gggataattg      2280
acatgagggc ttgagagaac tccagaaaaa aatgggttag catttcccca gagctgttat      2340
cattgggtct ctcttaccac cata                                             2364
```

<210> SEQ ID NO 8
<211> LENGTH: 437
<212> TYPE: PRT
<213> ORGANISM: Homo sapiens
<220> FEATURE:
<221> NAME/KEY: MISC_FEATURE
<223> OTHER INFORMATION: CD177 protein (HNA-2)

<400> SEQUENCE: 8

```
Met Ser Ala Val Leu Leu Ala Leu Leu Gly Phe Ile Leu Pro Leu
1               5                   10                  15

Pro Gly Val Gln Ala Leu Leu Cys Gln Phe Gly Thr Val Gln His Val
                20                  25                  30

Trp Lys Val Ser Asp Leu Pro Arg Gln Trp Thr Pro Lys Asn Thr Ser
            35                  40                  45

Cys Asp Ser Gly Leu Gly Cys Gln Asp Thr Leu Met Leu Ile Glu Ser
        50                  55                  60

Gly Pro Gln Val Ser Leu Val Leu Ser Lys Gly Cys Thr Glu Ala Lys
65                  70                  75                  80

Asp Gln Glu Pro Arg Val Thr Glu His Arg Met Gly Pro Gly Leu Ser
                85                  90                  95

Leu Ile Ser Tyr Thr Phe Val Cys Arg Gln Glu Asp Phe Cys Asn Asn
                100                 105                 110

Leu Val Asn Ser Leu Pro Leu Trp Ala Pro Gln Pro Ala Asp Pro
            115                 120                 125

Gly Ser Leu Arg Cys Pro Val Cys Leu Ser Met Glu Gly Cys Leu Glu
        130                 135                 140

Gly Thr Thr Glu Glu Ile Cys Pro Lys Gly Thr Thr His Cys Tyr Asp
145                 150                 155                 160

Gly Leu Leu Arg Leu Arg Gly Gly Ile Phe Ser Asn Leu Arg Val
                165                 170                 175

Gln Gly Cys Met Pro Gln Pro Val Cys Asn Leu Leu Asn Gly Thr Gln
                180                 185                 190

Glu Ile Gly Pro Val Gly Met Thr Glu Asn Cys Asp Met Lys Asp Phe
            195                 200                 205
```

```
Leu Thr Cys His Arg Gly Thr Thr Ile Met Thr His Gly Asn Leu Ala
    210                 215                 220

Gln Glu Pro Thr Asp Trp Thr Thr Ser Asn Thr Glu Met Cys Glu Val
225                 230                 235                 240

Gly Gln Val Cys Gln Glu Thr Leu Leu Leu Leu Asp Val Gly Leu Thr
            245                 250                 255

Ser Thr Leu Val Gly Thr Lys Gly Cys Ser Thr Val Gly Ala Gln Asn
        260                 265                 270

Ser Gln Lys Thr Thr Ile His Ser Ala Pro Pro Gly Val Leu Val Ala
    275                 280                 285

Ser Tyr Thr His Phe Cys Ser Ser Asp Leu Cys Asn Ser Ala Ser Ser
290                 295                 300

Ser Ser Val Leu Leu Asn Ser Leu Pro Pro Gln Ala Ala Pro Val Pro
305                 310                 315                 320

Gly Asp Arg Gln Cys Pro Thr Cys Val Gln Pro Leu Gly Thr Cys Ser
            325                 330                 335

Ser Gly Ser Pro Arg Met Thr Cys Pro Arg Gly Ala Thr His Cys Tyr
        340                 345                 350

Asp Gly Tyr Ile His Leu Ser Gly Gly Leu Ser Thr Lys Met Ser
    355                 360                 365

Ile Gln Gly Cys Val Ala Gln Pro Ser Ser Phe Leu Leu Asn His Thr
370                 375                 380

Arg Gln Ile Gly Ile Phe Ser Ala Arg Glu Lys Arg Asp Val Gln Pro
385                 390                 395                 400

Pro Ala Ser Gln His Glu Gly Gly Ala Glu Gly Leu Glu Ser Leu
            405                 410                 415

Thr Trp Gly Val Gly Leu Ala Leu Ala Pro Ala Leu Trp Trp Gly Val
        420                 425                 430

Val Cys Pro Ser Cys
        435

<210> SEQ ID NO 9
<211> LENGTH: 4740
<212> TYPE: DNA
<213> ORGANISM: Homo sapiens
<220> FEATURE:
<221> NAME/KEY: misc_feature
<223> OTHER INFORMATION: CD11b DNA (HNA-4)

<400> SEQUENCE: 9
gaattccgtg gttcctcagt ggtgcctgca accctggtt cacctccttc caggttctgg      60
ctccttccag ccatggctct cagagtcctt ctgttaacag ccttgacctt atgtcatggg     120
ttcaacttgg acactgaaaa cgcaatgacc ttccaagaga cgcaaggggg cttcgggcag     180
agcgtggtcc agcttcaggg atccagggtg gtgttggag ccccccagga gatagtggct     240
gccaaccaaa ggggcagcct ctaccagtgc gactacagca caggctcatg cgagcccatc     300
cgcctgcagg tccccgtgga ggccgtgaac atgtccctgg gcctgtccct ggcagccacc     360
accagccccc ctcagctgct ggcctgtggt cccaccgtgc accagacttg cagtgagaac     420
acgtatgtga aagggctctg cttcctgttt ggatccaacc tacggcagca gccccagaag     480
ttcccagagg ccctccgagg gtgtcctcaa gaggatagtg acattgcctt cttgattgat     540
ggctctggta gcatcatccc acatgacttt cggcggatga aggagtttgt ctcaactgtg     600
atggagcaat taaaaaagtc caaaaccttg ttctctttga tgcagtactc tgaagaattc     660
cggattcact ttaccttcaa agagttccag aacaaccta acccaagatc actggtgaag     720
```

```
ccaataacgc agctgcttgg gcggacacac acggccacgg gcatccgcaa agtggtacga    780
gagctgttta acatcaccaa cggagcccga aagaatgcct ttaagatcct agttgtcatc    840
acggatggag aaaagtttgg cgatcccttg ggatatgagg atgtcatccc tgaggcagac    900
agagagggag tcattcgcta cgtcattggg gtgggagatg ccttccgcag tgagaaatcc    960
cgccaagagc ttaataccat cgcatccaag ccgcctcgtg atcacgtgtt ccaggtgaat   1020
aactttgagg ctctgaagac cattcagaac cagcttcggg agaagatctt tgcgatcgag   1080
ggtactcaga caggaagtag cagctcctttt gagcatgaga tgtctcagga aggcttcagc   1140
gctgccatca cctctaatgg cccttgctg agcactgtgg ggagctatga ctgggctggt   1200
ggagtctttc tatatacatc aaaggagaaa agcaccttca tcaacatgac cagagtggat   1260
tcagacatga atgatgctta cttgggttat gctgccgcca tcatcttacg gaaccgggtg   1320
caaagcctgg ttctggggc acctcgatat cagcacatcg gcctggtagc gatgttcagg   1380
cagaacactg gcatgtggga gtccaacgct aatgtcaagg gcacccagat cggcgcctac   1440
ttcggggcct ccctctgctc cgtggacgtg gacagcaacg gcagcaccga cctggtcctc   1500
atcggggccc ccattactac gagcagacc cgagggggcc aggtgtccgt gtgcccttg    1560
cccaggggc agagggctcg gtggcagtgt gatgctgttc tctacgggga gcagggccaa   1620
ccctggggcc gctttgggc agccctaaca gtgctgggg acgtaaatgg ggacaagctg    1680
acggacgtgg ccattggggc cccaggagag gaggacaacc ggggtgctgt ttacctgttt   1740
cacggaacct caggatctgg catcagcccc tcccatagcc agcggatagc aggctccaag   1800
ctctctccca ggctccagta ttttggtcag tcactgagtg ggggccagga cctcacaatg   1860
gatggactgt tagacctgac tgtaggagcc caggggcacg tgctgctgct caggtcccag   1920
ccagtactga gagtcaaggc aatcatggag ttcaatccca gggaagtggc aaggaatgta   1980
tttgagtgta atgatcaggt ggtgaaaggc aaggaagccg gagaggtcag agtctgcctc   2040
catgtccaga agagcacacg ggatcggcta agagaaggac agatccagag tgttgtgact   2100
tatgacctgg ctctggactc cggccgccca cattcccgcg ccgtcttcaa tgagacaaag   2160
aacagcacac gcagacagac acaggtcttg gggctgaccc agacttgtga gaccctgaaa   2220
ctacagttgc cgaattgcat cgaggaccca gtgagcccca ttgtgctgcg cctgaacttc   2280
tctctggtgg aacgccatt gtctgctttc gggaacctcc ggccagtgct ggcggaggat   2340
gctcagagac tcttcacagc cttgtttccc tttgagaaga attgtggcaa tgacaacatc   2400
tgccaggatg acctcagcat caccttcagt ttcatgagcc tggactgcct cgtggtgggt   2460
gggccccggg agttcaacgt gacagtgact gtgagaaatg atggtgagga ctcctacagg   2520
acacaggtca ccttcttctt cccgcttgac ctgtcctacc ggaaggtgtc cacactccag   2580
aaccagcgct cacagcgatc ctggcgcctg gcctgtgagt ctgcctcctc caccgaagtg   2640
tctgggcct tgaagagcac cagctgcagc ataaaccacc ccatcttccc ggaaaactca   2700
gaggtcacct ttaatatcac gtttgatgta gactctaagg cttcccttgg aaacaaactg   2760
ctcctcaagg ccaatgtgac cagtgagaac aacatgccca gaaccaacaa aaccgaattc   2820
caactggagc tgccggtgaa atatgctgtc tacatggtgg tcaccagcca tggggtctcc   2880
actaaatatc tcaacttcac ggcctcagag aataccagtc gggtcatgca gcatcaatat   2940
caggtcagca acctggggca gaggagcctc cccatcagcc tggtgttctt ggtgcccgtc   3000
cggctgaacc agactgtcat atgggaccgc ccccaggtca ccttctccga gaacctctcg   3060
agtacgtgcc acaccaagga gcgcttgccc tctcactccg actttctggc tgagcttcgg   3120
```

```
aaggccccg  tggtgaactg  ctccatcgct  gtctgccaga  gaatccagtg  tgacatcccg   3180
ttctttggca  tccaggaaga  attcaatgct  accctcaaag  gcaacctctc  gtttgactgg   3240
tacatcaaga  cctcgcataa  ccacctcctg  atcgtgagca  cagctgagat  cttgtttaac   3300
gattccgtgt  tcaccctgct  gccgggacag  ggggcgtttg  tgaggtccca  gacggagacc   3360
aaagtggagc  cgttcgaggt  ccccaacccc  ctgccgctca  tcgtgggcag  ctctgtcggg   3420
ggactgctgc  tcctggccct  catcaccgcc  gcgctgtaca  agctcggctt  cttcaagcgg   3480
caatacaagg  acatgatgag  tgaaggggggt  ccccccggggg  ccgaaccccca  gtagcggctc   3540 cttcccgaca  gagctgcctc  tcggtggcca  gcaggactct  gcccagacca  cacgtagccc   3600
ccaggctgct  ggacacgtcg  gacagcgaag  tatccccgac  aggacgggct  tgggcttcca   3660
tttgtgtgtg  tgcaagtgtg  tatgtgcgtg  tgtgcgagtg  tgtgcaagtg  tctgtgtgca   3720
agtgtgtgca  cgtgtgcgtg  tgcgtgcatg  tgcactcgca  cgcccatgtg  tgagtgtgtg   3780
caagtatgtg  agtgtgtcca  gtgtgtgtgc  gtgtgtccat  gtgtgtgcag  tgtgtgcatg   3840
tgtgcgagtg  tgtgcatgtg  tgtgctcagg  ggctgtggct  cacgtgtgtg  actcagagtg   3900
tctctggcgt  gtgggtaggt  gacggcagcg  tagcctctcc  ggcagaaggg  aactgcctgg   3960
gctcccttgt  gcgtgggtaa  gccgctgctg  ggttttcctc  cgggagaggg  gacggtcaat   4020
cctgtgggtg  aagagagagg  gaaacacagc  agcatctctc  cactgaaaga  agtgggactt   4080
cccgtcgcct  gcgagcctgc  ggcctgctgg  agcctgcgca  gcttggatgg  atactccatg   4140
agaaaagccg  tgggtggaac  caggagcctc  ctccacacca  gcgctgatgc  ccaataaaga   4200
tgcccactga  ggaatcatga  agcttccttt  ctggattcat  ttattatttc  aatgtgactt   4260
taattttttg  gatggataag  cctgtctatg  gtacaaaaat  cacaaggcat  tcaagtgtac   4320
agtgaaaagt  ctcccttttcc  agatattcaa  gtcacctcct  taaaggtagt  caagattgtg   4380
ttttgaggtt  tccttcagac  agattccagg  cgatgtgcaa  gtgtatgcac  gtgtgcacac   4440
accacacaca  tacacacaca  caagcttttt  tacacaaatg  gtagcatact  ttatattggt   4500
ctgtatcttg  cttttttttca  ccaatatttc  tcagacatcg  gttcatatta  agacataaat   4560
tactttttca  ttcttttata  ccgctgcata  gtattccatt  gtgtgagtgt  accataatgt   4620
atttaaccag  tcttcttttg  atatactatt  ttcatctctt  gttattgcat  ctgctgagtt   4680
aataaatcaa  atatatgtca  aaaaaaaaaa  aaaaaaaaaa  aaaaaaaaaa  aaaaaaaaaa   4740
```

<210> SEQ ID NO 10
<211> LENGTH: 1153
<212> TYPE: PRT
<213> ORGANISM: Homo sapiens
<220> FEATURE:
<221> NAME/KEY: MISC_FEATURE
<223> OTHER INFORMATION: CD11b protein (HNA-4)

<400> SEQUENCE: 10

```
Met Ala Leu Arg Val Leu Leu Thr Ala Leu Thr Leu Cys His Gly
1               5                   10                  15

Phe Asn Leu Asp Thr Glu Asn Ala Met Thr Phe Gln Glu Asn Ala Arg
                20                  25                  30

Gly Phe Gly Gln Ser Val Val Gln Leu Gln Gly Ser Arg Val Val Val
            35                  40                  45

Gly Ala Pro Gln Glu Ile Val Ala Ala Asn Gln Arg Gly Ser Leu Tyr
        50                  55                  60

Gln Cys Asp Tyr Ser Thr Gly Ser Cys Glu Pro Ile Arg Leu Gln Val
65                  70                  75                  80
```

```
Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
            100                 105                 110

Cys Ser Glu Asn Thr Tyr Val Lys Gly Leu Cys Phe Leu Phe Gly Ser
            115                 120                 125

Asn Leu Arg Gln Gln Pro Gln Lys Phe Pro Glu Ala Leu Arg Gly Cys
        130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
            180                 185                 190

Ser Glu Glu Phe Arg Ile His Phe Thr Phe Lys Glu Phe Gln Asn Asn
        195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
            260                 265                 270

Pro Glu Ala Asp Arg Glu Gly Val Ile Arg Tyr Val Ile Gly Val Gly
        275                 280                 285

Asp Ala Phe Arg Ser Glu Lys Ser Arg Gln Glu Leu Asn Thr Ile Ala
    290                 295                 300

Ser Lys Pro Pro Arg Asp His Val Phe Gln Val Asn Asn Phe Glu Ala
305                 310                 315                 320

Leu Lys Thr Ile Gln Asn Gln Leu Arg Glu Lys Ile Phe Ala Ile Glu
                325                 330                 335

Gly Thr Gln Thr Gly Ser Ser Ser Ser Phe Glu His Glu Met Ser Gln
            340                 345                 350

Glu Gly Phe Ser Ala Ala Ile Thr Ser Asn Gly Pro Leu Leu Ser Thr
        355                 360                 365

Val Gly Ser Tyr Asp Trp Ala Gly Gly Val Phe Leu Tyr Thr Ser Lys
    370                 375                 380

Glu Lys Ser Thr Phe Ile Asn Met Thr Arg Val Asp Ser Asp Met Asn
385                 390                 395                 400

Asp Ala Tyr Leu Gly Tyr Ala Ala Ala Ile Ile Leu Arg Asn Arg Val
                405                 410                 415

Gln Ser Leu Val Leu Gly Ala Pro Arg Tyr Gln His Ile Gly Leu Val
            420                 425                 430

Ala Met Phe Arg Gln Asn Thr Gly Met Trp Glu Ser Asn Ala Asn Val
        435                 440                 445

Lys Gly Thr Gln Ile Gly Ala Tyr Phe Gly Ala Ser Leu Cys Ser Val
    450                 455                 460

Asp Val Asp Ser Asn Gly Ser Thr Asp Leu Val Leu Ile Gly Ala Pro
465                 470                 475                 480

His Tyr Tyr Glu Gln Thr Arg Gly Gly Gln Val Ser Val Cys Pro Leu
                485                 490                 495

Pro Arg Gly Gln Arg Ala Arg Trp Gln Cys Asp Ala Val Leu Tyr Gly
```

```
                    500             505             510
Glu Gln Gly Gln Pro Trp Gly Arg Phe Gly Ala Ala Leu Thr Val Leu
            515                 520                 525

Gly Asp Val Asn Gly Asp Lys Leu Thr Asp Val Ala Ile Gly Ala Pro
        530                 535                 540

Gly Glu Glu Asp Asn Arg Gly Ala Val Tyr Leu Phe His Gly Thr Ser
545                 550                 555                 560

Gly Ser Gly Ile Ser Pro Ser His Ser Gln Arg Ile Ala Gly Ser Lys
                565                 570                 575

Leu Ser Pro Arg Leu Gln Tyr Phe Gly Gln Ser Leu Ser Gly Gly Gln
            580                 585                 590

Asp Leu Thr Met Asp Gly Leu Val Asp Leu Thr Val Gly Ala Gln Gly
        595                 600                 605

His Val Leu Leu Leu Arg Ser Gln Pro Val Leu Arg Val Lys Ala Ile
    610                 615                 620

Met Glu Phe Asn Pro Arg Glu Val Ala Arg Asn Val Phe Glu Cys Asn
625                 630                 635                 640

Asp Gln Val Val Lys Gly Lys Glu Ala Gly Glu Val Arg Val Cys Leu
                645                 650                 655

His Val Gln Lys Ser Thr Arg Asp Arg Leu Arg Glu Gly Gln Ile Gln
            660                 665                 670

Ser Val Val Thr Tyr Asp Leu Ala Leu Asp Ser Gly Arg Pro His Ser
        675                 680                 685

Arg Ala Val Phe Asn Glu Thr Lys Asn Ser Thr Arg Arg Gln Thr Gln
    690                 695                 700

Val Leu Gly Leu Thr Gln Thr Cys Glu Thr Leu Lys Leu Gln Leu Pro
705                 710                 715                 720

Asn Cys Ile Glu Asp Pro Val Ser Pro Ile Val Leu Arg Leu Asn Phe
                725                 730                 735

Ser Leu Val Gly Thr Pro Leu Ser Ala Phe Gly Asn Leu Arg Pro Val
            740                 745                 750

Leu Ala Glu Asp Ala Gln Arg Leu Phe Thr Ala Leu Phe Pro Phe Glu
        755                 760                 765

Lys Asn Cys Gly Asn Asp Asn Ile Cys Gln Asp Asp Leu Ser Ile Thr
    770                 775                 780

Phe Ser Phe Met Ser Leu Asp Cys Leu Val Val Gly Gly Pro Arg Glu
785                 790                 795                 800

Phe Asn Val Thr Val Thr Val Arg Asn Asp Gly Glu Asp Ser Tyr Arg
                805                 810                 815

Thr Gln Val Thr Phe Phe Phe Pro Leu Asp Leu Ser Tyr Arg Lys Val
            820                 825                 830

Ser Thr Leu Gln Asn Gln Arg Ser Gln Arg Ser Trp Arg Leu Ala Cys
        835                 840                 845

Glu Ser Ala Ser Ser Thr Glu Val Ser Gly Ala Leu Lys Ser Thr Ser
    850                 855                 860

Cys Ser Ile Asn His Pro Ile Phe Pro Glu Asn Ser Glu Val Thr Phe
865                 870                 875                 880

Asn Ile Thr Phe Asp Val Asp Ser Lys Ala Ser Leu Gly Asn Lys Leu
                885                 890                 895

Leu Leu Lys Ala Asn Val Thr Ser Glu Asn Asn Met Pro Arg Thr Asn
            900                 905                 910

Lys Thr Glu Phe Gln Leu Glu Leu Pro Val Lys Tyr Ala Val Tyr Met
        915                 920                 925
```

Val Val Thr Ser His Gly Val Ser Thr Lys Tyr Leu Asn Phe Thr Ala
         930                 935                 940

Ser Glu Asn Thr Ser Arg Val Met Gln His Gln Tyr Gln Val Ser Asn
945                 950                 955                 960

Leu Gly Gln Arg Ser Leu Pro Ile Ser Leu Val Phe Leu Val Pro Val
                965                 970                 975

Arg Leu Asn Gln Thr Val Ile Trp Asp Arg Pro Gln Val Thr Phe Ser
            980                 985                 990

Glu Asn Leu Ser Ser Thr Cys His  Thr Lys Glu Arg Leu  Pro Ser His
            995                 1000                1005

Ser Asp  Phe Leu Ala Glu Leu  Arg Lys Ala Pro Val  Val Asn Cys
    1010                1015                1020

Ser Ile  Ala Val Cys Gln Arg  Ile Gln Cys Asp Ile  Pro Phe Phe
1025                1030                1035

Gly Ile  Gln Glu Glu Phe Asn  Ala Thr Leu Lys Gly  Asn Leu Ser
1040                1045                1050

Phe Asp  Trp Tyr Ile Lys Thr  Ser His Asn His Leu  Leu Ile Val
1055                1060                1065

Ser Thr  Ala Glu Ile Leu Phe  Asn Asp Ser Val Phe  Thr Leu Leu
1070                1075                1080

Pro Gly  Gln Gly Ala Phe Val  Arg Ser Gln Thr Glu  Thr Lys Val
1085                1090                1095

Glu Pro  Phe Glu Val Pro Asn  Pro Leu Pro Leu Ile  Val Gly Ser
1100                1105                1110

Ser Val  Gly Gly Leu Leu Leu  Leu Ala Leu Ile Thr  Ala Ala Leu
1115                1120                1125

Tyr Lys  Leu Gly Phe Phe Lys  Arg Gln Tyr Lys Asp  Met Met Ser
1130                1135                1140

Glu Gly  Gly Pro Pro Gly Ala  Glu Pro Gln
1145                1150

<210> SEQ ID NO 11
<211> LENGTH: 5133
<212> TYPE: DNA
<213> ORGANISM: Homo sapiens
<220> FEATURE:
<221> NAME/KEY: misc_feature
<223> OTHER INFORMATION: CD11a DNA (HNA-5)

<400> SEQUENCE: 11
cctctttcac cctgtctagg ttgccagcaa atcccacggg cctcctgacg ctgcccctgg    60
ggccacaggt ccctcgagtg ctggaaggat gaaggattcc tgcatcactg tgatggccat   120
ggcgctgctg tctgggttct ttttcttcgc gccggcctcg agctacaacc tggacgtgcg   180
gggcgcgcgg agcttctccc caccgcgcgc cgggaggcac tttggatacc gcgtcctgca   240
ggtcggaaac ggggtcatcg tgggagctcc aggggagggg aacagcacag gaagcctcta   300
tcagtgccag tcgggcacag gacactgcct gccagtcacc ctgagaggtt ccaactatac   360
ctccaagtac ttgggaatga ccttggcaac agaccccaca gatggaagca ttttggcctg   420
tgaccctggg ctgtctcgaa cgtgtgacca gaacacctat ctgagtggcc tgtgttacct   480
cttccgccaa aatctgcagg gtcccatgct gcagggcgc cctggttttc aggaatgtat   540
caagggcaac gtagacctgg tatttctgtt tgatggttcg atgagcttgc agccagatga   600
atttcagaaa attctggact tcatgaagga tgtgatgaag aaactcagca acacttcgta   660
ccagtttgct gctgttcagt tttccacaag ctacaaaaca gaatttgatt tctcagatta   720

-continued

```
tgttaaatgg aaggaccctg atgctctgct gaagcatgta agcacatgt tgctgttgac      780
caatacctt  ggtgccatca attatgtcgc gacagaggtg ttccgggagg agctgggggc     840
ccggccagat gccaccaaag tgcttatcat catcacggat ggggaggcca ctgacagtgg     900
caacatcgat gcgccaaag  acatcatccg ctacatcatc gggattggaa agcattttca     960
gaccaaggag agtcaggaga ccctccacaa atttgcatca aaacccgcga gcgagtttgt    1020
gaaaattctg acacatttg  agaagctgaa agatctattc actgagctgc agaagaagat    1080
ctatgtcatt gagggcacaa gcaaacagga cctgacttcc ttcaacatgg agctgtcctc    1140
cagcggcatc agtgctgacc tcagcagggg ccatgcagtc gtgggggcag taggagccaa    1200
ggactgggct gggggctttc ttgacctgaa ggcagacctg caggatgaca catttattgg    1260
gaatgaacca ttgacaccag aagtgagagc aggctatttg ggttacaccg tgacctggct    1320
gccctcccgg caaaagactt cgttgctggc ctcgggagcc cctcgatacc agcacatggg    1380
ccgagtgctg ctgttccaag agccacaggg cggaggacac tggagccagg tccagacaat    1440
ccatgggacc cagattggct cttatttcgg tggggagctg tgtggcgtcg acgtggacca    1500
agatggggag acagagctgc tgctgattgg tgccccactg ttctatgggg agcagagagg    1560
aggccgggtg tttatctacc agagaagaca gttgggtttt gaagaagtct cagagctgca    1620
ggggga cccc ggctacccac tcgggcggtt tggagaagcc atcactgctc tgacagacat    1680
caacggcgat gggctggtag acgtggctgt gggggcccct ctggaggagc aggggctgt     1740
gtacatcttc aatgggaggc acggggggct tagtccccag ccaagtcagc ggatagaagg    1800
gacccaagtg ctctcaggaa ttcagtggtt tggacgctcc atccatgggg tgaaggacct    1860
tgaaggggat ggcttggcag atgtggctgt ggggctgag  agccagatga tcgtgctgag    1920
ctccggccc  gtggtggata tggtcaccct gatgtccttc tctccagctg agatcccagt    1980
gcatgaagtg gagtgctcct attcaaccag taacaagatg aaagaaggag ttaatatcac    2040
aatctgtttc cagatcaagt ctctctaccc ccagttccaa ggccgcctgg ttgccaatct    2100
cacttacact ctgcagctgg atggccaccg gaccagaaga cgggggttgt tcccaggagg    2160
gagacatgaa ctcagaagga atatagctgt caccaccagc atgtcatgca ctgacttctc    2220
atttcatttc ccggtatgtg ttcaagacct catctccccc atcaatgttt ccctgaattt    2280
ctctcttttgg gaggaggaag ggacaccgag ggaccaaagg gcgcagggca aggacatacc    2340
gcccatcctg agaccctccc tgcactcgga aacctgggag atcccttttg agaagaactg    2400
tggggaggac aagaagtgtg aggcaaaactt gagagtgtcc ttctctcctg caagatccag    2460
agccctgcgt ctaactgctt ttgccagcct ctctgtggag ctgagcctga gtaacttgga    2520
agaagatgct tactgggtcc agctggacct gcacttcccc ccgggactct ccttccgcaa    2580
ggtggagatg ctgaagcccc atagccagat acctgtgagc tgcgaggagc ttcctgaaga    2640
gtccaggctt ctgtccaggg cattatcttg caatgtgagc tctcccatct tcaaagcagg    2700
ccactcggtt gctctgcaga tgatgtttaa tacactggta aacagctcct gggggactc     2760
ggttgaattg cacgccaatg tgacctgtaa caatgaggac tcagacctcc tggaggacaa    2820
ctcagccact accatcatcc ccatcctgta ccccatcaac atcctcatcc aggaccaaga    2880
agactccaca ctctatgtca gtttcacccc caaaggcccc aagatccacc aagtcaagca    2940
catgtaccag gtgaggatcc agccttccat ccacgaccac aacatacccc ccctggaggc    3000
tgtggttggg gtgccacagc ctcccagcga ggggcccatc acacaccagt ggagcgtgca    3060
gatggagcct cccgtgccct gccactatga ggatctggag aggctcccgg atgcagctga    3120
```

```
gccttgtctc cccggagccc tgttccgctg ccctgttgtc ttcaggcagg agatcctcgt    3180
ccaagtgatc gggactctgg agctggtggg agagatcgag gcctcttcca tgttcagcct    3240
ctgcagctcc ctctccatct ccttcaacag cagcaagcat tccacctct atggcagcaa     3300 cgcctccctg gcccaggttg tcatgaaggt tgacgtggtg tatgagaagc agatgctcta    3360
cctctacgtg ctgagcggca tcgggggggct gctgctgctg ctgctcattt tcatagtgct   3420
gtacaaggtt ggtttcttca acggaacct gaaggagaag atggaggctg cagaggtgt      3480 cccgaatgga atccctgcag aagactctga gcagctggca tctgggcaag aggctgggga   3540
tcccggctgc ctgaagcccc tccatgagaa ggactctgag agtggtggtg caaggactg    3600 agtccaggcc tgtgaggtgc agagtgccca gaactggact caggatgccc agggccactc    3660
tgcctctgcc tgcattctgc cgtgtgccct cgggcgagtc actgcctctc ctggccctc    3720 agtttcccta tctcgaacat ggaactcatt cctgaatgtc tcctttgcag gctcataggg    3780
aagacctgct gagggaccag ccaagagggc tgcaaaagtg agggcttgtc attaccagac    3840
ggttcaccag cctctcttgg ttccttcctt ggaagagaat gtctgatcta aatgtggaga    3900
aactgtagtc tcaggaccta gggatgttct ggccctcacc cctgccctgg gatgtccaca    3960
gatgcctcca cccccagaa cctgtccttg cacactcccc tgcactggag tccagtctct     4020
tctgctggca gaaagcaaat gtgacctgtg tcactacgtg actgtggcac acgccttgtt    4080
cttggccaaa gaccaaattc cttggcatgc cttccagcac cctgcaaaat gagaccctcg    4140
tggccttccc cagcctcttc tagagccgtg atgcctccct gttgaagctc tggtgacacc    4200
agcctttctc ccaggccagg ctccttcctg tcttcctgca ttcacccaga cagctccctc    4260
tgcctgaacc ttccatctcg cccacccctc cttccttgac cagcagatcc cagctcacgt    4320
cacacacttg gttgggtcct cacatctttc acacttccac cacctgcac tactccctca     4380 aagcacacgt catgttttctt catccggcag cctggatgtt ttttccctgt ttaatgattg    4440
acgtacttag cagctatctc tcagtgaact gtgagggtaa aggctatact tgtcttgttc    4500
accttgggat gacgccgcat gatatgtcag ggcgtgggac atctagtagg tgcttgacat    4560
aatttcactg aattaatgac agagccagtg ggaagataca gaaaaagagg gccggggctg    4620
ggcgcggtgg ttcacgcctg taatcccagc actttgggag gccaaggagg gtggatcacc    4680
tgaggtcagg agttagaggc cagcctggcg aaacccatc tctactaaaa atacaaaatc      4740
caggcgtggt ggcacacacc tgtagtccca gctactcagg aggttgaggt aggagaattg    4800
cttgaacctg ggaggtggag gttgcagtga gccaagattg cgccattgca ctccagcctg    4860
ggcaacacag cgagactccg tctcaaggaa aaaataaaaa taaaaagcgg gcacgggccc    4920
ggacatcccc acccttggag gctgtcttct caggctctgc cctgccctag ctccacaccc    4980
tctcccagga cccatcacgc ctgtgcagtg gccccacag aaagactgag ctcaaggtgg      5040
gaaccacgtg tgctaacttg gagccccagt gccaagcaca gtgcctgcat gtatttatcc     5100
aataaatgtg aaattctgtc caaaaaaaaa aaa                                  5133
```

<210> SEQ ID NO 12
<211> LENGTH: 1170
<212> TYPE: PRT
<213> ORGANISM: Homo sapiens
<220> FEATURE:
<221> NAME/KEY: MISC_FEATURE
<223> OTHER INFORMATION: CD11a protein (HNA-5)

<400> SEQUENCE: 12

Met Lys Asp Ser Cys Ile Thr Val Met Ala Met Ala Leu Leu Ser Gly

-continued

```
1               5                   10                  15
Phe Phe Phe Phe Ala Pro Ala Ser Ser Tyr Asn Leu Asp Val Arg Gly
                20                  25                  30
Ala Arg Ser Phe Ser Pro Pro Arg Ala Gly Arg His Phe Gly Tyr Arg
                35                  40                  45
Val Leu Gln Val Gly Asn Gly Val Ile Val Gly Ala Pro Gly Glu Gly
    50                  55                  60
Asn Ser Thr Gly Ser Leu Tyr Gln Cys Gln Ser Gly Thr Gly His Cys
65                  70                  75                  80
Leu Pro Val Thr Leu Arg Gly Ser Asn Tyr Thr Ser Lys Tyr Leu Gly
                85                  90                  95
Met Thr Leu Ala Thr Asp Pro Thr Asp Gly Ser Ile Leu Ala Cys Asp
                100                 105                 110
Pro Gly Leu Ser Arg Thr Cys Asp Gln Asn Thr Tyr Leu Ser Gly Leu
                115                 120                 125
Cys Tyr Leu Phe Arg Gln Asn Leu Gln Gly Pro Met Leu Gln Gly Arg
                130                 135                 140
Pro Gly Phe Gln Glu Cys Ile Lys Gly Asn Val Asp Leu Val Phe Leu
145                 150                 155                 160
Phe Asp Gly Ser Met Ser Leu Gln Pro Asp Glu Phe Gln Lys Ile Leu
                165                 170                 175
Asp Phe Met Lys Asp Val Met Lys Lys Leu Ser Asn Thr Ser Tyr Gln
                180                 185                 190
Phe Ala Ala Val Gln Phe Ser Thr Ser Tyr Lys Thr Glu Phe Asp Phe
                195                 200                 205
Ser Asp Tyr Val Lys Arg Lys Asp Pro Asp Ala Leu Leu Lys His Val
210                 215                 220
Lys His Met Leu Leu Leu Thr Asn Thr Phe Gly Ala Ile Asn Tyr Val
225                 230                 235                 240
Ala Thr Glu Val Phe Arg Glu Glu Leu Gly Ala Arg Pro Asp Ala Thr
                245                 250                 255
Lys Val Leu Ile Ile Ile Thr Asp Gly Glu Ala Thr Asp Ser Gly Asn
                260                 265                 270
Ile Asp Ala Ala Lys Asp Ile Ile Arg Tyr Ile Ile Gly Ile Gly Lys
                275                 280                 285
His Phe Gln Thr Lys Glu Ser Gln Glu Thr Leu His Lys Phe Ala Ser
                290                 295                 300
Lys Pro Ala Ser Glu Phe Val Lys Ile Leu Asp Thr Phe Glu Lys Leu
305                 310                 315                 320
Lys Asp Leu Phe Thr Glu Leu Gln Lys Lys Ile Tyr Val Ile Glu Gly
                325                 330                 335
Thr Ser Lys Gln Asp Leu Thr Ser Phe Asn Met Glu Leu Ser Ser Ser
                340                 345                 350
Gly Ile Ser Ala Asp Leu Ser Arg Gly His Ala Val Val Gly Ala Val
                355                 360                 365
Gly Ala Lys Asp Trp Ala Gly Gly Phe Leu Asp Leu Lys Ala Asp Leu
                370                 375                 380
Gln Asp Asp Thr Phe Ile Gly Asn Glu Pro Leu Thr Pro Glu Val Arg
385                 390                 395                 400
Ala Gly Tyr Leu Gly Tyr Thr Val Thr Trp Leu Pro Ser Arg Gln Lys
                405                 410                 415
Thr Ser Leu Leu Ala Ser Gly Ala Pro Arg Tyr Gln His Met Gly Arg
                420                 425                 430
```

-continued

```
Val Leu Leu Phe Gln Glu Pro Gln Gly Gly His Trp Ser Gln Val
        435                 440                 445

Gln Thr Ile His Gly Thr Gln Ile Gly Ser Tyr Phe Gly Gly Leu
        450                 455                 460

Cys Gly Val Asp Val Asp Gln Asp Gly Glu Thr Glu Leu Leu Leu Ile
465                 470                 475                 480

Gly Ala Pro Leu Phe Tyr Gly Glu Gln Arg Gly Gly Arg Val Phe Ile
                485                 490                 495

Tyr Gln Arg Arg Gln Leu Gly Phe Glu Glu Val Ser Glu Leu Gln Gly
                500                 505                 510

Asp Pro Gly Tyr Pro Leu Gly Arg Phe Gly Glu Ala Ile Thr Ala Leu
                515                 520                 525

Thr Asp Ile Asn Gly Asp Gly Leu Val Asp Val Ala Val Gly Ala Pro
530                 535                 540

Leu Glu Glu Gln Gly Ala Val Tyr Ile Phe Asn Gly Arg His Gly Gly
545                 550                 555                 560

Leu Ser Pro Gln Pro Ser Gln Arg Ile Glu Gly Thr Gln Val Leu Ser
                565                 570                 575

Gly Ile Gln Trp Phe Gly Arg Ser Ile His Gly Val Lys Asp Leu Glu
                580                 585                 590

Gly Asp Gly Leu Ala Asp Val Ala Val Gly Ala Glu Ser Gln Met Ile
                595                 600                 605

Val Leu Ser Ser Arg Pro Val Val Asp Met Val Thr Leu Met Ser Phe
610                 615                 620

Ser Pro Ala Glu Ile Pro Val His Glu Val Glu Cys Ser Tyr Ser Thr
625                 630                 635                 640

Ser Asn Lys Met Lys Glu Gly Val Asn Ile Thr Ile Cys Phe Gln Ile
                645                 650                 655

Lys Ser Leu Ile Pro Gln Phe Gln Gly Arg Leu Val Ala Asn Leu Thr
                660                 665                 670

Tyr Thr Leu Gln Leu Asp Gly His Arg Thr Arg Arg Arg Gly Leu Phe
                675                 680                 685

Pro Gly Gly Arg His Glu Leu Arg Arg Asn Ile Ala Val Thr Thr Ser
                690                 695                 700

Met Ser Cys Thr Asp Phe Ser Phe His Phe Pro Val Cys Val Gln Asp
705                 710                 715                 720

Leu Ile Ser Pro Ile Asn Val Ser Leu Asn Phe Ser Leu Trp Glu Glu
                725                 730                 735

Glu Gly Thr Pro Arg Asp Gln Arg Ala Gln Gly Lys Asp Ile Pro Pro
                740                 745                 750

Ile Leu Arg Pro Ser Leu His Ser Glu Thr Trp Glu Ile Pro Phe Glu
                755                 760                 765

Lys Asn Cys Gly Glu Asp Lys Lys Cys Glu Ala Asn Leu Arg Val Ser
770                 775                 780

Phe Ser Pro Ala Arg Ser Arg Ala Leu Arg Leu Thr Ala Phe Ala Ser
785                 790                 795                 800

Leu Ser Val Glu Leu Ser Leu Ser Asn Leu Glu Glu Asp Ala Tyr Trp
                805                 810                 815

Val Gln Leu Asp Leu His Phe Pro Pro Gly Leu Ser Phe Arg Lys Val
                820                 825                 830

Glu Met Leu Lys Pro His Ser Gln Ile Pro Val Ser Cys Glu Glu Leu
                835                 840                 845

Pro Glu Glu Ser Arg Leu Leu Ser Arg Ala Leu Ser Cys Asn Val Ser
                850                 855                 860
```

Ser Pro Ile Phe Lys Ala Gly His Ser Val Ala Leu Gln Met Met Phe
865                 870                 875                 880

Asn Thr Leu Val Asn Ser Ser Trp Gly Asp Ser Val Glu Leu His Ala
                885                 890                 895

Asn Val Thr Cys Asn Asn Glu Asp Ser Asp Leu Leu Glu Asp Asn Ser
            900                 905                 910

Ala Thr Thr Ile Ile Pro Ile Leu Tyr Pro Ile Asn Ile Leu Ile Gln
        915                 920                 925

Asp Gln Glu Asp Ser Thr Leu Tyr Val Ser Phe Thr Pro Lys Gly Pro
    930                 935                 940

Lys Ile His Gln Val Lys His Met Tyr Gln Val Arg Ile Gln Pro Ser
945                 950                 955                 960

Ile His Asp His Asn Ile Pro Thr Leu Glu Ala Val Val Gly Val Pro
                965                 970                 975

Gln Pro Pro Ser Glu Gly Pro Ile Thr His Gln Trp Ser Val Gln Met
            980                 985                 990

Glu Pro Pro Val Pro Cys His Tyr Glu Asp Leu Glu Arg Leu Pro Asp
        995                 1000                1005

Ala Ala Glu Pro Cys Leu Pro Gly Ala Leu Phe Arg Cys Pro Val
    1010                1015                1020

Val Phe Arg Gln Glu Ile Leu Val Gln Val Ile Gly Thr Leu Glu
1025                1030                1035

Leu Val Gly Glu Ile Glu Ala Ser Ser Met Phe Ser Leu Cys Ser
1040                1045                1050

Ser Leu Ser Ile Ser Phe Asn Ser Ser Lys His Phe His Leu Tyr
1055                1060                1065

Gly Ser Asn Ala Ser Leu Ala Gln Val Val Met Lys Val Asp Val
1070                1075                1080

Val Tyr Glu Lys Gln Met Leu Tyr Leu Tyr Val Leu Ser Gly Ile
1085                1090                1095

Gly Gly Leu Leu Leu Leu Leu Leu Ile Phe Ile Val Leu Tyr Lys
1100                1105                1110

Val Gly Phe Phe Lys Arg Asn Leu Lys Glu Lys Met Glu Ala Gly
1115                1120                1125

Arg Gly Val Pro Asn Gly Ile Pro Ala Glu Asp Ser Glu Gln Leu
1130                1135                1140

Ala Ser Gly Gln Glu Ala Gly Asp Pro Gly Cys Leu Lys Pro Leu
1145                1150                1155

His Glu Lys Asp Ser Glu Ser Gly Gly Gly Lys Asp
1160                1165                1170

<210> SEQ ID NO 13
<211> LENGTH: 231
<212> TYPE: PRT
<213> ORGANISM: Homo sapiens

<400> SEQUENCE: 13

Met Gly Asp Glu Arg Pro His Tyr Tyr Gly His Gly Thr Pro Gln
1               5                   10                  15

Lys Tyr Asp Pro Thr Phe Lys Gly Pro Ile Tyr Asn Arg Gly Cys Thr
                20                  25                  30

Asp Ile Ile Cys Cys Val Phe Leu Leu Leu Ala Ile Val Gly Tyr Val
            35                  40                  45

Ala Val Gly Ile Ile Ala Trp Thr His Gly Asp Pro Arg Lys Val Ile
        50                  55                  60

Tyr Pro Thr Asp Ser Arg Gly Glu Phe Cys Gly Gln Lys Gly Thr Lys
65                  70                  75                  80

Asn Glu Asn Lys Pro Tyr Leu Phe Tyr Phe Asn Ile Val Lys Cys Ala
                85                  90                  95

Ser Pro Leu Val Leu Leu Glu Phe Gln Cys Pro Thr Pro Gln Ile Cys
            100                 105                 110

Val Glu Lys Cys Pro Asp Arg Tyr Leu Thr Tyr Leu Asn Ala Arg Ser
        115                 120                 125

Ser Arg Asp Phe Glu Tyr Tyr Lys Gln Phe Cys Val Pro Gly Phe Lys
130                 135                 140

Asn Asn Lys Gly Val Ala Glu Val Leu Arg Asp Gly Asp Cys Pro Ala
145                 150                 155                 160

Val Leu Ile Pro Ser Lys Pro Leu Ala Arg Arg Cys Phe Pro Ala Ile
                165                 170                 175

His Ala Tyr Lys Gly Val Leu Met Val Gly Asn Glu Thr Thr Tyr Glu
            180                 185                 190

Asp Gly His Gly Ser Arg Lys Asn Ile Thr Asp Leu Val Glu Gly Ala
        195                 200                 205

Lys Lys Ala Asn Gly Val Leu Glu Ala Arg Gln Leu Ala Met Arg Ile
210                 215                 220

Phe Glu Asp Tyr Thr Val Ser
225                 230

<210> SEQ ID NO 14
<211> LENGTH: 129
<212> TYPE: PRT
<213> ORGANISM: Homo sapiens

<400> SEQUENCE: 14

Trp Thr His Gly Asp Pro Arg Lys Val Ile Tyr Pro Thr Asp Ser Arg
1               5                   10                  15

Gly Glu Phe Cys Gly Gln Lys Gly Thr Lys Asn Glu Asn Lys Pro Tyr
                20                  25                  30

Leu Phe Tyr Phe Asn Ile Val Lys Cys Ala Ser Pro Leu Val Leu Leu
            35                  40                  45

Glu Phe Gln Cys Pro Thr Pro Gln Ile Cys Val Glu Lys Cys Pro Asp
50                  55                  60

Arg Tyr Leu Thr Tyr Leu Asn Ala Arg Ser Ser Arg Asp Phe Glu Tyr
65                  70                  75                  80

Tyr Lys Gln Phe Cys Val Pro Gly Phe Lys Asn Asn Lys Gly Val Ala
                85                  90                  95

Glu Val Leu Arg Asp Gly Asp Cys Pro Ala Val Leu Ile Pro Ser Lys
            100                 105                 110

Pro Leu Ala Arg Arg Cys Phe Pro Ala Ile His Ala Tyr Lys Gly Val
        115                 120                 125

Leu

<210> SEQ ID NO 15
<211> LENGTH: 110
<212> TYPE: PRT
<213> ORGANISM: Homo sapiens

<400> SEQUENCE: 15

Trp Thr His Gly Asp Pro Arg Lys Val Ile Tyr Pro Thr Asp Ser Arg
1               5                   10                  15

Gly Glu Phe Cys Gly Gln Lys Gly Thr Lys Asn Glu Asn Lys Pro Tyr

```
                     20                  25                  30
Leu Phe Tyr Phe Asn Ile Val Lys Cys Ala Ser Pro Leu Val Leu Leu
                 35                  40                  45
Glu Phe Gln Cys Pro Thr Pro Gln Ile Cys Val Glu Lys Cys Pro Asp
             50                  55                  60
Arg Tyr Leu Thr Tyr Leu Asn Ala Arg Ser Ser Arg Asp Phe Glu Tyr
 65                  70                  75                  80
Tyr Lys Gln Phe Cys Val Pro Gly Phe Lys Asn Asn Lys Gly Val Ala
                 85                  90                  95
Glu Val Leu Arg Asp Gly Asp Cys Pro Ala Val Leu Ile Pro
            100                 105                 110

<210> SEQ ID NO 16
<211> LENGTH: 51
<212> TYPE: PRT
<213> ORGANISM: Homo sapiens

<400> SEQUENCE: 16

Glu Lys Cys Pro Asp Arg Tyr Leu Thr Tyr Leu Asn Ala Arg Ser Ser
 1               5                  10                  15
Arg Asp Phe Glu Tyr Tyr Lys Gln Phe Cys Val Pro Gly Phe Lys Asn
                 20                  25                  30
Asn Lys Gly Val Ala Glu Val Leu Arg Asp Gly Asp Cys Pro Ala Val
             35                  40                  45
Leu Ile Pro
     50

<210> SEQ ID NO 17
<211> LENGTH: 652
<212> TYPE: PRT
<213> ORGANISM: Homo sapiens

<400> SEQUENCE: 17

Trp Thr His Gly Asp Pro Arg Lys Val Ile Tyr Pro Thr Asp Ser Arg
 1               5                  10                  15
Gly Glu Phe Cys Gly Gln Lys Gly Thr Lys Asn Glu Asn Lys Pro Tyr
                 20                  25                  30
Leu Phe Tyr Phe Asn Ile Val Lys Cys Ala Ser Pro Leu Val Leu Leu
                 35                  40                  45
Glu Phe Gln Cys Pro Thr Pro Gln Ile Cys Val Glu Lys Cys Pro Asp
             50                  55                  60
Arg Tyr Leu Thr Tyr Leu Asn Ala Arg Ser Ser Arg Asp Phe Glu Tyr
 65                  70                  75                  80
Tyr Lys Gln Phe Cys Val Pro Gly Phe Lys Asn Asn Lys Gly Val Ala
                 85                  90                  95
Glu Val Leu Arg Asp Gly Asp Cys Pro Ala Val Leu Ile Pro Ser Lys
                100                 105                 110
Pro Leu Ala Arg Arg Cys Phe Pro Ala Ile His Ala Tyr Lys Gly Val
            115                 120                 125
Leu Met Val Gly Asn Glu Thr Thr Tyr Glu Asp Gly His Gly Ser Arg
        130                 135                 140
Lys Asn Ile Thr Asp Leu Val Glu Gly Ala Lys Lys Ala Asn Gly Val
145                 150                 155                 160
Leu Glu Ala Arg Gln Leu Ala Met Arg Ile Phe Glu Asp Tyr Thr Val
                165                 170                 175
Ser Trp Tyr Trp Ile Ile Ile Gly Leu Val Ile Ala Met Ala Met Ser
            180                 185                 190
```

```
Leu Leu Phe Ile Ile Leu Leu Arg Phe Leu Ala Gly Ile Met Val Trp
            195                 200                 205

Val Met Ile Ile Met Val Ile Leu Val Leu Gly Tyr Gly Ile Phe His
            210                 215                 220

Cys Tyr Met Glu Tyr Ser Arg Leu Arg Gly Glu Ala Gly Ser Asp Val
225                 230                 235                 240

Ser Leu Val Asp Leu Gly Phe Gln Thr Asp Phe Arg Val Tyr Leu His
            245                 250                 255

Leu Arg Gln Thr Trp Leu Ala Phe Met Ile Ile Leu Ser Ile Leu Glu
            260                 265                 270

Val Ile Ile Ile Leu Leu Leu Ile Phe Leu Arg Lys Arg Ile Leu Ile
            275                 280                 285

Ala Ile Ala Leu Ile Lys Glu Ala Ser Arg Ala Val Gly Tyr Val Met
            290                 295                 300

Cys Ser Leu Leu Tyr Pro Leu Val Thr Phe Phe Leu Leu Cys Leu Cys
305                 310                 315                 320

Ile Ala Tyr Trp Ala Ser Thr Ala Val Phe Leu Ser Thr Ser Asn Glu
            325                 330                 335

Ala Val Tyr Lys Ile Phe Asp Asp Ser Pro Cys Pro Phe Thr Ala Lys
            340                 345                 350

Thr Cys Asn Pro Glu Thr Phe Pro Ser Ser Asn Glu Ser Arg Gln Cys
            355                 360                 365

Pro Asn Ala Arg Cys Gln Phe Ala Phe Tyr Gly Gly Glu Ser Gly Tyr
            370                 375                 380

His Arg Ala Leu Leu Gly Leu Gln Ile Phe Asn Ala Phe Met Phe Phe
385                 390                 395                 400

Trp Leu Ala Asn Phe Val Leu Ala Leu Gly Gln Val Thr Leu Ala Gly
            405                 410                 415

Ala Phe Ala Ser Tyr Tyr Trp Ala Leu Arg Lys Pro Asp Asp Leu Pro
            420                 425                 430

Ala Phe Pro Leu Phe Ser Ala Phe Gly Arg Ala Leu Arg Tyr His Thr
            435                 440                 445

Gly Ser Leu Ala Phe Gly Ala Leu Ile Leu Ala Ile Val Gln Ile Ile
            450                 455                 460

Arg Val Ile Leu Glu Tyr Leu Asp Gln Arg Leu Lys Ala Ala Glu Asn
465                 470                 475                 480

Lys Phe Ala Lys Cys Leu Met Thr Cys Leu Lys Cys Phe Trp Cys
            485                 490                 495

Leu Glu Lys Phe Ile Lys Phe Leu Asn Arg Asn Ala Tyr Ile Met Ile
            500                 505                 510

Ala Ile Tyr Gly Thr Asn Phe Cys Thr Ser Ala Arg Asn Ala Phe Phe
            515                 520                 525

Leu Leu Met Arg Asn Ile Ile Arg Val Ala Val Leu Asp Lys Val Thr
            530                 535                 540

Asp Phe Leu Phe Leu Leu Gly Lys Leu Leu Ile Val Gly Ser Val Gly
545                 550                 555                 560

Ile Leu Ala Phe Phe Phe Thr His Arg Ile Arg Ile Val Gln Asp
            565                 570                 575

Thr Ala Pro Pro Leu Asn Tyr Tyr Trp Val Pro Ile Leu Thr Val Ile
            580                 585                 590

Val Gly Ser Tyr Leu Ile Ala His Gly Phe Phe Ser Val Tyr Gly Met
            595                 600                 605

Cys Val Asp Thr Leu Phe Leu Cys Phe Leu Glu Asp Leu Glu Arg Asn
```

```
                610                 615                 620
Asp Gly Ser Ala Glu Arg Pro Tyr Phe Met Ser Ser Thr Leu Lys Lys
625                 630                 635                 640

Leu Leu Asn Lys Thr Asn Lys Lys Ala Ala Glu Ser
                645                 650

<210> SEQ ID NO 18
<211> LENGTH: 593
<212> TYPE: PRT
<213> ORGANISM: Homo sapiens

<400> SEQUENCE: 18

Glu Lys Cys Pro Asp Arg Tyr Leu Thr Tyr Leu Asn Ala Arg Ser Ser
1               5                   10                  15

Arg Asp Phe Glu Tyr Tyr Lys Gln Phe Cys Val Pro Gly Phe Lys Asn
                20                  25                  30

Asn Lys Gly Val Ala Glu Val Leu Arg Asp Gly Asp Cys Pro Ala Val
            35                  40                  45

Leu Ile Pro Ser Lys Pro Leu Ala Arg Arg Cys Phe Pro Ala Ile His
        50                  55                  60

Ala Tyr Lys Gly Val Leu Met Val Gly Asn Glu Thr Thr Tyr Glu Asp
65                  70                  75                  80

Gly His Gly Ser Arg Lys Asn Ile Thr Asp Leu Val Glu Gly Ala Lys
                85                  90                  95

Lys Ala Asn Gly Val Leu Glu Ala Arg Gln Leu Ala Met Arg Ile Phe
            100                 105                 110

Glu Asp Tyr Thr Val Ser Trp Tyr Trp Ile Ile Gly Leu Val Ile
        115                 120                 125

Ala Met Ala Met Ser Leu Leu Phe Ile Ile Leu Arg Phe Leu Ala
130                 135                 140

Gly Ile Met Val Trp Val Met Ile Ile Met Val Ile Leu Val Leu Gly
145                 150                 155                 160

Tyr Gly Ile Phe His Cys Tyr Met Glu Tyr Ser Arg Leu Arg Gly Glu
                165                 170                 175

Ala Gly Ser Asp Val Ser Leu Val Asp Leu Gly Phe Gln Thr Asp Phe
            180                 185                 190

Arg Val Tyr Leu His Leu Arg Gln Thr Trp Leu Ala Phe Met Ile Ile
        195                 200                 205

Leu Ser Ile Leu Glu Val Ile Ile Leu Leu Ile Phe Leu Arg
210                 215                 220

Lys Arg Ile Leu Ile Ala Ile Ala Leu Ile Lys Glu Ala Ser Arg Ala
225                 230                 235                 240

Val Gly Tyr Val Met Cys Ser Leu Leu Tyr Pro Leu Val Thr Phe Phe
                245                 250                 255

Leu Leu Cys Leu Cys Ile Ala Tyr Trp Ala Ser Thr Ala Val Phe Leu
            260                 265                 270

Ser Thr Ser Asn Glu Ala Val Tyr Lys Ile Phe Asp Asp Ser Pro Cys
        275                 280                 285

Pro Phe Thr Ala Lys Thr Cys Asn Pro Glu Thr Phe Pro Ser Ser Asn
    290                 295                 300

Glu Ser Arg Gln Cys Pro Asn Ala Arg Cys Gln Phe Ala Phe Tyr Gly
305                 310                 315                 320

Gly Glu Ser Gly Tyr His Arg Ala Leu Leu Gly Leu Gln Ile Phe Asn
                325                 330                 335

Ala Phe Met Phe Phe Trp Leu Ala Asn Phe Val Leu Ala Leu Gly Gln
```

```
            340                 345                 350
Val Thr Leu Ala Gly Ala Phe Ala Ser Tyr Tyr Trp Ala Leu Arg Lys
        355                 360                 365

Pro Asp Asp Leu Pro Ala Phe Pro Leu Phe Ser Ala Phe Gly Arg Ala
        370                 375                 380

Leu Arg Tyr His Thr Gly Ser Leu Ala Phe Gly Ala Leu Ile Leu Ala
385                 390                 395                 400

Ile Val Gln Ile Ile Arg Val Ile Leu Glu Tyr Leu Asp Gln Arg Leu
                405                 410                 415

Lys Ala Ala Glu Asn Lys Phe Ala Lys Cys Leu Met Thr Cys Leu Lys
                420                 425                 430

Cys Cys Phe Trp Cys Leu Glu Lys Phe Ile Lys Phe Leu Asn Arg Asn
            435                 440                 445

Ala Tyr Ile Met Ile Ala Ile Tyr Gly Thr Asn Phe Cys Thr Ser Ala
        450                 455                 460

Arg Asn Ala Phe Phe Leu Leu Met Arg Asn Ile Ile Arg Val Ala Val
465                 470                 475                 480

Leu Asp Lys Val Thr Asp Phe Leu Phe Leu Gly Lys Leu Leu Ile
                485                 490                 495

Val Gly Ser Val Gly Ile Leu Ala Phe Phe Phe Thr His Arg Ile
            500                 505                 510

Arg Ile Val Gln Asp Thr Ala Pro Pro Leu Asn Tyr Tyr Trp Val Pro
            515                 520                 525

Ile Leu Thr Val Ile Val Gly Ser Tyr Leu Ile Ala His Gly Phe Phe
        530                 535                 540

Ser Val Tyr Gly Met Cys Val Asp Thr Leu Phe Leu Cys Phe Leu Glu
545                 550                 555                 560

Asp Leu Glu Arg Asn Asp Gly Ser Ala Glu Arg Pro Tyr Phe Met Ser
                565                 570                 575

Ser Thr Leu Lys Lys Leu Leu Asn Lys Thr Asn Lys Lys Ala Ala Glu
            580                 585                 590

Ser

<210> SEQ ID NO 19
<211> LENGTH: 231
<212> TYPE: PRT
<213> ORGANISM: Homo sapiens

<400> SEQUENCE: 19

Met Gly Asp Glu Arg Pro His Tyr Tyr Gly Lys His Gly Thr Pro Gln
1               5                   10                  15

Lys Tyr Asp Pro Thr Phe Lys Gly Pro Ile Tyr Asn Arg Gly Cys Thr
                20                  25                  30

Asp Ile Ile Cys Cys Val Phe Leu Leu Leu Ala Ile Val Gly Tyr Val
            35                  40                  45

Ala Val Gly Ile Ile Ala Trp Thr His Gly Asp Pro Arg Lys Val Ile
        50                  55                  60

Tyr Pro Thr Asp Ser Arg Gly Glu Phe Cys Gly Gln Lys Gly Thr Lys
65                  70                  75                  80

Asn Glu Asn Lys Pro Tyr Leu Phe Tyr Phe Asn Ile Val Lys Cys Ala
                85                  90                  95

Ser Pro Leu Val Leu Leu Glu Phe Gln Cys Pro Thr Pro Gln Ile Cys
            100                 105                 110

Val Glu Lys Cys Pro Asp Arg Tyr Leu Thr Tyr Leu Asn Ala Arg Ser
        115                 120                 125
```

Ser Arg Asp Phe Glu Tyr Tyr Lys Gln Phe Cys Val Pro Gly Phe Lys
    130                 135                 140

Asn Asn Lys Gly Val Ala Glu Val Leu Gln Asp Gly Asp Cys Pro Ala
145                 150                 155                 160

Val Leu Ile Pro Ser Lys Pro Leu Ala Arg Arg Cys Phe Pro Ala Ile
            165                 170                 175

His Ala Tyr Lys Gly Val Leu Met Val Gly Asn Glu Thr Thr Tyr Glu
            180                 185                 190

Asp Gly His Gly Ser Arg Lys Asn Ile Thr Asp Leu Val Glu Gly Ala
            195                 200                 205

Lys Lys Ala Asn Gly Val Leu Glu Ala Arg Gln Leu Ala Met Arg Ile
            210                 215                 220

Phe Glu Asp Tyr Thr Val Ser
225                 230

<210> SEQ ID NO 20
<211> LENGTH: 129
<212> TYPE: PRT
<213> ORGANISM: Homo sapiens

<400> SEQUENCE: 20

Trp Thr His Gly Asp Pro Arg Lys Val Ile Tyr Pro Thr Asp Ser Arg
1               5                   10                  15

Gly Glu Phe Cys Gly Gln Lys Gly Thr Lys Asn Glu Asn Lys Pro Tyr
            20                  25                  30

Leu Phe Tyr Phe Asn Ile Val Lys Cys Ala Ser Pro Leu Val Leu Leu
        35                  40                  45

Glu Phe Gln Cys Pro Thr Pro Gln Ile Cys Val Glu Lys Cys Pro Asp
    50                  55                  60

Arg Tyr Leu Thr Tyr Leu Asn Ala Arg Ser Ser Arg Asp Phe Glu Tyr
65                  70                  75                  80

Tyr Lys Gln Phe Cys Val Pro Gly Phe Lys Asn Asn Lys Gly Val Ala
                85                  90                  95

Glu Val Leu Gln Asp Gly Asp Cys Pro Ala Val Leu Ile Pro Ser Lys
            100                 105                 110

Pro Leu Ala Arg Arg Cys Phe Pro Ala Ile His Ala Tyr Lys Gly Val
            115                 120                 125

Leu

<210> SEQ ID NO 21
<211> LENGTH: 110
<212> TYPE: PRT
<213> ORGANISM: Homo sapiens

<400> SEQUENCE: 21

Trp Thr His Gly Asp Pro Arg Lys Val Ile Tyr Pro Thr Asp Ser Arg
1               5                   10                  15

Gly Glu Phe Cys Gly Gln Lys Gly Thr Lys Asn Glu Asn Lys Pro Tyr
            20                  25                  30

Leu Phe Tyr Phe Asn Ile Val Lys Cys Ala Ser Pro Leu Val Leu Leu
        35                  40                  45

Glu Phe Gln Cys Pro Thr Pro Gln Ile Cys Val Glu Lys Cys Pro Asp
    50                  55                  60

Arg Tyr Leu Thr Tyr Leu Asn Ala Arg Ser Ser Arg Asp Phe Glu Tyr
65                  70                  75                  80

Tyr Lys Gln Phe Cys Val Pro Gly Phe Lys Asn Asn Lys Gly Val Ala

```
                    85                  90                  95
Glu Val Leu Gln Asp Gly Asp Cys Pro Ala Val Leu Ile Pro
                100                 105                 110

<210> SEQ ID NO 22
<211> LENGTH: 51
<212> TYPE: PRT
<213> ORGANISM: Homo sapiens

<400> SEQUENCE: 22

Glu Lys Cys Pro Asp Arg Tyr Leu Thr Tyr Leu Asn Ala Arg Ser Ser
1               5                   10                  15

Arg Asp Phe Glu Tyr Tyr Lys Gln Phe Cys Val Pro Gly Phe Lys Asn
            20                  25                  30

Asn Lys Gly Val Ala Glu Val Leu Gln Asp Gly Asp Cys Pro Ala Val
        35                  40                  45

Leu Ile Pro
    50

<210> SEQ ID NO 23
<211> LENGTH: 652
<212> TYPE: PRT
<213> ORGANISM: Homo sapiens

<400> SEQUENCE: 23

Trp Thr His Gly Asp Pro Arg Lys Val Ile Tyr Pro Thr Asp Ser Arg
1               5                   10                  15

Gly Glu Phe Cys Gly Gln Lys Gly Thr Lys Asn Glu Asn Lys Pro Tyr
            20                  25                  30

Leu Phe Tyr Phe Asn Ile Val Lys Cys Ala Ser Pro Leu Val Leu Leu
        35                  40                  45

Glu Phe Gln Cys Pro Thr Pro Gln Ile Cys Val Glu Lys Cys Pro Asp
    50                  55                  60

Arg Tyr Leu Thr Tyr Leu Asn Ala Arg Ser Ser Arg Asp Phe Glu Tyr
65                  70                  75                  80

Tyr Lys Gln Phe Cys Val Pro Gly Phe Lys Asn Asn Lys Gly Val Ala
                85                  90                  95

Glu Val Leu Gln Asp Gly Asp Cys Pro Ala Val Leu Ile Pro Ser Lys
            100                 105                 110

Pro Leu Ala Arg Arg Cys Phe Pro Ala Ile His Ala Tyr Lys Gly Val
        115                 120                 125

Leu Met Val Gly Asn Glu Thr Thr Tyr Glu Asp Gly His Gly Ser Arg
    130                 135                 140

Lys Asn Ile Thr Asp Leu Val Glu Gly Ala Lys Lys Ala Asn Gly Val
145                 150                 155                 160

Leu Glu Ala Arg Gln Leu Ala Met Arg Ile Phe Glu Asp Tyr Thr Val
                165                 170                 175

Ser Trp Tyr Trp Ile Ile Ile Gly Leu Val Ile Ala Met Ala Met Ser
            180                 185                 190

Leu Leu Phe Ile Ile Leu Leu Arg Phe Leu Ala Gly Ile Met Val Trp
        195                 200                 205

Val Met Ile Ile Met Val Ile Leu Val Leu Gly Tyr Gly Ile Phe His
    210                 215                 220

Cys Tyr Met Glu Tyr Ser Arg Leu Arg Gly Glu Ala Gly Ser Asp Val
225                 230                 235                 240

Ser Leu Val Asp Leu Gly Phe Gln Thr Asp Phe Arg Val Tyr Leu His
                245                 250                 255
```

Leu Arg Gln Thr Trp Leu Ala Phe Met Ile Ile Leu Ser Ile Leu Glu
            260                 265                 270

Val Ile Ile Ile Leu Leu Ile Phe Leu Arg Lys Arg Ile Leu Ile
        275                 280                 285

Ala Ile Ala Leu Ile Lys Glu Ala Ser Arg Ala Val Gly Tyr Val Met
    290                 295                 300

Cys Ser Leu Leu Tyr Pro Leu Val Thr Phe Phe Leu Leu Cys Leu Cys
305                 310                 315                 320

Ile Ala Tyr Trp Ala Ser Thr Ala Val Phe Leu Ser Thr Ser Asn Glu
                325                 330                 335

Ala Val Tyr Lys Ile Phe Asp Asp Ser Pro Cys Pro Phe Thr Ala Lys
                340                 345                 350

Thr Cys Asn Pro Glu Thr Phe Pro Ser Ser Asn Glu Ser Arg Gln Cys
                355                 360                 365

Pro Asn Ala Arg Cys Gln Phe Ala Phe Tyr Gly Gly Glu Ser Gly Tyr
    370                 375                 380

His Arg Ala Leu Leu Gly Leu Gln Ile Phe Asn Ala Phe Met Phe Phe
385                 390                 395                 400

Trp Leu Ala Asn Phe Val Leu Ala Leu Gly Gln Val Thr Leu Ala Gly
                405                 410                 415

Ala Phe Ala Ser Tyr Tyr Trp Ala Leu Arg Lys Pro Asp Asp Leu Pro
                420                 425                 430

Ala Phe Pro Leu Phe Ser Ala Phe Gly Arg Ala Leu Arg Tyr His Thr
                435                 440                 445

Gly Ser Leu Ala Phe Gly Ala Leu Ile Leu Ala Ile Val Gln Ile Ile
    450                 455                 460

Arg Val Ile Leu Glu Tyr Leu Asp Gln Arg Leu Lys Ala Ala Glu Asn
465                 470                 475                 480

Lys Phe Ala Lys Cys Leu Met Thr Cys Leu Lys Cys Cys Phe Trp Cys
                485                 490                 495

Leu Glu Lys Phe Ile Lys Phe Leu Asn Arg Asn Ala Tyr Ile Met Ile
                500                 505                 510

Ala Ile Tyr Gly Thr Asn Phe Cys Thr Ser Ala Arg Asn Ala Phe Phe
            515                 520                 525

Leu Leu Met Arg Asn Ile Ile Arg Val Ala Val Leu Asp Lys Val Thr
                530                 535                 540

Asp Phe Leu Phe Leu Leu Gly Lys Leu Leu Ile Val Gly Ser Val Gly
545                 550                 555                 560

Ile Leu Ala Phe Phe Phe Thr His Arg Ile Arg Ile Val Gln Asp
                565                 570                 575

Thr Ala Pro Pro Leu Asn Tyr Tyr Trp Val Pro Ile Leu Thr Val Ile
            580                 585                 590

Val Gly Ser Tyr Leu Ile Ala His Gly Phe Phe Ser Val Tyr Gly Met
            595                 600                 605

Cys Val Asp Thr Leu Phe Leu Cys Phe Leu Glu Asp Leu Glu Arg Asn
    610                 615                 620

Asp Gly Ser Ala Glu Arg Pro Tyr Phe Met Ser Ser Thr Leu Lys Lys
625                 630                 635                 640

Leu Leu Asn Lys Thr Asn Lys Lys Ala Ala Glu Ser
                645                 650

<210> SEQ ID NO 24
<211> LENGTH: 593
<212> TYPE: PRT

-continued

<213> ORGANISM: Homo sapiens

<400> SEQUENCE: 24

| Glu | Lys | Cys | Pro | Asp | Arg | Tyr | Leu | Thr | Tyr | Leu | Asn | Ala | Arg | Ser | Ser |
| 1 | | | | 5 | | | | | 10 | | | | | 15 | |

Arg Asp Phe Glu Tyr Tyr Lys Gln Phe Cys Val Pro Gly Phe Lys Asn
                20                  25                  30

Asn Lys Gly Val Ala Glu Val Leu Gln Asp Gly Asp Cys Pro Ala Val
            35                  40                  45

Leu Ile Pro Ser Lys Pro Leu Ala Arg Arg Cys Phe Pro Ala Ile His
        50                  55                  60

Ala Tyr Lys Gly Val Leu Met Val Gly Asn Glu Thr Thr Tyr Glu Asp
65                  70                  75                  80

Gly His Gly Ser Arg Lys Asn Ile Thr Asp Leu Val Glu Gly Ala Lys
                85                  90                  95

Lys Ala Asn Gly Val Leu Glu Ala Arg Gln Leu Ala Met Arg Ile Phe
            100                 105                 110

Glu Asp Tyr Thr Val Ser Trp Tyr Trp Ile Ile Gly Leu Val Ile
        115                 120                 125

Ala Met Ala Met Ser Leu Leu Phe Ile Ile Leu Leu Arg Phe Leu Ala
        130                 135                 140

Gly Ile Met Val Trp Val Met Ile Ile Met Val Ile Leu Val Leu Gly
145                 150                 155                 160

Tyr Gly Ile Phe His Cys Tyr Met Glu Tyr Ser Arg Leu Arg Gly Glu
                165                 170                 175

Ala Gly Ser Asp Val Ser Leu Val Asp Leu Gly Phe Gln Thr Asp Phe
            180                 185                 190

Arg Val Tyr Leu His Leu Arg Gln Thr Trp Leu Ala Phe Met Ile Ile
        195                 200                 205

Leu Ser Ile Leu Glu Val Ile Ile Leu Leu Ile Phe Leu Arg
        210                 215                 220

Lys Arg Ile Leu Ile Ala Ile Ala Leu Ile Lys Glu Ala Ser Arg Ala
225                 230                 235                 240

Val Gly Tyr Val Met Cys Ser Leu Leu Tyr Pro Leu Val Thr Phe Phe
                245                 250                 255

Leu Leu Cys Leu Cys Ile Ala Tyr Trp Ala Ser Thr Ala Val Phe Leu
            260                 265                 270

Ser Thr Ser Asn Glu Ala Val Tyr Lys Ile Phe Asp Asp Ser Pro Cys
        275                 280                 285

Pro Phe Thr Ala Lys Thr Cys Asn Pro Glu Thr Phe Pro Ser Ser Asn
        290                 295                 300

Glu Ser Arg Gln Cys Pro Asn Ala Arg Cys Gln Phe Ala Phe Tyr Gly
305                 310                 315                 320

Gly Glu Ser Gly Tyr His Arg Ala Leu Leu Gly Leu Gln Ile Phe Asn
                325                 330                 335

Ala Phe Met Phe Phe Trp Leu Ala Asn Phe Val Leu Ala Leu Gly Gln
            340                 345                 350

Val Thr Leu Ala Gly Ala Phe Ala Ser Tyr Tyr Trp Ala Leu Arg Lys
        355                 360                 365

Pro Asp Asp Leu Pro Ala Phe Pro Leu Phe Ser Ala Phe Gly Arg Ala
        370                 375                 380

Leu Arg Tyr His Thr Gly Ser Leu Ala Phe Gly Ala Leu Ile Leu Ala
385                 390                 395                 400

Ile Val Gln Ile Ile Arg Val Ile Leu Glu Tyr Leu Asp Gln Arg Leu

-continued

```
                405                 410                 415
Lys Ala Ala Glu Asn Lys Phe Ala Lys Cys Leu Met Thr Cys Leu Lys
            420                 425                 430

Cys Cys Phe Trp Cys Leu Glu Lys Phe Ile Lys Phe Leu Asn Arg Asn
        435                 440                 445

Ala Tyr Ile Met Ile Ala Ile Tyr Gly Thr Asn Phe Cys Thr Ser Ala
    450                 455                 460

Arg Asn Ala Phe Phe Leu Leu Met Arg Asn Ile Ile Arg Val Ala Val
465                 470                 475                 480

Leu Asp Lys Val Thr Asp Phe Leu Phe Leu Gly Lys Leu Leu Ile
                485                 490                 495

Val Gly Ser Val Gly Ile Leu Ala Phe Phe Phe Thr His Arg Ile
            500                 505                 510

Arg Ile Val Gln Asp Thr Ala Pro Pro Leu Asn Tyr Tyr Trp Val Pro
        515                 520                 525

Ile Leu Thr Val Ile Val Gly Ser Tyr Leu Ile Ala His Gly Phe Phe
    530                 535                 540

Ser Val Tyr Gly Met Cys Val Asp Thr Leu Phe Leu Cys Phe Leu Glu
545                 550                 555                 560

Asp Leu Glu Arg Asn Asp Gly Ser Ala Glu Arg Pro Tyr Phe Met Ser
                565                 570                 575

Ser Thr Leu Lys Lys Leu Leu Asn Lys Thr Asn Lys Lys Ala Ala Glu
            580                 585                 590

Ser
```

<210> SEQ ID NO 25
<211> LENGTH: 11
<212> TYPE: PRT
<213> ORGANISM: Homo sapiens

<400> SEQUENCE: 25

```
Arg Asp Gly Asp Cys Pro Ala Val Leu Ile Pro
1               5                   10
```

<210> SEQ ID NO 26
<211> LENGTH: 11
<212> TYPE: PRT
<213> ORGANISM: Homo sapiens

<400> SEQUENCE: 26

```
Gln Asp Gly Asp Cys Pro Ala Val Leu Ile Pro
1               5                   10
```

<210> SEQ ID NO 27
<211> LENGTH: 177
<212> TYPE: PRT
<213> ORGANISM: Homo sapiens

<400> SEQUENCE: 27

```
Trp Thr His Gly Asp Pro Arg Lys Val Ile Tyr Pro Thr Asp Ser Arg
1               5                   10                  15

Gly Glu Phe Cys Gly Gln Lys Gly Thr Lys Asn Glu Asn Lys Pro Tyr
            20                  25                  30

Leu Phe Tyr Phe Asn Ile Val Lys Cys Ala Ser Pro Leu Val Leu Leu
        35                  40                  45

Glu Phe Gln Cys Pro Thr Pro Gln Ile Cys Val Glu Lys Cys Pro Asp
    50                  55                  60

Arg Tyr Leu Thr Tyr Leu Asn Ala Arg Ser Ser Arg Asp Phe Glu Tyr
```

```
                     65                  70                  75                  80
Tyr Lys Gln Phe Cys Val Pro Gly Phe Lys Asn Asn Lys Gly Val Ala
                    85                  90                  95

Glu Val Leu Arg Asp Gly Asp Cys Pro Ala Val Leu Ile Pro Ser Lys
                100                 105                 110

Pro Leu Ala Arg Arg Cys Phe Pro Ala Ile His Ala Tyr Lys Gly Val
            115                 120                 125

Leu Met Val Gly Asn Glu Thr Thr Tyr Glu Asp Gly His Gly Ser Arg
        130                 135                 140

Lys Asn Ile Thr Asp Leu Val Glu Gly Ala Lys Lys Ala Asn Gly Val
145                 150                 155                 160

Leu Glu Ala Arg Gln Leu Ala Met Arg Ile Phe Glu Asp Tyr Thr Val
                165                 170                 175

Ser

<210> SEQ ID NO 28
<211> LENGTH: 51
<212> TYPE: PRT
<213> ORGANISM: Homo sapiens

<400> SEQUENCE: 28

Trp Thr His Gly Asp Pro Arg Lys Val Ile Tyr Pro Thr Asp Ser Arg
1               5                  10                  15

Gly Glu Phe Cys Gly Gln Lys Gly Thr Lys Asn Glu Asn Lys Pro Tyr
            20                  25                  30

Leu Phe Tyr Phe Asn Ile Val Lys Cys Ala Ser Pro Leu Val Leu Leu
        35                  40                  45

Glu Phe Gln
    50

<210> SEQ ID NO 29
<211> LENGTH: 49
<212> TYPE: PRT
<213> ORGANISM: Homo sapiens

<400> SEQUENCE: 29

Gln Cys Pro Thr Pro Gln Ile Cys Val Glu Lys Cys Pro Asp Arg Tyr
1               5                  10                  15

Leu Thr Tyr Leu Asn Ala Arg Ser Ser Arg Asp Phe Glu Tyr Tyr Lys
            20                  25                  30

Gln Phe Cys Val Pro Gly Phe Lys Asn Asn Lys Gly Val Ala Glu Val
        35                  40                  45

Leu

<210> SEQ ID NO 30
<211> LENGTH: 46
<212> TYPE: PRT
<213> ORGANISM: Homo sapiens

<400> SEQUENCE: 30

Asp Gly Asp Cys Pro Ala Val Leu Ile Pro Ser Lys Pro Leu Ala Arg
1               5                  10                  15

Arg Cys Phe Pro Ala Ile His Ala Tyr Lys Gly Val Leu Met Val Gly
            20                  25                  30

Asn Glu Thr Thr Tyr Glu Asp Gly His Gly Ser Arg Lys Asn
        35                  40                  45

<210> SEQ ID NO 31
```

```
<211> LENGTH: 42
<212> TYPE: PRT
<213> ORGANISM: Homo sapiens

<400> SEQUENCE: 31

Thr Tyr Glu Asp Gly His Gly Ser Arg Lys Asn Ile Thr Asp Leu Val
1               5                   10                  15

Glu Gly Ala Lys Lys Ala Asn Gly Val Leu Glu Ala Arg Gln Leu Ala
            20                  25                  30

Met Arg Ile Phe Glu Asp Tyr Thr Val Ser
        35                  40

<210> SEQ ID NO 32
<211> LENGTH: 10
<212> TYPE: PRT
<213> ORGANISM: Homo sapiens

<400> SEQUENCE: 32

Ala Glu Val Leu Arg Asp Gly Asp Cys Pro
1               5                   10

<210> SEQ ID NO 33
<211> LENGTH: 24
<212> TYPE: PRT
<213> ORGANISM: Homo sapiens

<400> SEQUENCE: 33

Lys Asn Asn Lys Gly Val Ala Glu Val Leu Arg Asp Gly Asp Cys Pro
1               5                   10                  15

Ala Val Leu Ile Pro Ser Lys Pro
            20

<210> SEQ ID NO 34
<211> LENGTH: 41
<212> TYPE: PRT
<213> ORGANISM: Homo sapiens

<400> SEQUENCE: 34

Tyr Tyr Lys Gln Phe Cys Val Pro Gly Phe Lys Asn Asn Lys Gly Val
1               5                   10                  15

Ala Glu Val Leu Arg Asp Gly Asp Cys Pro Ala Val Leu Ile Pro Ser
            20                  25                  30

Lys Pro Leu Ala Arg Arg Cys Phe Pro
        35                  40

<210> SEQ ID NO 35
<211> LENGTH: 60
<212> TYPE: PRT
<213> ORGANISM: Homo sapiens

<400> SEQUENCE: 35

Leu Asn Ala Arg Ser Ser Arg Asp Phe Glu Tyr Tyr Lys Gln Phe Cys
1               5                   10                  15

Val Pro Gly Phe Lys Asn Asn Lys Gly Val Ala Glu Val Leu Arg Asp
            20                  25                  30

Gly Asp Cys Pro Ala Val Leu Ile Pro Ser Lys Pro Leu Ala Arg Arg
        35                  40                  45

Cys Phe Pro Ala Ile His Ala Tyr Lys Gly Val Leu
    50                  55                  60

<210> SEQ ID NO 36
<211> LENGTH: 81
```

```
<212> TYPE: PRT
<213> ORGANISM: Homo sapiens

<400> SEQUENCE: 36

Glu Lys Cys Pro Asp Arg Tyr Leu Thr Tyr Leu Asn Ala Arg Ser Ser
1               5                   10                  15

Arg Asp Phe Glu Tyr Tyr Lys Gln Phe Cys Val Pro Gly Phe Lys Asn
            20                  25                  30

Asn Lys Gly Val Ala Glu Val Leu Arg Asp Gly Asp Cys Pro Ala Val
        35                  40                  45

Leu Ile Pro Ser Lys Pro Leu Ala Arg Arg Cys Phe Pro Ala Ile His
    50                  55                  60

Ala Tyr Lys Gly Val Leu Met Val Gly Asn Glu Thr Thr Tyr Glu Asp
65                  70                  75                  80

Gly

<210> SEQ ID NO 37
<211> LENGTH: 96
<212> TYPE: PRT
<213> ORGANISM: Homo sapiens

<400> SEQUENCE: 37

Gln Cys Pro Thr Pro Gln Ile Cys Val Glu Lys Cys Pro Asp Arg Tyr
1               5                   10                  15

Leu Thr Tyr Leu Asn Ala Arg Ser Ser Arg Asp Phe Glu Tyr Tyr Lys
            20                  25                  30

Gln Phe Cys Val Pro Gly Phe Lys Asn Asn Lys Gly Val Ala Glu Val
        35                  40                  45

Leu Arg Asp Gly Asp Cys Pro Ala Val Leu Ile Pro Ser Lys Pro Leu
    50                  55                  60

Ala Arg Arg Cys Phe Pro Ala Ile His Ala Tyr Lys Gly Val Leu Met
65                  70                  75                  80

Val Gly Asn Glu Thr Thr Tyr Glu Asp Gly His Gly Ser Arg Lys Asn
            85                  90                  95

<210> SEQ ID NO 38
<211> LENGTH: 121
<212> TYPE: PRT
<213> ORGANISM: Homo sapiens

<400> SEQUENCE: 38

Lys Cys Ala Ser Pro Leu Val Leu Glu Phe Gln Cys Pro Thr Pro
1               5                   10                  15

Gln Ile Cys Val Glu Lys Cys Pro Asp Arg Tyr Leu Thr Tyr Leu Asn
            20                  25                  30

Ala Arg Ser Ser Arg Asp Phe Glu Tyr Tyr Lys Gln Phe Cys Val Pro
        35                  40                  45

Gly Phe Lys Asn Asn Lys Gly Val Ala Glu Val Leu Arg Asp Gly Asp
    50                  55                  60

Cys Pro Ala Val Leu Ile Pro Ser Lys Pro Leu Ala Arg Arg Cys Phe
65                  70                  75                  80

Pro Ala Ile His Ala Tyr Lys Gly Val Leu Met Val Gly Asn Glu Thr
                85                  90                  95

Thr Tyr Glu Asp Gly His Gly Ser Arg Lys Asn Ile Thr Asp Leu Val
            100                 105                 110

Glu Gly Ala Lys Lys Ala Asn Gly Val
            115                 120
```

```
<210> SEQ ID NO 39
<211> LENGTH: 137
<212> TYPE: PRT
<213> ORGANISM: Homo sapiens

<400> SEQUENCE: 39

Lys Pro Tyr Leu Phe Tyr Phe Asn Ile Val Lys Cys Ala Ser Pro Leu
1               5                   10                  15

Val Leu Leu Glu Phe Gln Cys Pro Thr Pro Gln Ile Cys Val Glu Lys
            20                  25                  30

Cys Pro Asp Arg Tyr Leu Thr Tyr Leu Asn Ala Arg Ser Ser Arg Asp
        35                  40                  45

Phe Glu Tyr Tyr Lys Gln Phe Cys Val Pro Gly Phe Lys Asn Asn Lys
    50                  55                  60

Gly Val Ala Glu Val Leu Arg Asp Gly Asp Cys Pro Ala Val Leu Ile
65                  70                  75                  80

Pro Ser Lys Pro Leu Ala Arg Arg Cys Phe Pro Ala Ile His Ala Tyr
                85                  90                  95

Lys Gly Val Leu Met Val Gly Asn Glu Thr Thr Tyr Glu Asp Gly His
            100                 105                 110

Gly Ser Arg Lys Asn Ile Thr Asp Leu Val Glu Gly Ala Lys Lys Ala
        115                 120                 125

Asn Gly Val Leu Glu Ala Arg Gln Leu
    130                 135

<210> SEQ ID NO 40
<211> LENGTH: 121
<212> TYPE: PRT
<213> ORGANISM: Homo sapiens

<400> SEQUENCE: 40

Ile Val Gly Tyr Val Ala Val Gly Ile Ile Ala Trp Thr His Gly Asp
1               5                   10                  15

Pro Arg Lys Val Ile Tyr Pro Thr Asp Ser Arg Gly Glu Phe Cys Gly
            20                  25                  30

Gln Lys Gly Thr Lys Asn Glu Asn Lys Pro Tyr Leu Phe Tyr Phe Asn
        35                  40                  45

Ile Val Lys Cys Ala Ser Pro Leu Val Leu Leu Glu Phe Gln Cys Pro
    50                  55                  60

Thr Pro Gln Ile Cys Val Glu Lys Cys Pro Asp Arg Tyr Leu Thr Tyr
65                  70                  75                  80

Leu Asn Ala Arg Ser Ser Arg Asp Phe Glu Tyr Tyr Lys Gln Phe Cys
                85                  90                  95

Val Pro Gly Phe Lys Asn Asn Lys Gly Val Ala Glu Val Leu Arg Asp
            100                 105                 110

Gly Asp Cys Pro Ala Val Leu Ile Pro
        115                 120

<210> SEQ ID NO 41
<211> LENGTH: 90
<212> TYPE: PRT
<213> ORGANISM: Homo sapiens

<400> SEQUENCE: 41

Gly Gln Lys Gly Thr Lys Asn Glu Asn Lys Pro Tyr Leu Phe Tyr Phe
1               5                   10                  15

Asn Ile Val Lys Cys Ala Ser Pro Leu Val Leu Leu Glu Phe Gln Cys
            20                  25                  30
```

Pro Thr Pro Gln Ile Cys Val Glu Lys Cys Pro Asp Arg Tyr Leu Thr
            35                  40                  45

Tyr Leu Asn Ala Arg Ser Ser Arg Asp Phe Glu Tyr Tyr Lys Gln Phe
 50                  55                  60

Cys Val Pro Gly Phe Lys Asn Asn Lys Gly Val Ala Glu Val Leu Arg
 65                  70                  75                  80

Asp Gly Asp Cys Pro Ala Val Leu Ile Pro
                85                  90

<210> SEQ ID NO 42
<211> LENGTH: 71
<212> TYPE: PRT
<213> ORGANISM: Homo sapiens

<400> SEQUENCE: 42

Lys Cys Ala Ser Pro Leu Val Leu Leu Glu Phe Gln Cys Pro Thr Pro
 1               5                  10                  15

Gln Ile Cys Val Glu Lys Cys Pro Asp Arg Tyr Leu Thr Tyr Leu Asn
            20                  25                  30

Ala Arg Ser Ser Arg Asp Phe Glu Tyr Tyr Lys Gln Phe Cys Val Pro
        35                  40                  45

Gly Phe Lys Asn Asn Lys Gly Val Ala Glu Val Leu Arg Asp Gly Asp
     50                 55                   60

Cys Pro Ala Val Leu Ile Pro
 65                  70

<210> SEQ ID NO 43
<211> LENGTH: 31
<212> TYPE: PRT
<213> ORGANISM: Homo sapiens

<400> SEQUENCE: 43

Tyr Tyr Lys Gln Phe Cys Val Pro Gly Phe Lys Asn Asn Lys Gly Val
 1               5                  10                  15

Ala Glu Val Leu Arg Asp Gly Asp Cys Pro Ala Val Leu Ile Pro
            20                  25                  30

<210> SEQ ID NO 44
<211> LENGTH: 42
<212> TYPE: PRT
<213> ORGANISM: Homo sapiens

<400> SEQUENCE: 44

Gly Phe Lys Asn Asn Lys Gly Val Ala Glu Val Leu Arg Asp Gly Asp
 1               5                  10                  15

Cys Pro Ala Val Leu Ile Pro Ser Lys Pro Leu Ala Arg Arg Cys Phe
            20                  25                  30

Pro Ala Ile His Ala Tyr Lys Gly Val Leu
        35                  40

<210> SEQ ID NO 45
<211> LENGTH: 59
<212> TYPE: PRT
<213> ORGANISM: Homo sapiens

<400> SEQUENCE: 45

Gly Phe Lys Asn Asn Lys Gly Val Ala Glu Val Leu Arg Asp Gly Asp
 1               5                  10                  15

Cys Pro Ala Val Leu Ile Pro Ser Lys Pro Leu Ala Arg Arg Cys Phe
            20                  25                  30

```
Pro Ala Ile His Ala Tyr Lys Gly Val Leu Met Val Gly Asn Glu Thr
            35                  40                  45

Thr Tyr Glu Asp Gly His Gly Ser Arg Lys Asn
    50                  55

<210> SEQ ID NO 46
<211> LENGTH: 81
<212> TYPE: PRT
<213> ORGANISM: Homo sapiens

<400> SEQUENCE: 46

Gly Phe Lys Asn Asn Lys Gly Val Ala Glu Val Leu Arg Asp Gly Asp
1               5                   10                  15

Cys Pro Ala Val Leu Ile Pro Ser Lys Pro Leu Ala Arg Arg Cys Phe
            20                  25                  30

Pro Ala Ile His Ala Tyr Lys Gly Val Leu Met Val Gly Asn Glu Thr
            35                  40                  45

Thr Tyr Glu Asp Gly His Gly Ser Arg Lys Asn Ile Thr Asp Leu Val
    50                  55                  60

Glu Gly Ala Lys Lys Ala Asn Gly Val Leu Glu Ala Arg Gln Leu Ala
65                  70                  75                  80

Met

<210> SEQ ID NO 47
<211> LENGTH: 90
<212> TYPE: PRT
<213> ORGANISM: Homo sapiens

<400> SEQUENCE: 47

Gly Phe Lys Asn Asn Lys Gly Val Ala Glu Val Leu Arg Asp Gly Asp
1               5                   10                  15

Cys Pro Ala Val Leu Ile Pro Ser Lys Pro Leu Ala Arg Arg Cys Phe
            20                  25                  30

Pro Ala Ile His Ala Tyr Lys Gly Val Leu Met Val Gly Asn Glu Thr
            35                  40                  45

Thr Tyr Glu Asp Gly His Gly Ser Arg Lys Asn Ile Thr Asp Leu Val
    50                  55                  60

Glu Gly Ala Lys Lys Ala Asn Gly Val Leu Glu Ala Arg Gln Leu Ala
65                  70                  75                  80

Met Arg Ile Phe Glu Asp Tyr Thr Val Ser
                85                  90

<210> SEQ ID NO 48
<211> LENGTH: 33
<212> TYPE: PRT
<213> ORGANISM: Homo sapiens

<400> SEQUENCE: 48

Asn Asn Lys Gly Val Ala Glu Val Leu Arg Asp Gly Asp Cys Pro Ala
1               5                   10                  15

Val Leu Ile Pro Ser Lys Pro Leu Ala Arg Arg Cys Phe Pro Ala Ile
            20                  25                  30

His

<210> SEQ ID NO 49
<211> LENGTH: 18
<212> TYPE: DNA
<213> ORGANISM: Homo sapiens
<220> FEATURE:
```

```
<221> NAME/KEY: misc_feature
<223> OTHER INFORMATION: HNA-3a

<400> SEQUENCE: 49
agtggctgag gtgcttcg                                                  18

<210> SEQ ID NO 50
<211> LENGTH: 19
<212> TYPE: DNA
<213> ORGANISM: Homo sapiens
<220> FEATURE:
<221> NAME/KEY: misc_feature
<223> OTHER INFORMATION: HNA-3b

<400> SEQUENCE: 50
gagtggctga ggtgcttca                                                 19

<210> SEQ ID NO 51
<211> LENGTH: 21
<212> TYPE: DNA
<213> ORGANISM: Homo sapiens

<400> SEQUENCE: 51
gtgcgccaat atcctcactt g                                              21

<210> SEQ ID NO 52
<211> LENGTH: 25
<212> TYPE: DNA
<213> ORGANISM: Homo sapiens

<400> SEQUENCE: 52
cagtgccttc ccaaccattc cctta                                          25

<210> SEQ ID NO 53
<211> LENGTH: 28
<212> TYPE: DNA
<213> ORGANISM: Homo sapiens

<400> SEQUENCE: 53
atccactcac ggatttctgt tgtgtttc                                       28
```

SCREENING METHODS FOR TRANSFUSION RELATED ACUTE LUNG INJURY (TRALI)

This application claims priority to German Application No. 10 2008 045 696.9 filed Sep. 4, 2008, which is herein incorporated by reference in its entirety.

FIELD OF INVENTION

The invention relates to the identification of the polypeptide sequences of HNA-3a and HNA-3b antigens which are implicated in the occurrence of transfusion related acute lung injury syndrome (TRALI). This invention provides methods and kits for screening for HNA-3a and HNA-3b specific antibodies, HNA-3a and HNA-3b polypeptides, and HNA-3a and HNA-3b nucleic acids in a sample of a biological tissue intended for transplantation or transfusion. The invention also relates to methods and kits for determining whether donor tissues intended for transplant or transfusion will induce TRALI. The invention further provides for methods and kits for determining the susceptibility of a human transplant or transfusion recipient of developing TRALI

BACKGROUND

Antibodies to human neutrophil-specific antigens (HNA) were shown to cause clinical complications such as pulmonary transfusion reactions and in some cases transfusion related acute lung injury (TRALI) (Popovsky et al. *Am. Rev. Resp. Dis.* 128(1): 185-9, 1983) or causing neonatal alloimmune neutropenia (NAIN) (Bux, et al. *Transfus. Med.* 2(2): 143-9, 1992). Therefore, detection of HNA specific antibodies has important clinical applications.

TRALI is a life-threatening transfusion complication and is one of the most frequent causes of transfusion-related death in the United States. TRALI is the second most frequent transfusion-related cause of death in Europe after administration of ABO-incompatible stored blood (Holness et al. *Transfus Med. Rev.* 18: 184-188, 2004). The risk of developing TRALI as a complication of blood transfusion is at least 2000-times higher than contracting an HIV- or hepatitis C infection.

TRALI is defined as a clinical entity consisting of sudden acute shortness of breath within six hours after blood transfusion, connected with bilateral lung infiltrations (lung edema) with no indication of cardiac insufficiency or volume overload (European Haemovigilance Network (EHN). Definitions of Adverse Transfusion Events available on the EHN web site).

TRALI syndrome is difficult to diagnose, because initially it often does not differ from a transfusion-independent lung insufficiency (ALI) or its maximum variant ARDS ("acquired respiratory distress syndrome") (Popovsky & Moore, *Transfusion* 25: 573-577, 1985). Symptoms of TRALI include hypoxemia, tachycardia, hypotension, cyanosis and fever. Often, TRALI is not recognized or misdiagnosed in the clinic because the symptoms are often attributed to other causes, such as fluid overload. TRALI has been associated with the transfusions of all plasma containing blood components, including whole blood, red blood concentrates, fresh frozen plasma, whole blood derived from platelets, pooled platelets, intravenous gamma-globulin, cryoprecipitate, stem cells and granulocytes. TRALI is an injury to the pulmonary microvascular; and therefore, treatment focuses on respiratory support and saline infusion.

TRALI is an immune-related disorder that is primarily associated with antibodies specific for HNA, granulocyte- and human leukocyte antigens (HLA) Class I. Other factors that have induced TRALI in transfusion recipients include biologically active lipids and HLA Class II antibodies. In most cases, antibodies of the donor (in the donor plasma) are transferred with the stored blood and then react with the leucocytes (granulocytes) of the recipient. The binding of the antibodies to the granulocytes leads to their activation and partially to aggregation. Through the subsequent release of the microbicidal arsenal from the granulocytes, the capillary endothelium is damaged which results in lung edema. The immune reaction induces complement-activated granulocytes to release oxygen radicals and proteases that damage the endothelium resulting in the extravasation of protein-rich fluid into the pulmonary alveoli and interstitium. In addition, antibodies within stored blood will bind to and activate granulocytes of the recipient resulting in the expression of adhesion molecules (Uchiyama et al. *Transfus. Med. Rev.* 8: 84-95, 1994), transmigration of granulocytes into the interstitial space between alveolar and vessel endothelium of the lung, and the release of cytokines, proteases and oxygen radicals (Snyder, Immol Invest. 24: 333-9, 1994). These cellular effects cause damage to the capillary walls with subsequent hyperpermeability. A lung edema develops and 10% of the affected patients die from this complication.

In TRALI, recipient antibodies rarely react with the granulocytes of the donor (Bux et al., *Br. J. Heamatol.* 93: 707-713, 1996). However, there have also been cases of TRALI that were induced by antibodies in the transfusion recipient. In very rare cases, anti-IgA-antibodies can also induce TRALI (Saigo et al., *J. Int. Med. Res.* 27: 96-100, 1999).

Blood donations of multiparous women carry particular risk, because an antibody formation against granulocyte- or HLA-antigen of the child can occur during the pregnancies. Likewise, a patient may be immunizing due to an earlier transfusion (Voss et al., *Anaesthesist* 50: 930-932, 2001). Donor plasma that will trigger TRALI cannot be detected clinically. Currently produced erythrocyte concentrates contain very little plasma and only a few granulocytes, therefore TRALI is most likely to occur after administration of fresh plasma and platelet concentrates.

In addition to HLA antibodies, antibodies against three different antigen systems on granulocytes are thought to be responsible for inducing TRALI (Leger et al. *Anesthesiology* 91: 1529-1532, 1999; Davoren et al, *Transfusion* 43: 641-645, 2003; Kopko et al. *JAMA* 287: 1968-1971, 2000; Reil et al. *Vox Sanguinis* (printing, already accessible online), 2008. Two of the antigen systems (HNA-1 and HNA-2) are known with regard to their structure and localization. The antigen HNA-2 was characterized by Prof. Dr. Bux and applied for as a patent (DE 100 28 725 A1). The third antigen system, HNA-3 (consisting of the antithetic antigens HNA-3a and HNA-3b), has not been characterized. The antigen HNA-3a occurs in approximately 95% of the population (Davoren et al, *Transfusion* 43: 641-645, 2003) and is involved particularly frequently in severe courses of TRALI (Reil et al., *Vox Sanguinis* (printing, already accessible online), 2008).

According to the current report by SHOT (Serious Hazards of Transfusion), the British notification and evaluation centre for side-effects in blood transfusions, TRALI is the most frequent cause of a serious side-effect due to transfusion. The report shows a mortality of 9% for the period 1996-2003 (SHOT), Additional cumulative data 1996-2003 is available at the Serious Hazards of Transfusion (SHOT) web site). Since 2001, United States Food and Drug Administration likewise reported TRALI as the main cause of transfusion-associated complications (Goldman et al., Transfus. Med. Rev. 19: 2-31, 2005; Boshkov, Vox Sang. 83: 299-303, 2002).

Currently, most blood and tissue donors have not been HNA typed. The specialized nature of neutrophil immunobiology, the scarcity of HNA typing sera and the need to test fresh neutrophils places restraints on typing HNA compatible blood components. A high percentage of cases of TRALI are caused by blood donated by females, particularly multiparous females, and from the transfusion of fresh frozen plasma. Proposed current solutions for reducing the incidence of TRALI include the exclusion of all females as donors, to exclude multiparous (three or more pregnancies) females as donors, and reducing the transfusion of fresh, frozen plasma.

Currently, the detection of granulocyte-specific antibodies is laborious; and detection of HLA antibodies in the serum of the blood donor is not sufficient. The most reliable determination of a TRALI risk currently consists in a cross-matching between donor serum and patient leucocytes. This test can only be carried out in specialized laboratories (Voss, *Anaesthesist* 50: 930-932, 2001) which are not suitable for donor screening. Other strategies are currently directed to a more restrictive donor management (Mair et al., *Crit. Care Med.* 34: 137-143, 2006) (as described above). This is not acceptable because the exclusion of women from blood donation after a pregnancy leads to a serious reduction in the amount of stored blood.

The exclusion of female donors was investigated systematically in Canada. Through the exclusion of multiparous female donors, 12% of all blood donations would be omitted from the Canadian Blood Service (Goldman et al *Transfus. Med. Rev.* 19: 2-31, 2005). According to some studies, implementing such a strategy would exclude every third potential female donor. (Densmore et al., *Transfusion* 39: 103-106, 1999). An alternative strategy would be the testing of all stored blood for granulocyte-specific antibodies. Currently, this technically cannot be carried out. Other strategies for processing the blood components are proposed, but these strategies would involve new risks such as bacterial contaminations and due to their time requirement are only suitable for planned transfusions, and not for those in emergencies (Mair et al., *Crit. Care Med.* 34: 137-143, 2006). Furthermore, evidence is lacking as to whether such strategies can actually reduce the incidence of TRALI.

Human neutrophil antigens are also known as neutrophil-specific antigens or HNA. Currently there are 5 HNA antigen systems: HNA-1, HNA-2, HNA-3, HNA-4 and HNA-5. Alleles for HNA-1, 2, 4 and 5 were identified and the corresponding glycoproteins were characterized; however, the allele for HNA-3 remains unknown (reviewed by Stroncek, *ASHI Quarterly* 2004). There are three HNA-1 antigens (HNA-1a, HNA-1b and HNA-1c) that are expressed solely on neutrophils and are located on low affinity Fc-γ receptor IIIb. The HNA-2 system has one well established antigen (HNA-2a). HNA-2 is only expressed on neutrophils and neutrophil precursors and is located on the glycoprotein CD177 (NB1 gp). HNA-4 and HNA-5 are located on the β2 integrin. HNA-4 is expressed on granulocytes, monocytes and lymphocytes. (See Stroncek, *ASHI Quarterly* 2004)

The HNA-3 system has one known antigen, HNA-3a, which is also known as 5b. HNA-3 is expressed on neutrophils, lymphocytes, platelets, endothelial cells, kidney, spleen and placenta cells, and is known to be located on a 70 to 95 kDa neutrophil glycoprotein. (See Stroncek, *ASHI Quarterly* 2004). The gene for HNA-3a has not been cloned and the nature and function of glycoprotein was previously unknown. Therefore, current detection of HNA-3 antibody is only based on non-specific assays, such as agglutination tests (Lalezari & Bernard, *Transfusion* 5: 135-42, 1965) or GIFT-FC assay (Davoren et al., *Transfusion* 43(5): 641-5, 2003).

The presumed allele of HNA-3, also known as 5b, has a gene frequency about 0.82 (Van Leeuwen et al. *Vox Sang* 9: 431-46, 1964). It was also reported to have a 0.66 gene frequency (Lalezari & Bernard, Transfusion 5: 135-42, 1965). The protein of 5b was reported to have a molecular weight of 70 to 95 kD (De Haas et al, Transfusion 40(2): 222-7, 2000), yet the 5b gene has not been cloned and the nature and function of the protein remain unknown.

Of interest to the present invention is CTL2 is a 706 amino acid membrane-spanning protein (about 80.152 kD) that comprises 10 helical transmembrane domains. This protein is also known as which is also known as SLC44A2, DKFZp666A071 2, FLJ44586 2 and PP1292 and is known to be involved in choline transport within the inner ear and is expressed on inner ear supporting cells. The gene encoding CTL2 is located on chromosome 19p13. In addition, the antigen, Inner Ear Supporting Cell Antigen (IESCA) is known to be a CTL2 protein which is reactive with an autoantibody associated with autoimmune sensorineural hearing loss (AISNHL).

Currently, the methods of screening and typing transplant tissue or transfusions for HNA antibodies that induce TRALI are inadequate and problematic. In addition, excluding a large portion of the human population from donating blood and tissue is an extreme solution. Therefore, a strong need exists for the development of methods of screening for HNA antigens.

It was therefore an object of the present invention to clarify the protein- or DNA sequences of the human neutrophil antigen-3a or -3b (HNA-3a, HNA-3b) involved in TRALI and to provide the corresponding sequences.

SUMMARY OF INVENTION

The present invention relates to the discovery that HNA-3a is within the amino acids sequence of SEQ ID NO: 1 and HNA-3b is within the amino acid sequence of SEQ ID NO: 3b, and these amino acid sequence are highly similar to that of choline transporter-like protein 2 (CTL2).

A single nucleotide polymorphism (SNP) within codon 154 on an extracellular loop is crucial (SNP rs2288904), as this SNP is the difference between HNA-3a and HNA-3b. The polynucleotide encoding HNA-3a has a "G" (guanine) at position 461 and as a result encodes an "R" (Arginine, Arg) at position 154 of the HNA-3a amino acid sequence, and therefore represents the HNA-3a allele. The polynucleotide encoding HNA-3b has an "A" (adenine) at position 461 and as a result encodes a "Q" (glutamine, Gln) at position 154 of the amino acid sequence, and therefore represents the HNA-3b allele.

It is proposed that the existence of the SNP within codon 154 of the HNA-3 gene results in a portion of the population which may generate alloantibodies to HNA-3a or HNA-3b if exposed to the opposing HNA-3 antigen. This difference allows for portions of the population to have one of two anti-HNA-3 specific antibodies and when exposed to blood or tissue containing a foreign HNA-3 antigen will induce transfusion related acute lung injury (TRALI) in the recipient.

The invention provides for methods of detecting an HNA-3a specific antibody in a biological sample comprising a) obtaining a biological sample, b) contacting the biological sample with a cell transformed or transfected to express the HNA-3a polypeptide of SEQ ID NO: 1 or a fragment thereof to form a complex with HNA-3a in the sample, and c) detecting the complex, wherein the presence of the complex indicates that the biological sample contains HNA-3a specific antibodies.

The preceding methods may be carried out with an antigenic fragment comprising an amino acid sequence selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

The invention also provides for methods of detecting an HNA-3b specific antibody in a biological sample comprising a) obtaining a biological sample, b) contacting the biological sample with a cell transformed or transfected to express the HNA-3b polypeptide of SEQ ID NO: 2 or a fragment thereof to form a complex with HNA-3b in the sample, and detecting the complex, wherein the presence of the complex indicates that the biological sample contains HNA-3b specific antibodies.

The preceding methods may be carried out with an antigenic fragment comprising an amino acid sequence selected from the group consisting of SEQ ID NO: 19, SEQ ID NO: 20, SEQ ID NO: 21, SEQ ID NO: 22, SEQ ID NO: 23, SEQ ID NO: 24 and SEQ ID NO: 26.

The invention contemplates using any cell type including those which do not endogenously express HNA-3a or HNA-3b such as B-cells, CHO cells or insect cells, so that the cell expresses a heterologous HNA-3a or HNA-3 polypeptide. The term "heterologous" refers to cytologic elements, e.g. DNA or protein that are derived from a different species or different cell type.

The invention also contemplates using a cell that expresses low levels of HNA-3a or HNA-3b and increasing expression of the endogenous protein by inserting heterologous promoters or enhancers, or increasing copy number of the HNA-3a or HNA-3b gene. Exemplary cells that may be used include EB-3 cells and K-562 cells.

The invention also provides for methods of detecting an HNA-3a specific antibody in a biological sample comprising a) obtaining a biological sample, b) contacting the biological sample with an aptamer that mimics an antigenic fragment of the HNA-3a polypeptide of SEQ ID NO: 1 to form a complex with the HNA-3a specific antibodies in the sample, and c) detecting the complex, wherein the presence of the complex indicates that the biological sample contains HNA-3a specific antibodies. These methods may be carried out with aptamers that mimic an antigenic fragment comprising an amino acid sequence selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

The invention also provides for methods of detecting an HNA-3a specific antibody in a biological sample comprising a) obtaining a biological sample, b) contacting the biological sample with an aptamer that mimics an antigenic fragment of the HNA-3b polypeptide of SEQ ID NO: 2 to form a complex with the HNA-3b specific antibodies in the sample, and c) detecting the complex, wherein the presence of the complex indicates that the biological sample contains HNA-3b specific antibodies. These methods may be carried out with aptamers that mimic an antigenic fragment comprises an amino acid sequence selected from the group consisting of SEQ ID NO: 19, SEQ ID NO: 20, SEQ ID NO: 21, SEQ ID NO: 22, SEQ ID NO: 23, SEQ ID NO: 24 and SEQ ID NO: 26.

The invention provides for methods of screening for HNA-3a and/or HNA-3b specific antibodies in donor tissue intended for transplants or transfusion in order to determine whether the donor tissue, as a result of the presence of the HNA-3a or HNA-3b specific antibodies, will induce TRALI or graph versus host disease (GVHD) in a human recipient that expresses the HNA-3a or HNA-3b.

In one embodiment, the invention provides for methods of determining whether a donor tissue intended for transplant or transfusion will induce TRALI or GVHD in a human recipient wherein the human recipient expresses the HNA-3a antigen comprising a) obtaining a sample of the tissue intended for transplant or transfusion in the human subject, b) contacting the sample with a polypeptide comprising the amino acid sequence of SEQ ID NO: 1 or an antigenic fragment thereof to form a complex with HNA-3a specific antibodies in the sample, and c) detecting the complex, wherein the presence of the complex indicates that the donor tissue is likely to induce TRALI or GVHD in a human recipient that expresses the HNA-3a antigen. These methods may be carried out the with an antigenic fragment of the HNA-3a amino acid sequence (SEQ ID NO: 1) selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

In another embodiment, the invention provides for methods of determining whether a donor tissue intended for transplant or transfusion will induce TRALI or GVHD in a human recipient wherein the human recipient expresses the HNA-3b antigen comprising a) obtaining a sample of the tissue intended for transplant or transfusion in the human subject, b) contacting the sample with a polypeptide comprising the amino acid sequence of SEQ ID NO: 2 or an antigenic fragment thereof to form a complex with HNA-3b specific antibodies in the sample, and c) detecting the complex, wherein the presence of the complex indicates that the donor tissue is likely to induce TRALI or GVHD in a human recipient that expresses the HNA-3b antigen. These methods may be carried out with antigenic fragments of the HNA-3b amino acid sequence (SEQ ID NO: 2) selected from the group consisting of SEQ ID NO: 19, SEQ ID NO: 20, SEQ ID NO: 21, SEQ ID NO: 22, SEQ ID NO: 23, SEQ ID NO: 24 and SEQ ID NO: 26.

In a further embodiment, the methods of determining whether a donor tissue intended for transplant or transfusion will induce TRALI or GVHD in a human recipient wherein the human recipient expresses the HNA-3a or HNA-3b antigen, wherein in addition to detecting HNA-3a or HNA-3b specific antibodies, the methods further comprise one or more of the following steps: contacting the sample with Fc-γ receptor IIIb polypeptide or an antigenic fragment thereof to form a complex with HNA-1 specific antibodies in the sample, contacting the sample with CD177 polypeptide or an antigenic fragment thereof to form a complex with HNA-2 specific antibodies in the sample, contacting the sample with CD11b polypeptide or an antigenic fragment thereof to form a complex with HNA-4 specific antibodies in the sample, contacting the sample with CD11a polypeptide or an antigenic fragment thereof to form a complex with HNA-5 specific antibodies in the sample, or contacting the sample with an HLA antigen to form a complex with HLA specific antibodies in the sample, and detecting the complex, wherein the presence of any of the complexes indicates that the sample is likely to induce TRALI or GVHD in a human recipient.

The invention also provides for methods of screening a transplant or transfusion recipient for HNA-3a and/or HNA-3b specific antibodies. This screening is of interest because if a donor tissue intended for transplants or transfusion comprises the HNA-3a or HNA-antigen, it is likely that the transplanted or transfused tissue will be rejected if the recipient comprises antibodies to the corresponding antigen. In rejection, the recipients' antibodies will bind to and target the tissue as foreign which will result it destruction by its immune system.

In one embodiment, the invention provides for methods of determining the susceptibility of a human transplant or transfusion recipient for rejecting transplanted or transfused tissue, wherein the donor tissue contains HNA-3a polypeptide or an antigenic fragment thereof, comprising a) obtaining a biological sample from the human transplant or transfusion recipient prior to transplantation or transfusion, b) contacting the biological sample with polypeptide comprising the amino acid sequence of SEQ ID NO: 1 or an antigenic fragment thereof to form a complex with HNA-3a specific antibodies in the biological sample, and c) detecting the complex, wherein the presence of the complex in the biological sample indicates that the human transplant or transfusion recipient is susceptible for rejecting the transplanted or transfused tissue. These methods may be carried out the with an antigenic fragments of the HNA-3a amino acid sequence (SEQ ID NO: 1) selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

In another embodiment, the invention provides for methods of determining the susceptibility of a human transplant or transfusion recipient for rejecting transplanted or transfused tissue, wherein the donor tissue contains HNA-3b polypeptide or an antigenic fragment thereof, comprising a) obtaining a biological sample from the human transplant or transfusion recipient prior to transplantation or transfusion, b) contacting the biological sample with polypeptide comprising the amino acid sequence of SEQ ID NO: 2 or an antigenic fragment thereof to form a complex with HNA-3b specific antibodies in the biological sample, and c) detecting the complex, wherein the presence of the complex in the biological sample indicates that the human transplant or transfusion recipient is susceptible for rejecting the transplanted or transfused tissue. These methods may be carried out with an antigenic fragments of the HNA-3b amino acid sequence (SEQ ID NO: 2) selected from the group consisting of SEQ ID NO: 19, SEQ ID NO: 20, SEQ ID NO: 21, SEQ ID NO: 22, SEQ ID NO: 23, SEQ ID NO: 24 and SEQ ID NO: 26.

In a further embodiment, the invention provides for methods of determining the susceptibility of rejecting transplanted or transfused tissue, wherein the donor tissue contains HNA-3a or HNA-3b polypeptide or an antigenic fragment thereof, wherein in addition to detecting HNA3a or HNA-3b specific antibodies, the methods further comprise one of more of the following steps: contacting the biological sample with Fc-γ receptor IIIb polypeptide or an antigenic fragment thereof to form a complex with HNA-1 specific antibodies in the biological sample, contacting the biological sample with CD177 polypeptide or an antigenic fragment thereof to form a complex with HNA-2 specific antibodies in the biological sample, contacting the biological sample with CD11b polypeptide or an antigenic fragment thereof to form a complex with HNA-4 specific antibodies in the biological sample, contacting the biological sample with CD11a polypeptide or an antigenic fragment thereof to form a complex with HNA-5 specific antibodies in the biological sample, or contacting the biological sample with an HLA antigen to form a complex with HLA specific antibodies in the biological sample, and detecting the complex, wherein the presence of any of the complexes in the biological sample indicates that that the human transplant or transfusion recipient is susceptible for rejecting the transplanted or transfused tissue, wherein the donor tissue contains any of HNA-1, HNA-2, HNA-3a, HNA-3b, HNA-4, HNA-5, and HLA.

Any of the preceding methods may be carried out with aptamers which mimic the HNA-3a or HNA-3b epitope and therefore bind to HNA-3a or HNA-3b specific antibodies.

The invention provides for methods of screening for HNA-3a and/or HNA-3b antigen in donor tissue. Screening for HNA-3a or HNA-3b antigen is important when a transplant or transfusion recipient is known to express HNA-3a or HNA-3b antibodies. The recipient's antibodies may bind to the cells within the donor tissue causing or increasing the risk of rejection of the transplanted or transfused tissue.

In one embodiment, the invention provides for methods of determining whether a donor tissue intended for transplant or transfusion is likely to be rejected in a human recipient wherein the human recipient has HNA-3a specific antibodies, comprising a) obtaining a sample of the tissue intended for transplant or transfusion in the human recipient, b) contacting the sample with an antibody that specifically binds to a HNA-3a polypeptide comprising the amino acid sequence of SEQ ID NO: 1 or a fragment thereof to form a complex with HNA-3a in the sample, and c) detecting the complex, wherein the presence of the complex indicates that the donor tissue is likely to be rejected in a human recipient that expresses HNA-3a specific antibodies.

In another embodiment, the invention provides for methods of determining whether a donor tissue intended for transplant or transfusion is likely to be rejected in a human recipient wherein the human recipient has HNA-3b specific antibodies, comprising a) obtaining a sample of the tissue intended for transplant or transfusion in the human recipient, contacting the sample with an antibody that specifically binds to HNA-3b polypeptide comprising the amino acid sequence of SEQ ID NO: 2 or a fragment thereof to form a complex with HNA-3b in the sample, and detecting the complex, wherein the presence of the complex indicates that the donor tissue is likely to be rejected in a human recipient that expresses HNA-3b specific antibodies.

In a further embodiment, the invention provides for methods of determining whether a donor tissue intended for transplant or transfusion will induce TRALI or GVHD in a human recipient wherein the human recipient has HNA-3a specific antibodies or HNA-3b specific antibodies, wherein in addition to detecting HNA-3a and/or HNA-3b antigen, the method further comprise one or more of the following steps: contacting the sample with an antibody that specifically binds to HNA-1 to form a complex with HNA-1 in the sample, contacting the sample with an antibody that specifically binds to HNA-2 to form a complex with HNA-2 in the sample, contacting the sample with an antibody that specifically binds to HNA-4 to form a complex with HNA-4 in the sample, contacting the sample with an antibody that specifically binds to HNA-5 to form a complex with HNA-5 in the sample, or contacting the sample with an antibody that specifically binds to HLA antigen to form a complex with an HLA in the sample, and detecting the complex, wherein the presence of any of the complexes indicates that the sample is likely to induce TRALI or GVHD in a human recipient.

In any of the foregoing methods, the antibodies may comprise a label selected from the group consisting of a radioactive label, fluorescent label, enzymatic label, avidin label or biotin label. In addition, in any of the above described methods, the antigen-antibody complex may be detected with a secondary antibody. The secondary antibodies may comprise a label selected from the group consisting of a radioactive label, fluorescent label, enzymatic label, avidin label or biotin label.

The invention further provides for methods of genotyping the HNA-3a or HNA-3b allele of a transplant or transfusion donor. The term genotyping refers to detecting the presence of a particular allele, e.g. HNA-3a or HNA-3b, of a human subject. These methods are of interest when the intended transplant or transfusion recipient is known to express HNA-3a or HNA-3b antibodies, and therefore the presence of the HNA-3a or HNA-3b antigen respectively in a transfused or transfected tissue is likely to be rejected by the recipient. The methods of genotyping may employ the oligonucleotide probes that detect the HNA-3a or HNA-3b allele, or PCR to amplify a nucleotide fragment that comprises the HNA-3a or HNA-3b allele or using sequencing methods standard in the art to detect the HNA-3a or HNA-3b allele.

In one embodiment, the invention provides for methods of determining whether a donor tissue intended for transplant or transfusion is likely to be rejected in a human recipient wherein the human recipient expresses HNA-3a specific antibodies, comprising a) obtaining a sample of the tissue intended for transplant or transfusion, b) extracting nucleic acids from the sample, c) contacting the nucleic acids with an oligonucleotide probe that hybridizes to a fragment of SEQ ID NO: 3, and d) detecting hybridization of the probe to the nucleic acids, wherein hybridization of the probe indicates the presence of an HNA-3a nucleic acid and the presence of HNA-3a nucleic acid in the sample indicates that the sample is likely to be rejected in a human recipient that expresses HNA-3a specific antibodies. These methods may be carried out with an oligonucleotide probe that comprises a nucleotide sequence that encodes an amino acid sequence selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

The invention also provide for methods of determining whether a donor tissue intended for transplant or transfusion is likely to be rejected in a human recipient wherein the human recipient expresses HNA-3b specific antibodies, comprising a) obtaining a sample of the tissue intended for transplant or transfusion, b) extracting nucleic acids from the sample, c) contacting the nucleic acids with an oligonucleotide probe that hybridizes to a fragment of SEQ ID NO: 4, and d) detecting hybridization of the probe to the nucleic acids, wherein hybridization of the probe indicates the presence of an HNA-3b nucleic acid and the presence of HNA-3b nucleic acid in the sample indicates that the sample is likely to be rejected in a human recipient that expresses HNA-3b specific antibodies. These methods may be carried out with an oligonucleotide probe that comprises a nucleotide sequence that encodes an amino acid sequence selected from the group consisting of SEQ ID NO: 19, SEQ ID NO: 20, SEQ ID NO: 21, SEQ ID NO: 22, SEQ ID NO: 23, SEQ ID NO: 24 and SEQ ID NO: 26.

In a further embodiment, the methods of determining whether a donor tissue intended for transplant or transfusion is likely to be rejected in a human recipient wherein the human recipient expresses HNA-3a or HNA-3b specific antibodies, wherein in addition to detecting the presence of HNA-3a allele or HNA-3b allele, the methods may comprise one or more of the following steps: contacting the sample with an oligonucleotide probe that hybridizes to a fragment of SEQ ID NO: 5, contacting the sample with an oligonucleotide probe that hybridizes to a fragment of SEQ ID NO: 7, contacting the sample with an oligonucleotide probe that hybridizes to a fragment of SEQ ID NO: 9, contacting the sample with an oligonucleotide probe that hybridizes to a fragment of SEQ ID NO: 11, or contacting the sample with an oligonucleotide probe that hybridizes to a fragment of a nucleotide sequence encoding an HLA antigen, and detecting the hybridization of the probe to the nucleic acids, wherein hybridization of any of the probes indicates the presence of any one of HNA-1, HNA-2, HNA-3a, HNA-3b, HNA-4, HNA-5 or HLA nucleic acid in the sample and the presence of any one of HNA-1, HNA-2, HNA-3a, HNA-3b, HNA-4, HNA-5 or HLA nucleic acid in the sample indicates that the sample is likely to be rejected in a human recipient. For example, the invention contemplates that the fragment of HNA-1 (SEQ ID NO: 5) comprises at least one of nucleotide 141, nucleotide 147, nucleotide 226, nucleotide 227, nucleotide 277 or nucleotide 349 of SEQ ID NO: 5.

In another embodiment, the invention provides for methods of determining the susceptibility of a human transplant or transfusion recipient for developing TRALI or GVHD, wherein the donor tissue contains HNA-3a specific antibodies, comprising a) obtaining a biological sample from the human transplant or transfusion recipient prior to transplantation or transfusion, b) extracting nucleic acids from the biological sample, c) contacting the nucleic acids with an oligonucleotide probe that hybridizes to a fragment of the nucleotide sequence of SEQ ID NO: 1, and d) detecting hybridization of the probe to the nucleic acid, wherein hybridization of the probe to the nucleic acids indicates the presence of HNA-3a nucleic acid in the biological sample and the presence of HNA-3a in the biological sample indicates that a human transfusion or transplant recipient is susceptible for developing TRALI or GVHD. These methods may be carried out with an oligonucleotide probe that comprises a nucleotide sequence that encodes an amino acid sequence selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

The invention also provides for methods of determining the susceptibility of a human transplant or transfusion recipient for developing TRALI or GVHD, wherein the donor tissue contains HNA-3b specific antibodies, comprising a) obtaining a biological sample from the human transplant or transfusion recipient prior to transplantation or transfusion, b) extracting nucleic acids from the biological sample, c) contacting the nucleic acids with a oligonucleotide probe that hybridizes to a fragment of the nucleotide sequence of SEQ ID NO: 2, and d) detecting hybridization of the probe to the nucleic acid, wherein hybridization of the probe to the nucleic acids indicates the presence of HNA-3b nucleic acid in the biological sample and the presence of HNA-3b in the biological sample indicates that a human transfusion or transplant recipient is susceptible for developing TRALI or GVHD. These methods may be carried out with an oligonucleotide probe that comprises a nucleotide sequence that encodes an amino acid sequence selected from the group consisting of SEQ ID NO: 19, SEQ ID NO: 20, SEQ ID NO: 21, SEQ ID NO: 22, SEQ ID NO: 23, SEQ ID NO: 24 and SEQ ID NO: 26.

The invention further provides for methods of determining the susceptibility of a human transplant or transfusion recipient for developing TRALI or GVHD, wherein the donor tissue contains HNA-3a or HNA-3b specific antibodies, wherein in addition to detecting the presence of HNA-3a or HNA-3b allele respectively, the methods may further comprise one or more of the following steps: contacting the sample with an oligonucleotide probe that hybridizes to a fragment of SEQ ID NO: 5, contacting the sample with an oligonucleotide probe that hybridizes to a fragment of SEQ ID NO: 7, contacting the sample with an oligonucleotide probe that hybridizes to a fragment of SEQ ID NO: 9, contacting the sample with an oligonucleotide probe that hybridizes to a fragment of SEQ ID NO: 11, or contacting the sample with an oligonucleotide probe that hybridizes to a fragment of a nucleotide sequence encoding an HLA antigen, and detecting the hybridization of the probe to the nucleic acids, wherein hybridization of any of the probes indicates the presence of any one of HNA-1, HNA-2, HNA-3a, HNA-3b, HNA-4, HNA-5 or HLA nucleic acid in the sample and the presence of any one of HNA-1, HNA-2, HNA-3a, HNA-3b, HNA-4, HNA-5 or HLA nucleic acid in the sample indicates that the sample is likely to induce TRALI or GVHD in a human recipient. For example, the invention contemplates that the fragment of HNA-1 (SEQ ID NO: 5) comprises at least one of nucleotides 141, nucleotide 147, nucleotide 226, nucleotide 227, nucleotide 277 or nucleotide 349 of SEQ ID NO: 5.

In any of the preceding methods, the oligonucleotide probes may be affixed to a substrate selected from the group consisting of membranes, filters, beads and chips. In addition, the invention provides for methods wherein the oligonucleotide probes are in an array. The methods include oligonucleotides probes that comprise a label selected from the group consisting of a radioactive label, fluorescent label, enzymatic label, avidin label or biotin label.

Alternatively, the invention provides for methods of determining whether a donor tissue intended for transplant or transfusion will likely be rejected in a human recipient wherein the human recipient has HNA-3a specific antibodies, comprising a) obtaining a sample from the tissue, b) extracting nucleic acids from the sample, c) amplifying a fragment of HNA-3a nucleic acid of SEQ ID NO: 3 from the extracted nucleic acids using at least one oligonucleotide primer specific for HNA-3a nucleic acid, and d) detecting the fragment of HNA-3a nucleic acid in the sample, wherein the presence of HNA-3a nucleic acid in the sample indicates that the sample is likely to be rejected in a human recipient that has HNA-3a specific antibodies. These methods may be carried out with primers that amplify a fragment of HNA-3a nucleic acid encodes an amino acid sequence selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

The invention also provides for methods of determining whether a donor tissue intended for transplant or transfusion is likely to be rejected in a human recipient wherein the human recipient has HNA-3b specific antibodies, comprising a) obtaining a sample from the tissue, b) extracting nucleic acids from the sample, c) amplifying a fragment of HNA-3b nucleic acid of SEQ ID NO: 4 from the extracted nucleic acids using at least one oligonucleotide primer specific for HNA-3b nucleic acid, and d) detecting the fragment of HNA-3b nucleic acid in the sample, wherein the presence of HNA-3b nucleic acid in the sample indicates that the sample is likely to be rejected in a human recipient that has HNA-3b specific antibodies. These methods may be carried out with at least one primer that amplifies a fragment of HNA-3b nucleic acid that encodes an amino acid sequence selected from the group consisting of SEQ ID NO: 19, SEQ ID NO: 20, SEQ ID NO: 21, SEQ ID NO: 22, SEQ ID NO: 23, SEQ ID NO: 24 and SEQ ID NO: 26.

The invention further provides for methods of determining whether a donor tissue intended for transplant or transfusion will likely be rejected in a human recipient wherein the human recipient has HNA-3a or HNA-3b specific antibodies, in addition to detecting the HNA-3a or HNA-3b allele, the method further comprises one or more of the following steps: amplifying a fragment of HNA-1 nucleic acid (SEQ ID NO: 5) using at least one oligonucleotide primer specific for HNA-1 nucleic acid, amplifying a fragment of HNA-2 nucleic acid (SEQ ID NO: 7) using at least one oligonucleotide primer specific for HNA-2 nucleic acid, amplifying a fragment of HNA-4 nucleic acid (SEQ ID NO: 9) using at least one oligonucleotide primer specific for HNA-4 nucleic acid, amplifying a fragment of HNA-5 nucleic acid (SEQ ID NO: 11) using at least one oligonucleotide primer specific for HNA-5 nucleic acid, or amplifying a fragment of HLA nucleic acid using at least one oligonucleotide primer specific for HLA nucleic acid, and detecting the fragment of any HNA or HLA nucleic acid in the sample, wherein the presence of an HNA or HLA nucleic acid in the sample indicates that the sample is likely to be rejected in a human recipient.

In another embodiment, the invention provides for methods of determining the susceptibility of a human transplant or transfusion recipient for developing TRALI or GVHD wherein the donor tissue contains HNA-3a specific antibodies, comprising a) obtaining a biological sample from the human transplant or transfusion recipient prior to transplantation or transfusion, b) extracting nucleic acids from the biological sample, c) amplifying a fragment of the HNA-3a nucleic acid (SEQ ID NO: 3) from the extracted nucleic acids using at least one oligonucleotide primer specific for HNA-3a nucleic acid in the biological sample, and d) detecting the presence of HNA-3a nucleic acid in the biological sample, wherein the presence of HNA-3a nucleic acid in the biological sample indicates that the human transfusion or transplant recipient is susceptible for developing TRALI or GVHD. These methods may be carried out with primers that amplify a fragment of HNA-3a nucleic acid sequence that encodes an amino acid sequence selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

In another embodiment, the invention provides for methods of determining the susceptibility of a human transplant or transfusion recipient for developing TRALI or GVHD, wherein the donor tissue contains anti-HNA-3b antibodies, comprising a) obtaining a biological sample from the human transplant or transfusion recipient prior to transplantation or transfusion, b) extracting nucleic acids from the biological sample, c) amplifying a fragment of the HNA-3b nucleic acid (SEQ ID NO: 4) from the extracted nucleic acids using at least one oligonucleotide primer specific for HNA-3b nucleic acid, and d) detecting the presence of HNA-3b nucleic acid in the biological sample, wherein the presence of HNA-3b nucleic acid in the biological sample indicates that the human transfusion or transplant recipient is susceptible for developing TRALI or GVHD. These methods may be carried out with primers that amplify a fragment of nucleic acid sequence that encodes an amino acid sequence selected from the group consisting of SEQ ID NO: 19, SEQ ID NO: 20, SEQ ID NO: 21, SEQ ID NO: 22, SEQ ID NO: 23, SEQ ID NO: 24 and SEQ ID NO: 26.

In a further embodiment, the invention provides for methods of determining the susceptibility of a human transplant or transfusion recipient for developing TRALI or GVHD, wherein the donor tissue contains HNA-3a or HNA-3b specific antibodies, in addition to detecting the HNA-3a or HNA-3b allele, the method further comprises one or more of the following steps: amplifying a fragment of HNA-1 nucleic acid (SEQ ID NO: 5) using at least one oligonucleotide primer specific for HNA-1 nucleic acid, amplifying a fragment of HNA-2 nucleic acid (SEQ ID NO: 7) using at least one oligonucleotide primer specific for HNA-2 nucleic acid, amplifying a fragment of HNA-4 nucleic acid (SEQ ID NO: 9) using at least one oligonucleotide primer specific for HNA-4 nucleic acid, amplifying a fragment of HNA-5 nucleic acid (SEQ ID NO: 11) using an oligonucleotide primer specific for HNA-5 nucleic acid, or amplifying a fragment of HLA nucleic acid using at least one oligonucleotide primer specific for HLA nucleic acid, and detecting the fragment of any one of HNA-1, HNA-2, HNA-3a, HNA-3b, HNA-4, HNA-5 or HLA nucleic acid in the sample, wherein the presence of any one of HNA-1, HNA-2, HNA-3a, HNA-3b, HNA-4, HNA-5 or HLA nucleic acid in the sample indicates that the sample is likely to induce TRALI or GVHD in a human recipient.

In any of the preceding methods of the invention, the tissue sample or biological sample is selected from the group consisting of blood, blood derivatives, plasma, serum, cells, and tissues. In particular, the tissue sample or biological sample may be a neutrophil.

The invention also provides for kits for carrying out any of the foregoing methods. In particular, the invention provides for kits for detecting HNA-3a and/or HNA-3b antibodies in conjunction with detecting antibodies specific for one or more of HNA-1, HNA-2, HNA-4, HNA-5 and an HLA. The invention also provides for kits for detecting HNA-3a and/or HNA-3b antigens in conjunction with detecting HNA-1, HNA-2, HNA-4, HNA-5 and an HLA. The invention further provides for methods of detecting an HNA-3a or HNA-3b allele in conjunction with detecting an allele for one or more of HNA-1, HNA-2, HNA-4, HNA-5 and an HLA.

In one embodiment, the invention provides for determining whether a donor tissue intended for transplant or transfusion will induce TRALI or GVHD in a human recipient wherein the human recipient expresses the HNA-3a antigen, wherein the kits comprise a polypeptide comprising the amino acid sequence of SEQ ID NO: 1 or an antigenic fragment thereof, and one or more polypeptides or antigenic fragments thereof selected from the group consisting of Fc-γ receptor IIIb polypeptide, CD 177 polypeptide, CD11b polypeptide, CD11a polypeptide and an HLA antigen. The kit may also comprise a polypeptide comprising the amino acid sequence of SEQ ID NO: 2 or an antigenic fragment thereof for detection of HNA-3b specific antibodies in conjunction with detection of HNA-3a specific antibodies.

The kit may optionally also comprise an antibody specific for HNA-3a and one or more antibodies that specifically bind to a peptide comprising an antigen selected from the group consisting of HNA-1, HNA-2, HNA-4, HNA-5 and HLA. The HNA-3a polypeptide fragment of these kits may comprise an amino acid sequence selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

The invention also provides for kits for determining whether a donor tissue intended for transplant or transfusion is likely to be rejected in a human recipient wherein the human recipient has HNA-3a specific antibodies, wherein the kits comprise an antibody specific for HNA-3a, and one or more antibodies that specifically bind to a peptide comprising an antigen selected from the group consisting of HNA-1, HNA-2, HNA-3b, HNA-4, HNA-5 or HLA.

In addition, the invention provides for kits for determining the susceptibility of a human transplant or transfusion recipient for developing TRALI or GVHD, wherein the donor tissue contains anti-HNA-3a antibodies, wherein the kits comprise an antibody specific for HNA-3a, and one or more antibodies that specifically bind to a peptide comprising an antigen selected from the group consisting of HNA-1, HNA-2, HNA-3b, HNA-4, HNA-5 and HLA.

Any of the preceding kits may further comprise a polypeptide comprising the amino acid sequence of SEQ ID NO: 1 or an antigenic fragment thereof and/or one or more polypeptides or antigenic fragments thereof selected from the group consisting of Fc-γ receptor IIIb polypeptide, CD 177 polypeptide, CD11b polypeptide, CD11a polypeptide and an HLA antigen. The kit may also comprise an antibody specific for HNA-3b for detection of HNA-3b antigen in conjunction with detection of HNA-3a antigen.

The invention also provides for kits for determining whether a donor tissue intended for transplant or transfusion will induce TRALI or GVHD in a human recipient wherein the human recipient expresses the HNA-3b antigen, wherein the kits comprise a polypeptide comprising the amino acid sequence of SEQ ID NO: 2 or an antigenic fragment thereof, and one or more polypeptides or antigenic fragments thereof selected from the group consisting of Fc-γ receptor IIIb polypeptide, CD177 polypeptide, CD11b polypeptide, CD11a polypeptide and an HLA antigen. The kit may also comprise an antibody specific for HNA-3b and/or one or more antibodies that specifically bind to a peptide comprising an antigen selected from the group consisting of HNA-1, HNA-2, HNA-3b, HNA-4, HNA-5 and HLA. In particular, the invention contemplates kits in which the antigenic fragment of the amino acid of SEQ ID NO: 2 are selected from the group consisting of SEQ ID NO: 19, SEQ ID NO: 20, SEQ ID NO: 21, SEQ ID NO: 22, SEQ ID NO: 23, SEQ ID NO: 24 and SEQ ID NO: 26.

The invention also provides for kits for determining whether a donor tissue intended for transplant or transfusion is likely to be rejected in a human recipient wherein the human recipient has HNA-3b specific antibodies, wherein the kit comprises an antibody specific for HNA-3b, and one or more antibodies that specifically bind to a peptide comprising an antigen selected from the group consisting of HNA-1, HNA-2, HNA-3a, HNA-4, HNA-5 and HLA.

In another embodiment, the invention provides for kits for determining the susceptibility of a human transplant or transfusion recipient for developing TRALI or GVHD, wherein the donor tissue contains anti-HNA-3b antibodies, wherein the kits comprise an antibody specific for HNA-3b, and one or more antibodies that specifically bind to a peptide comprising an antigen selected from the group consisting of HNA-1, HNA-2, HNA-3a, HNA-4, HNA-5 and HLA.

These kits may further comprise a polypeptide comprising the amino acid sequence of SEQ ID NO: 2 or an antigenic fragment thereof and/or one or more polypeptides or antigenic fragments thereof selected from the group consisting of Fc-γ receptor IIIb polypeptide, CD177 polypeptide, CD11b polypeptide, CD11a polypeptide and an HLA antigen.

In addition, the preceding kits may comprise a polypeptide comprising the amino acid sequence of SEQ ID NO: 1 or an antigenic fragment thereof for detection of HNA-3a specific antibodies in conjunction with detection of HNA-3b specific antibodies.

Any of the preceding kits may also comprise a secondary antibody. The primary or secondary antibody may comprise a label selected from the group consisting of a radioactive label, fluorescent label, enzymatic label, avidin label or biotin label.

In a further embodiment, the invention provides for kits for determining whether a donor tissue intended for transplant or transfusion is likely to be rejected in a human recipient wherein the human recipient expresses HNA-3a specific antibodies, wherein the kits comprise an oligonucleotide probe that hybridizes to a fragment of the nucleic acid sequence of SEQ ID NO: 3, and one or more oligonucleotide probes that hybridizes to a fragment of a nucleic acid sequence selected from the group consisting of SEQ ID NO: 5, SEQ ID NO: 7, SEQ ID NO: 9, SEQ ID NO: 11, and an HLA nucleotide sequence.

The invention also provides for kits for determining the susceptibility of a human transplant or transfusion recipient for developing TRALI or GVHD, wherein the donor tissue contains anti-HNA-3a antibodies, wherein the kits comprise an oligonucleotide probe that hybridizes to a fragment of the nucleic acid sequence of SEQ ID NO: 3, and one or more oligonucleotide probes that hybridizes to a fragment of a nucleic acid sequence selected from the group consisting of SEQ ID NO: 5, SEQ ID NO: 7, SEQ ID NO: 9, SEQ ID NO: 11, and an HLA nucleotide sequence. The oligonucleotide probes of these kits may comprise a fragment of the nucleotide sequence that encodes an amino acid sequence selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

The invention also provides for kits for determining whether a donor tissue intended for transplant or transfusion is likely to be rejected in a human recipient wherein the human recipient expresses HNA-3b specific antibodies, wherein the kit comprises an oligonucleotide probe that hybridizes to a fragment of the nucleic acid sequence of SEQ ID NO: 4, and one or more oligonucleotide probes that hybridizes to a fragment of a nucleic acid sequence selected from the group consisting of SEQ ID NO: 5, SEQ ID NO: 7, SEQ ID NO: 9, SEQ ID NO: 11, and an HLA nucleotide sequence.

The invention also provides for kits for determining the susceptibility of a human transplant or transfusion recipient for developing TRALI or GVHD, wherein the donor tissue contains anti-HNA-3b antibodies, wherein the kits comprise an oligonucleotide probe that hybridizes to a fragment of the nucleic acid sequence of SEQ ID NO: 4, and one or more oligonucleotide probes that hybridizes to a fragment of a nucleic acid sequence selected from the group consisting of SEQ ID NO: 5, SEQ ID NO: 7, SEQ ID NO: 9, SEQ ID NO: 11, and an HLA nucleotide sequence. The oligonucleotide probes of these kits may comprise a fragment of the nucleotide sequence that encodes an amino acid sequence selected from the group consisting of a nucleotide sequence that encodes an amino acid sequence selected from the group consisting of SEQ ID NO: 19, SEQ ID NO: 20, SEQ ID NO: 21, SEQ ID NO: 22, SEQ ID NO: 23, SEQ ID NO: 24 and SEQ ID NO: 26.

In any of the preceding kits the oligonucleotide probe may comprise a label selected from the group consisting of a radioactive label, fluorescent label, enzymatic label, avidin label and biotin label. In addition, the kits may further comprise buffers for gel loading.

In another embodiment, the invention provides for kits for determining whether a donor tissue intended for transplant or transfusion is likely to be rejected in a human recipient wherein the human recipient expresses HNA-3a specific antibodies, wherein the kits comprise at least one oligonucleotide primer for amplifying a fragment of the HNA-3a nucleic acid of SEQ ID NO: 3, and one or more oligonucleotide primers for amplifying a fragment of a nucleic acid sequence selected from the group consisting of SEQ ID NO: 5, SEQ ID NO: 7, SEQ ID NO: 9, SEQ ID NO: 11, and an HLA nucleotide sequence.

The invention also provides for kits for determining the susceptibility of a human transplant or transfusion recipient for developing TRALI or GVHD, wherein the donor tissue contains anti-HNA-3a antibodies, wherein the kits comprise at least one oligonucleotide primers for amplifying a fragment of the HNA-3a nucleic acid of SEQ ID NO: 3, and one or more oligonucleotide primers for amplifying a fragment of a nucleic acid sequence selected from the group consisting of SEQ ID NO: 5, SEQ ID NO: 7, SEQ ID NO: 9, SEQ ID NO: 11, and an HLA nucleotide sequence. These primers may amplify a fragment of HNA-3a nucleic acid which encodes an amino acid sequence selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

The preceding kits may further comprise a fragment of the HNA-3a nucleic acid that is amplified by the oligonucleotide primers and/or one or more fragments of a nucleic acid sequence selected from the group consisting of SEQ ID NO: 5, SEQ NO: ID: 7, SEQ ID NO: 9, SEQ ID NO: 11, and an HLA nucleotide sequence that is amplified by the oligonucleotide primers. In addition, the kits may further comprise oligonucleotide primers for amplifying a fragment of the HNA-3b nucleic acid of SEQ ID NO: 4 in conjunction with the amplification of a fragment of HNA-3a.

In another embodiment, the invention provides for kits for determining whether a donor tissue intended for transplant or transfusion is likely to be rejected in a human recipient wherein the human recipient expresses HNA-3b specific antibodies, wherein the kit comprises at least one oligonucleotide primer for amplifying a fragment of the HNA-3b nucleic acid of SEQ ID NO: 4, and one or more oligonucleotide primers for amplifying a fragment of a nucleic acid sequence selected from the group consisting of SEQ ID NO: 5, SEQ ID NO: 7, SEQ ID NO: 9, SEQ ID NO: 11, and an HLA nucleotide sequence.

The invention also provides for kits for determining the susceptibility of a human transplant or transfusion recipient for developing TRALI or GVHD, wherein the donor tissue contains anti-HNA-3b antibodies, wherein the kit comprises at least one oligonucleotide primer for amplifying a fragment of the HNA-3b nucleic acid of SEQ ID NO: 4, and at least one oligonucleotide primer for amplifying a fragment of a nucleic acid sequence selected from the group consisting of SEQ ID NO: 5, SEQ ID NO: 7, SEQ ID NO: 9, SEQ ID NO: 11, and an HLA nucleotide sequence. These primers may amplify a fragment of HNA-3a nucleic acid which encodes an amino acid sequence selected from the group consisting of SEQ ID NO: 19, SEQ ID NO: 20, SEQ ID NO: 21, SEQ ID NO: 22, SEQ ID NO: 23, SEQ ID NO: 24 and SEQ ID NO: 26.

Any of the preceding kits may also comprise buffers for PCR amplification, dNTP's and buffers for gel loading.

In another embodiment, the invention provides for an isolated HNA-3b polypeptides such as isolated polypeptides comprising the amino acid sequence SEQ ID NO: 2, isolated polypeptide comprising a fragment of the polypeptide of SEQ ID NO: 2 wherein the fragment is at least 7 amino acids in length, at least 10 amino acids in length, at least 20 amino acids in length or at least 50 amino acids in length. The fragments of HNA-3b include a fragment comprising amino acid residue 154 of SEQ ID NO: 2, wherein residue 154 is glutamine (Gln). The fragments of HNA-3b polypeptide include fragments comprising the amino acid sequence of SEQ ID NO: 19, SEQ ID NO: 20, SEQ ID NO: 21, SEQ ID NO: 22, SEQ ID NO: 23, SEQ ID NO: 24 and SEQ ID NO: 26 and reacts with or specifically binds to HNA-3b-specific alloantibodies. The invention also provides of polynucleotides encoding the HNA-3b polypeptides.

The invention provides for fragments of the HNA-3a polypeptide of SEQ ID NO: 1, such as an isolated polypeptide comprising the amino acid sequence of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42, wherein the polypeptide reacts with or specifically binds to HNA-3a-specific alloantibodies. The invention also provides for polynucleotides encoding these HNA-3a polypeptide fragments.

In another embodiment, the invention provides for use of a HNA-3a polypeptide or fragment thereof for identification of HNA-3a-specific alloantibodies. Use of a HNA-3b polypeptide or fragment thereof for identification of HNA-3b-specific alloantibodies is also provided.

The invention further provides for a use of a polynucleotide encoding an HNA-3a polypeptide or a fragment thereof which encodes a protein that reacts with or specifically binds to HNA-3a-specific alloantibodies, for determination of the HNA-3a genotype. In addition, the invention provides for use of a HNA-3b polynucleotide or a fragment thereof for determination of the HNA-3b genotype. For example, the invention provides for use of a fragment of SEQ ID NO: 4 comprising codon 154 for determination of the HNA-3b genotype.

In a further embodiment, the invention provides for use of a protein comprising an amino acid sequence of SEQ ID NO: 1 or a fragment thereof which reacts with HNA-3a-specific alloantibodies, or a HNA-3a protein fragment in the analysis of blood samples or blood plasma for identification of antibodies against the HNA-3a antigen.

The invention also provides for use of a HNA-3b polypeptide in the analysis of blood samples or blood plasma for identification of antibodies against the HNA-3b antigen.

Use of a polypeptide comprising an amino acid sequence of SEQ ID NO: 1 (HNA-3a) or a fragment thereof or an amino acid of SEQ ID NO: 2 (HNA-3b) or a fragment thereof in a process, which uses the protein or the protein fragment to separate antibodies from blood samples or blood plasma.

Use of a polypeptide comprising an amino acid sequence of SEQ ID NO: 1 (HNA-3a) or a fragment thereof or a polypeptide of SEQ ID NO: 2 (HNA-3b) or a fragment thereof in a process, which uses the protein or the protein fragment to produce antibodies, preferably monoclonal antibodies. In a further embodiment, the invention provides for methods of screening for HNA-3b genotype in a human subject comprising a) obtaining a biological sample from the human subject, b) extracting nucleic acids from the biological sample, and b) detecting a fragment of a nucleic acid sequence of SEQ ID NO: 4 in the biological sample, wherein the fragment comprises codon 154 of SEQ ID NO: 4, wherein the detection of codon 154 of SEQ ID NO: 4 indicates that the human subject has the HNA-3b genotype. The detecting step may include contacting the nucleic acid with an oligonucleotide probe that hybridizes to a fragment of the nucleic acid sequence of SEQ ID NO: 4 or amplifying a fragment of SEQ ID NO: 4 from the extracted nucleic acid using at least one oligonucleotide primer specific for a fragment of SEQ ID NO: 4. For the method of screening for HNA-3b genotype, the biological sample that is used may be selected from the group consisting of blood, blood derivatives, plasma, serum, cells, and tissues.

SEQUENCES OF THE INVENTION

SEQ ID NO: 1—human HNA-3a protein
SEQ ID NO: 2—human HNA-3b protein
SEQ ID NO: 3—human HNA-3a DNA
SEQ ID NO: 4—human HNA-3b DNA
SEQ ID NO: 5—human FCγ receptor IIIb DNA (HNA-1)
SEQ ID NO: 6—human FCγ receptor IIIb protein (HNA-1)
SEQ ID NO: 7—human CD177 DNA (HNA-2)
SEQ ID NO: 8—human CD177 protein (HNA-2)
SEQ ID NO: 9—human CD11b DNA (HNA-4)
SEQ ID NO: 10—human CD11b protein (HNA-4)
SEQ ID NO: 11—human CD11a DNA (HNA-5)
SEQ ID NO: 12—human CD11a protein (HNA-5)
SEQ ID NO: 13—amino acids 1-231 of HNA-3a (SEQ ID NO: 1)
SEQ ID NO: 14—amino acids 55-183 of HNA-3a (SEQ ID NO: 1)
SEQ ID NO: 15—amino acids 55-164 of HNA-3a (SEQ ID NO: 1)
SEQ ID NO: 16—amino acids 114-164 of HNA-3a (SEQ ID NO: 1)
SEQ ID NO: 17—amino acids 55-706 of HNA-3a (SEQ ID NO: 1)
SEQ ID NO: 18—amino acids 114-706 of HNA-3a (SEQ ID NO: 1)
SEQ ID NO: 19—amino acids 1-231 of HNA-3b (SEQ ID NO: 2)
SEQ ID NO: 20—amino acids 55-183 of HNA-3b (SEQ ID NO: 2)
SEQ ID NO: 21—amino acids 55-164 of HNA-3b (SEQ ID NO: 2)
SEQ ID NO: 22—amino acids 114-164 of HNA-3b (SEQ ID NO: 2)
SEQ ID NO: 23—amino acids 55-706 of HNA-3b (SEQ ID NO: 2)
SEQ ID NO: 24—amino acids 114-706 of HNA-3B (SEQ ID NO: 2)
SEQ ID NO: 25—amino acids 154-164 of HNA-3a (SEQ ID NO: 1)
SEQ ID NO: 26—amino acids 154-164 of HNA-3b (SEQ ID NO: 2)
SEQ ID NOS: 27-47—fragments of HNA-3a in Table 1
SEQ ID NO: 48—amino acids 145-167 of HNA-3a (SEQ ID NO: 1)
SEQ ID NOS: 49-55—primer sequences

DETAILED DESCRIPTION

The present invention is based on the discovery that HNA-3 is located on the CTL2 transmembrane protein. A serum sample that was known to induce TRALI in transfusion recipients, but was negative for HNA-1 and HNA-2 antibodies, was used to identify the source of HNA-3a antigen. HNA-3a was identified by first comparing the HNA-3a positive and negative cell surface proteins that were immunoprecipitated by HNA-3a sera. The cells were characterized with HNA-3a positive and negative sera by flow cytometry. The HNA positive and negative granulocytes were then incubated with HNA-3a positive sera and the cell surface proteins that reacted with the sera were immunoprecipitated with Protein-G coated magnetic beads as described in detail in Example 6. The protein profiles were first analyzed using SDS-PAGE and two identified proteins having a molecular weight of about 80-100 kD were only present in the positive cells, not in the negative cells. Those proteins were excised from the SDS gel and further analyzed with mass spectrometry (MS) analysis and confirmed by sequencing the amino acid sequence.

The invention provides for methods of screening biological samples to detect antibodies specific for HNA-3a or HNA-3b antigen. The biological sample includes whole blood, blood derivatives, red blood cell concentrates, plasma, serum, fresh frozen plasma, whole blood derived platelet concentrates, apheresis platelets, pooled platelets, intravenous gamma-globulin, cryoprecipitate, cerebrospinal fluid, tissues and cells such as stem cells, neutrophils and granulocytes. The biological samples may be obtained from a human donor of tissue or cells intended for transplantation or a human donor of blood or blood derivatives intended for transfusion. The biological samples may be obtained from tissues or cells that are intended for transplantation in a human recipient. In addition, the biological sample may be obtained from blood or blood derivatives that are intended for transfusion in a human recipient. The biological sample may also be obtained from a human subject that is an intended recipient of a transplant or transfusion.

The invention also relates to screening for susceptibility or determining if the recipient will develop graft versus host disease (GVHD). GVHD is when a tissue comprises immunologically competent cells or antibodies that attack the recipient. The leading cause of GVHD is hematopoietic cell transplantation, both allogeneic (between 2 individuals) and autologous (from the same individual). Solid organ transplants, blood transfusions, and maternal-fetal transfusions also reportedly cause GVHD. Acute symptoms of GVHD include abdominal pain or damage, diarrhea, fever, jaundice, skin rash, vomiting and weight loss. Chronic symptoms of GVHD include dry eyes, dry mouth, hepatitis, lung and digestive tract disorders and skin rash.

The invention also relates to methods and products related to determining if a transplanted or transfused tissue is likely to be rejected by the recipient. Symptoms of rejection include indications that the transplanted organ does not function properly, general discomfort, uneasiness, or ill feeling, pain or swelling in the location of the organ and fever.

Identification of HNA-3a and HNA-3b

It was therefore an object of the present invention to identify and provide the protein and DNA sequences of the human neutrophil antigen-3a or -3b (HNA-3a, HNA-3b) involved in TRALI.

In other words, the problem was solved by the provision of the protein (HNA-3a antigen), consisting of an amino acid sequence SEQ ID NO: 1, which reacts with alloantibodies which are specific for HNA-3a, and by the provision of the protein (HNA-3b antigen), consisting of an amino acid sequence SEQ ID NO: 2, which reacts with alloantibodies which are specific for HNA-3b.

Subjects coming into question were investigated for the identification of HNA-3a-positive and -negative subjects, whose cells can be used for further investigations. Antibodies from donors whose blood products have triggered TRALI, and the white blood cells on the surfaces of which the corresponding antigens are expressed were used. After the identification of subjects with high-titer HNA-3a antibodies, with which the antigen can be precipitated, the donors were subjected to a plasmapheresis, in order to obtain sufficient material for the antigen-antibody reactions. The antigens were precipitated by means of the antibodies and the still unknown protein/gene structures of HNA-3a were characterized.

In detail, firstly an optimization of the preparation of granulocytes was developed. Then, by means of a screening program, HNA-3a-positive and -negative subjects were determined, whose cells were able to be used for further investigations. Subjects were then selected with high-titer HNA-3a antibodies, with which the antigen was able to be precipitated. A plasmapheresis of the selected subjects was carried out in order to obtain sufficient material for the antigen-antibody reactions. The method for the preparation of granulocyte membrane proteins for a quantitative gel electrophoresis was first developed with platelets, because these have no nucleus and the preparation was therefore simplified. The method was then transferred and adapted to leucocytes/granulocytes containing a nucleus. This made possible an optimization of the preparation of granulocyte membrane proteins. The corresponding proteins were analyzed by means of analytical methods. The enrichment/isolation of HNA-3a from the prepared membrane proteins was carried out by means of immunoprecipitation, and confirmed by Western blotting. The protein which carries HNA-3a was identified by mass spectrometry; and subsequently, the primary sequence of HNA-3a was identified by sequence analysis (SEQ ID NO: 1).

The invention therefore concerns a protein (HNA-3a antigen), consisting of an amino acid sequence SEQ ID NO: 1, which reacts with alloantibodies which are HNA-3a-specific. Additionally included are also proteins (HNA-3a antigens) consisting of an amino acid sequence SEQ ID NO: 1, in which one or more amino acids have been removed, added or replaced and which react with alloantibodies which are HNA-3a specific. The identified HNA-3a antigen proved to be a variant of the transmembrane receptor CTL2. This has a molecular weight in the range 80 to 100 kDa, and deglycosylation shifted the band to 64 kDa in the Western blot.

The HNA-3 antigen is expressed on the CTL2 protein on granulocytes and lymphocytes. A single nucleotide polymorphism (SNP) on an extracellular loop is crucial (SNP rs2288904), as this SNP is the difference between HNA-3a and HNA-3b. This SNP allows for genotyping of blood donors in relation to their HNA-3a/HNA-3b status. The polynucleotide encoding HNA-3a has a "G" (guanine) at position 461 and as a result encodes an "R" (Arginine, Arg) at position 154 of the HNA-3a amino acid sequence, and therefore represents the HNA-3a allele. The polynucleotide encoding HNA-3b has an "A" (adenine) at position 461 and as a result encodes a "Q" (glutamine, Gln) at position 154 of the amino acid sequence, and therefore represents the HNA-3b allele.

The primary sequence of the HNA-3b antigen was determined through amino acid exchange at position 154 arginine (Arg, R) to glutamine (Gln, Q) (see SEQ ID NO: 2). Accordingly, the invention concerns a protein (HNA-3b antigen)

consisting of an amino acid sequence of SEQ ID NO: 2, which reacts with HNA-3b specific alloantibodies. Likewise, the invention includes HNA-3b proteins consisting of an amino acid sequence of SEQ ID NO: 2, in which one or more amino acids have been removed, added or replaced and which react with HNA-3b specific alloantibodies.

Likewise, the invention provides for proteins, both with respect to the HNA-3a and also to the HNA-3b, which are protein fragments with a chain length of at least 7, at least 10 amino acids, at least 20 amino acids, or at least 50 amino acids.

Subsequently, the HNA-3a gene was isolated and heterologously expressed. The corresponding DNA sequences for HNA-3a correspond to the sequence set out as the nucleotide sequence SEQ ID NO: 3 and all sequences hybridizing therewith, which codes an HNA-3a antigen described above, which reacts with or binds to HNA-3a specific alloantibodies. The invention also includes a nucleotide sequence which has an identity on the nucleotide level of at least 90%, preferably at least 95%, most preferably at least 98% to SEQ ID NO: 3 and all sequences hybridizing therewith, which codes an HNA-3a antigen described above, and which reacts with or binds to HNA-3a specific alloantibodies.

Additionally, the invention provides for splice variants of a nucleotide sequence SEQ ID NO: 3, which are at least 70% identical to the nucleotide sequence SEQ ID NO: 3. Preferably, the sequence identity is at least 80%, more preferably 90% and most preferably 95% to SEQ ID NO: 3.

The invention further provides for a nucleotide sequence SEQ ID NO: 4 and all sequences hybridizing therewith, which codes the HNA-3b antigen described above, which reacts with HNA-3b specific alloantibodies. This also includes a nucleotide sequence which has an identity on the nucleotide level of at least 90%, preferably at least 95%, most preferably at least 98% and all sequences hybridizing therewith which codes a HNA-3b antigen described above, and which reacts with alloantibodies which are HNA-3b specific. Exemplary stringent hybridization conditions comprise hybridization at 65° C. and washing three times for 15 minutes with 0.25×SSC, 0.1% SDS at 65° C. Additional exemplary stringent hybridization conditions comprise hybridization in 0.02 M to 0.15 M NaCl at temperatures of about 50° C. to 70° C. or 0.5×SSC 0.25% SDS at 65° for 15 minutes, followed by a wash at 65° C. for a half hour or hybridization at 65° C. for 14 hours followed by 3 washings with 0.5×SSC, 1% SDS at 65° C.

Additionally, the invention provides for splice variants of a nucleotide sequence of SEQ ID NO: 4, which are at least 70% identical to the nucleotide sequence SEQ ID NO: 4. Preferably, the sequence identity is at least 80%, more preferably 90% and most preferably 95%.

Sequence identity or identity on the nucleotide level generally means 100% identity.

Based on the determined primary structures, the method for recombinant production of the antigen was optimized on the basis of the already known proteins/antigens HNA-1a, -1b, -1c, -2a. The results obtained for the HNA-1 and HNA-2 antigens were transferred to HNA-3a or HNA-3b, so that these antigens would be produced in a suitable expression system such as expression in *Escherichia coli*, in eukaryotic cells, in insect cells.

The present invention accordingly contains the use of a protein (HNA-3a antigen) consisting of an amino acid sequence of SEQ ID NO: 1 for the identification of HNA-3a specific alloantibodies. Likewise included in the invention is the use of a protein (HNA-3b antigen) consisting of an amino acid sequence of SEQ ID NO: 2 for the identification of HNA-3b specific alloantibodies.

In addition, the present invention includes the use of a nucleotide sequence of SEQ ID NO: 3 for determining the HNA-3a genotype, and the use of a nucleotide sequence of SEQ ID NO: 4 for determining the HNA-3b genotype.

The methods of the present invention may be carried out using ELISA assays, flow cytometry, immunofluorescence methods, electro-chip assays, PCRs and agglutination tests.

Likewise, the invention provides for a test system for determining HNA-3a specific alloantibodies, which bind to a protein (HNA-3a antigen) consisting of an amino acid sequence of SEQ ID NO: 1. The invention also provides for a test system for determining HNA-3b specific alloantibodies, which bind to a protein (HNA-3b antigen) consisting of an amino acid sequence of SEQ ID NO: 2.

The invention also provides for a test system for determining the HNA-3a genotype, which comprises a nucleotide sequence of SEQ ID NO: 3 and for a test system for determining the HNA-3b genotype which comprises a nucleotide sequence of SEQ ID NO: 4.

According to the invention, the protein (HNA-3a antigen), consisting of an amino acid sequence of SEQ ID NO: 1, is used in the analysis of blood samples or blood plasma for the identification of antibodies that specifically bind to HNA-3a antigen. Likewise, the protein (HNA-3b antigen), consisting of an amino acid sequence SEQ ID NO: 2 is used in the analysis of blood samples or blood plasma for the identification of antibodies against the HNA-3b antigen.

The invention further comprises the use of a protein (HNA-3a antigen) consisting of an amino acid sequence of SEQ ID NO: 1 in a method which uses the antigen in order to separate antibodies from blood samples or blood plasma. The invention likewise comprises the use of a protein (HNA-3b antigen) consisting of an amino acid sequence of SEQ ID NO: 2 as described above in a method which uses the antigen in order to separate antibodies from blood samples or blood plasma. Particularly preferred is the use of the protein in adsorption methods such as plasmapheresis.

The invention further provides for the use of a protein (HNA-3a antigen) consisting of an amino acid sequence of SEQ ID NO: 1 in a method which uses the antigen in order to produce antibodies, preferably monoclonal antibodies. Likewise the invention provides for the use of a protein (HNA-3b antigen) consisting of an amino acid sequence of SEQ ID NO: 2 in a method which uses the antigen in order to produce antibodies, preferably monoclonal antibodies.

Antigenic Fragments of HNA-3a

Epitope mapping of antigenic fragments of HNA-3a or HNA-3b, that generate HNA-3a or HNA-3b specific antibodies, may be identified using methods standard in the art such as site-specific mutagenesis, genetic engineering, analysis of CTL2 peptide libraries, predictive algorithms, functional assays, such as ELISpot or intracellular cytokine staining, and cellular binding assays. High throughput systems for analysis of peptide libraries are commercially available, such as the REVEAL & ProVE™ System (Proimmune, Springfield. VA).

Preferred protein fragments of HNA-3a (SEQ ID NO: 1) include at least the amino acid sequence of SEQ ID NO: 13 (amino acids 1-231 of SEQ ID NO: 1), at least the amino acid sequence of SEQ ID NO: 14 (amino acids 55-183 of SEQ ID NO: 1), at least the amino acid sequence of SEQ ID NO: 15 (amino acids 55-164 of SEQ ID NO: 1), at least the amino acid sequence of SEQ ID NO: 16 (amino acids 114-164 of SEQ ID NO: 1), at least the amino acid sequence of SEQ ID NO: 25 (amino acids 154-164 of SEQ ID NO: 1), at least the amino acid sequence of SEQ ID NO: 17 (amino acids 55-706 of SEQ ID NO: 1), and at least the amino acid sequence of SEQ ID NO: 18 (amino acids 114-706 of SEQ ID NO: 1) which would react with or bind to HNA-3a-specific antibodies such as alloantibodies.

Furthermore, the invention relates to any protein fragment consisting of amino acid sequence of SEQ ID NO: 1 as described herein in which one or more amino acids has been removed, added or have been replaced and which reacts with or binds to HNA-3a-specific antibodies or alloantibodies.

The present invention relates to protein fragments of the amino acid sequence of SEQ ID NO: 2. Preferred protein fragments of HNA-3b (SEQ ID NO: 2) include at least the amino acid sequence of SEQ ID NO: 19 (amino acids 1-231 of SEQ ID NO: 2), at least the amino acid sequence of SEQ ID NO: 20 (amino acids 55-183 of SEQ ID NO: 2), at least the amino acid sequence of SEQ ID NO: 21 (amino acids 55-164 of SEQ ID NO: 2), at least the amino acid sequence of the SEQ ID NO: 22 (amino acids 114-164 of SEQ ID NO: 2), at least the amino acids of SEQ ID NO: 26 (amino acids 154-164 of SEQ ID NO: 2), at least the amino acids of SEQ ID NO: 23 (amino acids 55-706 of SEQ ID NO: 2) and at least the amino acids of SEQ ID NO: 24 (amino acids 114-706 of SEQ ID NO: 2), which react with or bind to the HNA-3b specific antibodies such as alloantibodies.

Likewise, the invention relates to protein fragments consisting of an amino acid sequence of SEQ ID NO: 2, as described above, in which one or more amino acids has been removed, added or replaced and which reacts with or binds to the HNA-3b specific antibodies or alloantibodies.

Method of Detecting HNA-3 Specific Antibodies

The invention provides for methods of detecting HNA-3a or HNA-3b specific antibodies in a biological sample. The invention also contemplates detecting other antibodies such as antibodies specific for HNA-1, HNA-2 or HLA in combination with detecting HNA-3a or HNA-3b specific antibodies. Methods of detecting of antibody include non-specific and specific assays such as, granulocyte immunofluorescence test, granulocyte immunofluorescence flow cytometry assay (GIFT-FC), monoclonal antibody immobilization of granulocyte antigens (MAIGA) assay, single radial immunodiffusion assay (SRID), enzyme immunoassay and hemagglutination inhibition assay (HAI).

An exemplary non-specific assay uses intact granulocytes as a target, e.g. GIFT-FC uses a panel of neutrophils with different HNAs (Davoren, et al. Transfusion 43(5): 641-5, 2003, Kobayashi et al, *Ped. Res.* 26: 246-249). The neutrophils are first incubated with test sera followed by incubation with a fluorescently labeled secondary antibody, such as anti-human polyvalent immunoglobulin, IgG, IgM and IgA. After washing, the antibody binding to the cell suspensions is examined by flow cytometry.

An exemplary specific assay uses immobilized HNA glycoprotein as a target, e.g. MAIGA assay. MAIGA is an ELISA-based test that uses HNA-3 specific monoclonal antibodies to capture the neutrophil antigens within test sera. Subsequently, the cell mixtures are incubated with an enzyme labeled secondary antibody, such as anti-mouse IgG, and binding is detected with a colorimetric assay (Bux, et al. Transfusion Med. 3(2): 157-62, 1993, Metcalfe &Waters, Transfusion Med. 2:283-287, 1992.)

ELISA assay is used to determine total antibodies in the sample. The immunogen, e.g. the HNA-3a polypeptide of SEQ ID NO: 1, the HNA-3b polypeptide of SEQ ID NO: 2 or antigenic fragments thereof, is adsorbed to the surface of a microtiter plate. The test serum is exposed to the plate followed by an enzyme linked immunoglobulin, such as IgG.

The enzyme activity adherent to the plate is quantified by any convenient means such as spectrophotometers and is proportional to the concentration of antibody directed against the immunogen present in the test sample. In addition, HNA-3a or HNA-3b polypeptide or antigenic fragments thereof may be attached to solid substrates such as membranes, beads, filters, glass, silicon, metal, metal-alloy, anopore, polymeric, nylon or plastic for detection of antibodies specific for HNA-3a or HNA-3b.

The SRID assay utilizes a layer of a gel, such as agarose, containing the antigen being tested. A well is cut in the gel and the test sera are placed in the well. Diffusion of the antibody out into the gel leads to the formation of a precipitation ring whose area is proportional to the concentration of the antibody in the serum being tested.

HAI utilizes the capability of an immunogen to agglutinate chicken red blood cells (or the like). The assay detects neutralizing antibodies, i.e., those antibodies able to inhibit hemagglutination. Dilutions of the test serum are incubated with a standard concentration of immunogen, followed by the addition of the red blood cells. The presence of neutralizing antibodies will inhibit the agglutination of the red blood cells by the immunogen.

Additional assays to detect circulating anti-HNA-3a or anti-HNA-3b antibody in the serum of the transplant or transfusion patient may be used. In such an assay, serum is screened for the presence of anti-HNA-3a or HNA-3b antibodies through detection of complement-mediated lytic activity. Serum is screened for complement-mediated lytic activity against T and B lymphocytes from a panel of individuals representing the most frequently encountered HNA-3a or HNA-3b antigens. The assay is performed in the presence or absence of dithioerythritol.

The methods of detecting an HNA-3a or HNA-3b antibodies of the invention may be carried out with neutrophils or any cell type transformed or transfected to express HNA-3a or HNA-3b. The methods may be carried out will cells that do not endogenously express HNA-3a or HNA-3, such as B-cells, CHO cells or insect cells. The invention also contemplates using cells that express low levels of HNA-3a or HNA-3b and increasing expression of the endogenous HNA-3a or HNA-3b protein by inserting heterologous promoters or enhancers, or increasing copy number of the HNA-3a or HNA-3b gene.

Exemplary B cell that may be used in the methods of the invention include EB-3 cells (ATCC CCL85), K-562 cells (ATCC CCL243), RAJI cells (ATCC CCL86), Jiyoye cells (CCL87), IM-9 (ATCC159), Daudi cells (ATCC CCL213), NC-37 cells (ATCC 214), Mo-B cells (ATCC 245), KG-1 cells (ATCC CCL246), H2126 cells (ATCC 256), BL2126 cells (ATCC 256) and MCL-5 cells (ATCC CCL10575). Other exemplary cells that may be used in the methods of the invention include Chinese hamster ovary cells (CHO) (ATCC No. CCL61), CHO DHFR-cells (Urlaub et al., *Proc. Natl. Acad. Sci. USA,* 97:4216-4220 (1980)), human embryonic kidney (HEK) 293 or 293T cells (ATCC No. CRL1573), or 3T3 cells (ATCC No. CCL92), monkey COS-1 (ATCC No. CRL1650) and COS-7 cell (ATCC No. CRL1651), and CV-1 cells (ATCC No. CCL70). In addition, insect cells may be used in the methods of the invention such as SF-9 and H15 cells.

Furthermore, cells that endogenously express HNA-3a or HNA-3b at low or moderate levels may be modified to enhance or overexpress endogenous HNA-3a or HNA-3b. For example a promoter, enhancer element, or an exogenous transcription modulatory element is inserted in the genome of the intended cell in proximity and orientation sufficient to influence the transcription of DNA encoding the HNA-3a or HNA-3b polypeptide. The control element controls a portion of the DNA present in the host cell genome. Thus, the expression of the HNA-3a or HNA-3b polypeptide may be achieved not by transfection of DNA that encodes the HNA-3a or HNA-3b gene itself, but rather by the use of targeting DNA (containing regions of homology with the endogenous gene of interest) coupled with DNA regulatory segments that provide the endogenous gene sequence with recognizable signals for transcription.

The invention also provides for methods of detecting HNA-3a or HNA-3b specific antibodies within a biological sample by contacting a biological sample with an aptamer that mimics an HNA-3a or HNA-3b antigenic fragment or epitope. Aptamers are macromolecules comprising single stranded oligonucleotides that have a sequence-dependent three-dimensional shape that will bind a target protein with high affinity and specificity. The invention contemplates developing and using aptamers that have a sequence that mimics the HNA-3a or HNA-3b epitope and therefore binds to HNA-3a or HNA-3b specific antibodies. These aptamers may be used in any of the methods of the invention to detect the presence of HNA-3a or HNA-3b specific antibodies.

The aptamers of the invention may comprise single stranded RNA or DNA oligonucleotides ranging in size between 15 and 50 bases that are fused to a scaffold such as thioredoxin. The aptamers will mimic the physical or structural characteristics of the HNA-3a and HNA-3b peptides of the invention. The aptamers are generally derived from combinatorial libraries through an in vitro selection process known as Systematic Evolution of Ligands through Exponential enrichment (SELEX). Exemplary methods for identifying and synthesizing aptamers against HNA-3a or HNA-3b antibodies are presented in Lo, *Antibody Engineering: methods and protocols* Vol 248 of *Methods in Molecular Biology*, Humana Press 2004, Klussmann, *The Aptamer Handbook: functional oligonucleotides and their applications* Wiley-VCH, 2006, and Jayasena *Clin. Chem.* 45:168-1650, 1999. Any of the assays described herein may be used to confirm that the contemplated aptamers bind to HNA-3a or HNA-3b specific antibodies.

Furthermore, the invention provides for methods of detecting HNA-3a or HNA-3b specific antibodies using peptides that mimic the secondary or tertiary structure of the antigenic fragments of HNA-3a or HNA-3b, while differing in primary amino acid structure. The structural characteristics of these peptides cause the HNA-3a or HNA-3b antibodies to cross react with these peptides. These peptides may be identified using standard methods in the art such as phage display peptide libraries and combinatorial libraries.

Methods of Distinguishing HNA-3a or HNA-3b Specific Antibodies

Any of the techniques described herein to detect HNA-3a or HNA-3b specific antibodies in a biological sample also may be used to distinguish if a particular antibody specifically binds to HNA-3a or HNA-3b. The assays would be carried out with the full length polypeptide or peptides that comprise amino acid 154. In particular, the peptides used in these assays may retain any secondary or tertiary structure that will distinguish the HNA-3a and HNA-3b epitopes.

Furthermore, assays using cells or tissues known to express HNA-3a or HNA-3b may be used to identify and distinguish HNA-3a or HNA-3b specific antibodies. These assays would include cells transfected or transformed to express HNA-3a or HNA-3b.

Isolation of these HNA-3a or HNA-3b specific antibodies is useful for carrying out the methods of the invention. In addition, the kits of the invention may comprise isolated HNA-3a or HNA-3b specific antibodies.

Methods of Detecting HNA-3 Protein

The invention provides for methods of detecting HNA-3a or HNA-3b in a biological sample. The term "HNA-3a" refers to the full length sequence of SEQ ID NO: 1 or at least a fragment of the amino acid sequence of SEQ ID NO: 1. The term "HNA-3b" refers to the full length amino acid sequence of SEQ ID NO: 2 or is at least a fragment of the amino acid sequence of SEQ ID NO: 2. Antigenic fragments of HNA-3a or HNA-3b that comprise particular epitopes that generate specific antibodies are of interest. For example, regions of the amino acid sequence of SEQ ID NO: 1 or 2 that are exposed to the cell surface are more likely to comprise an epitope.

Exemplary antigenic fragments that may be used to generate HNA-3a specific antibodies include the amino acid sequence of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42. Exemplary antigenic fragments that may be used to generate HNA-3b specific antibodies include the amino acid sequence of SEQ ID NO: 19, SEQ ID NO: 20, SEQ ID NO: 21, SEQ ID NO: 22, SEQ ID NO: 23, SEQ ID NO: 24 and SEQ ID NO: 26.

The primary structure of CTL2 indicates the existence of multiple polymorphic regions in both the coding region and promoter region of the CTL2 gene. Polymorphisms in the CTL2 gene may provide polymorphic information for HNA-3a or HNA-3b. The differences within the promoter region may cause different transcription efficiency and thus influence the expression of the CTL2 polypeptide. The polymorphisms in the coding region can alter the CTL2 protein conformation and thus the different polymorphic CTL2 proteins become immunogenic to each other. For example, nucleotide 461 of HNA-3a/HNA-3b is polymorphic wherein the HNA-3a allele is a "G" that encodes an arginine at position 154 and the HNA-3b allele is an "A" and encodes a glutamine.

The human neutrophil antigen HNA-1 has polymorphic epitopes. HNA-1 has three alleles, HNA-1a, HNA-1b and HNA-1c, which are the result of polymorphisms within the FcγRIIIb gene. HNA-1a and HNA-1b differ by four amino acids. The HNA-1c differs from HNA-1b by a single nucleotide substitution (C-to-A) at nucleotide 266 that results in a change of alanine to aspartate at amino acid 78. As described above, the polymorphisms in the CTL2 gene may result in HNA-3 polymorphic epitopes similar to those observed for HNA-1.

However, the human neutrophil antigen HNA-2 has a monomorphic epitope, in which a portion of the population does not express HNA-2. HNA-2 has only one well-described allele, HNA-2a. HNA-2a deficiency is caused by a transcription defect which exists among 5-10% individuals. Those individuals may generate HNA-2a antibody when exposed to the HNA-2a antigen. Therefore, it is contemplated that HNA-3A or HNA-3b may have a monomorphic epitope similar to HNA-2.

The invention also contemplates detecting additional antigens, such as HNA-1, HNA-2, HNA-4, HNA-5 and/or HLA, in combination with detecting HNA-3a or HNA-3b in a biological sample.

Commercial antibodies that bind to human CTL2 may be used in the methods of the invention. Exemplary commercial antibodies include human monoclonal anti-SLC44A2 antibody (clone 3D11) and human anti-SLC44A2 polyclonal antibody both available from Sigma Aldrich (St. Louis, Mo.).

Additional exemplary antibodies include SLC44A2 antibody (ab57570) available from Abcam (Cambridge, Mass.), CTL2 monoclonal antibody (M01), clone 3D11 available from Abnova (Walnut, Calif.), Mouse Polyclonal anti-SLC44A2—solute carrier family 44, member 2, MaxPab Antibody and Mouse polyclonal anti-CTL2 available from Novus Biologicals (Littleton, Colo.).

The antibodies of the invention may be polyclonal antibodies, monoclonal antibodies, antibody fragments which retain their ability to bind their unique epitope (e.g., Fv, Fab and F(ab)2 fragments), single chain antibodies and human or humanized antibodies. Antibodies may be generated by techniques standard in the art using the HNA-3a or HNA-3b epitope on CTL2 or antigenic fragments of SEQ ID NO: 1 or SEQ ID NO: 2. Antibody molecules of the present invention include the classes of IgG (as well as subtypes IgG 1, IgG 2a, and IgG2b), IgM, IgA, IgD, and IgE.

The antibodies of the invention may be labeled for detection of binding within the biological sample. The antibodies may comprise a radioactive label such as $^3$H, $^{14}$C, $^{32}$P, $^{35}$S, or $^{125}$I. In addition, the labels may be a fluorescent or chemiluminescent compound, such as fluorescein isothiocyanate, phycoerythrin, rhodamine, or luciferin. The labels may be enzymes such as alkaline phosphatase, β-galactosidase, biotin and avidin or horseradish peroxidase (Bayer et al., *Meth. Enz.*, 184:138-163 (1990)).

The HNA-3a and HNA-3b specific antibodies may be attached to solid substrates such as membranes, beads, filters, glass, silicon, metal, metal-alloy, anopore, polymeric, nylon or plastic for detection of HNA-3a or HNA-3b in a biological sample.

Antigens of the invention may be a whole protein, a truncated protein, a fragment of a protein or a peptide. Antigens may be naturally occurring, genetically engineered variants of the protein, or may be codon optimized for expression in a particular mammalian subject or host. Generally, a B-cell epitope will include at least about 5 amino acids but can be as small as 3-4 amino acids.

Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature). Antibodies such as anti-idiotype antibodies, or fragments thereof, and synthetic peptide mimotopes, that are synthetic peptides which can mimic an antigen or antigenic determinant, are also captured under the definition of antigen as used herein.

Furthermore, for purposes of the present invention, an "antigen" refers to a protein, which includes modifications, such as deletions, additions and substitutions, generally conservative in nature, to the naturally occurring sequence, so long as the protein maintains the ability to elicit an immunological response, as defined herein. These modifications may be deliberate, as through site-directed mutagenesis, or may be accidental, as through mutations of hosts which produce the antigens. Antigens of the present invention may also be codon optimized by methods known in the art to improve their expression or immunogenicity in the host.

Specific binding of an antibody to an HNA-3a or HNA-3b antigen within a biological sample may be carried out using Western blot analysis with immunoblotting, immunocytochemistry, immunohistochemistry, dot blot analysis, flow cytometry, ELISA assays or RIA assays. These techniques and other approaches are conventional in the art (See Sambrook et al., Molecular Cloning: A Laboratory Manual, Cold Springs Harbor Laboratories (New York, 1989).

In addition, microcytotoxicity assays may be used to detect HNA-3a or HNA-3b in a biological sample. Microcytotoxicity assays involve the mixing of pure neutrophils derived from the recipient or donor with well characterized typing antibodies that are HNA-3a or HNA-3b immunoreactive. The mixture is incubated for a sufficient time to allow the antibodies to bind to the neutrophil surface HNA antigens. This is followed by addition of complement, which may be derived from, for example, rabbit serum. The addition of complement results in complement fixation and any cells with antibody bound to their cell surface will lyse due to the complement fixation reaction. The quantity of lysed cells can be measured using a variety of different methods. For example, a vital dye which is excluded from live cells but stains dead cells, such as trypan blue, can be added to the sample and the number of dead cells versus live cells can be determined.

Methods of Detecting HNA-3 Nucleic Acids

The invention provides for methods of detecting HNA-3a nucleic acids in a biological sample using oligonucleotide probes that hybridize to a fragment of the nucleic acid sequence of SEQ ID NO: 3. The invention provides for methods of detecting HNA-3b nucleic acids in a biological sample using oligonucleotide probes that hybridize to a fragment of the nucleic acid sequence of SEQ ID NO: 4. Hybridization of the HNA-3a or HNA-3b specific oligonucleotide probes may be detected using Northern Blot analysis, Southern Blot analysis, slot-blot analysis or in situ hybridization analysis or any other methods convention in the art, such as those techniques described in Sambrook et al., (Molecular Cloning: A Laboratory Manual, Cold Springs Harbor Laboratories (New York, 1989).

Preferred oligonucleotide probes are those which hybridize to sequences within the HNA-3a gene that encode the HNA-3a epitope. For example, preferred probes may hybridize to the nucleotides encoding the amino acid sequence of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 or SEQ ID NO: 42. In addition, the probes of the invention include those which hybridize to introns or 5' and 3' untranscribed regions of the gene encoding HNA-3a.

Preferred oligonucleotide probes are those which hybridize to sequences within the HNA-3b gene that encode the HNA-3b epitope. For example, preferred probes may hybridize to the nucleotides encoding the amino acid sequence SEQ ID NO: 19, SEQ ID NO: 20, SEQ ID NO: 21, SEQ ID NO: 22, SEQ ID NO: 23, SEQ ID NO: 24 or SEQ ID NO: 26. In addition, the probes of the invention include those which hybridize to introns or 5' and 3' untranscribed regions of the gene encoding HNA-3b.

The oligonucleotide probes may be labeled for detection of hybridization with the DNA extracted from the biological sample. The probes may comprise a radioactive label such as $^3$H, $^{14}$C, $^{32}$P, $^{35}$S, or $^{125}$I. In addition, the labels may be a fluorescent or chemiluminescent compound, such as fluorescein isothiocyanate, phycoerythrin, rhodamine, or luciferin. The labels may be enzymes such as alkaline phosphatase, β-galactosidase, biotin and avidin or horseradish peroxidase (Bayer et al., *Meth. Enz.*, 184:138-163 (1990)).

An array or microarray refers to a collection of DNA probes or DNA fragments attached to a solid surface, such as glass, plastic or silicon-chip, forming an array for the purpose of expression profiling or monitoring expression level of many genes simultaneously. Arrays of oligonucleotide probes may be used to detect the HNA-3a or HNA-3b DNA in a biological sample. Preferred arrays include probes that hybridize to HNA-1 and/or HNA-2. In addition, arrays that include probes that hybridize to HNA-1, HNA-2 and HLA are preferred. Commercial arrays may be used to detect HNA-3a or HNA-3b that include probes that hybridize to CTL2 such as Affymetrix probe sets nos. 58800, 48798 and 56340 which detect SLC44A2 on array nos. U95-C and U95-B, probe set nos. 225175 and 224609 which detect SLC44A2 on array no. U133-B, and probe set nos. 225175 and 224609 which detect SLC44A2 on array no. U133 Plus 2. The arrays of the invention include microarrays, DNA chips, bead arrays, gene chips and biochips.

The oligonucleotide probes may be attached to solid substrates such as membranes, beads, filters, glass, silicon, metal, metal-alloy, anopore, polymeric, nylon or plastic. The substrates may be chemically treated with chemical prior to attaching probes to enhance binding or to inhibit nonspecific binding during use. Exemplary treatments include coating glass slides with coating of aminoalkyl silanes or polymeric materials such as acrylamide or proteins. The probes may be covalently or non-covalently attached to the substrate.

The invention also provides for methods of detecting HNA-3a or HNA-3b in a biological sample using an amplification method such as polymerase chain reaction and at least one oligonucleotide primer specific for a fragment of the nucleic acid sequence encoding HNA-3a (SEQ ID NO: 1) or HNA-3b (SEQ ID NO: 2).

As used herein, "polymerase chain reaction" or "PCR" means a process such as described in U.S. Pat. No. 4,683,195 and U.S. Pat. No. 4,683,202 for the amplification of a segment of DNA using at least two primers and a DNA polymerase. Other nucleic acid amplification methods strand displacement assay 3(SDA, BD ProbeTec™, isothermal amplification methods such as helicase-dependent amplification (HDA) and isothermal reverse transcription-thermophilic helicase-dependent amplification (RT-tHDA), rolling circle amplification (RCA) and loop-mediated isothermal amplification (LAMP). These methods may be carried out using techniques standard in the art. The invention also contemplates using sequencing analysis to confirm the identity of DNA fragments amplified using PCR.

In the methods of the invention, PCR may be carried out using a "PCR reaction mixture" which is a mixture suitable for carrying out PCR. The PCR reaction mixture will contain a suitable amount of a thermostable DNA polymerase, a linear or circular template DNA, preferably double-stranded DNA, to be amplified, a pair of oligonucleotide primers such that one of the primers is configured for annealing to one strand of the template and the other primer is configured for annealing to the other or complementary strand of the template, ATP, suitable amounts of each of the four deoxyribonucleoside triphosphates (dNTPs), and buffers, salts such as $MgCl_2$, preservatives, reducing agents, and water as may be required.

The oligonucleotide primers of the invention will be designed to specifically amplify the nucleic acid encoding the HNA-3a epitope or the HNA-3b epitope. When designing the oligonucleotide primers, the length of a primer depends upon its (A+T) content, and the Tm of its partner. In addition, the primer should be complex enough to decrease the likelihood of the primer annealing to sequences other than the chosen target. The methods of the invention may utilize primers ranging in length from 10-30 nucleotides, preferably the primers will be 17 nucleotides in length. Generally, a 40%-60% G+C content is recommended for the primers, avoiding internal secondary structure and long stretches of any one base. In addition, primers should not anneal to regions of secondary structure (within the target) having a higher melting point than the primer.

Preferred oligonucleotide primers of the invention for genotyping HNA-3a phenotype include primers that amplify the nucleotides encoding amino acid sequence of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 or SEQ ID NO: 42. In addition, the primers of the invention include those which amplify fragments of SEQ ID NO: 3 that are within introns or the 5' and 3' untranscribed regions of the gene encoding HNA-3a. Exemplary primers include sense primer 5' AGT GGC TGA GCT TCG 3'(SEQ ID NO: 48) and antisense primer 5' GTG CGC CAA TAT CCT CAC TTG 3' (SEQ ID NO: 50).

Preferred oligonucleotide primers of the invention for genotyping HNA-3b phenotype include primers that amplify the nucleotides encoding amino acid sequence of SEQ ID NO: 19, SEQ ID NO: 20, SEQ ID NO: 21, SEQ ID NO: 22, SEQ ID NO: 23, SEQ ID NO: 24 or SEQ ID NO: 26. The invention also contemplates primers the amplify a fragment of SEQ ID NO: 4 that comprise codon 154 of SEQ ID NO: 4. In addition, the primers of the invention include those which amplify fragments of SEQ ID NO: 4 that are within introns or the 5' and 3' untranscribed regions of the gene encoding HNA-3b. Exemplary primers include sense primer 5' GAG TGG CTG TGC TTC A 3' (SEQ ID NO: 49) and antisense primer 5' GTG CGC CAA TAT CCT CAC TTG 3' (SEQ ID NO: 50).

The invention also contemplates methods of detecting HNA-1 nucleic acid in a biological sample in addition to detecting HNA-3 nucleic acid. HNA-1 nucleic acids may be detected using oligonucleotide probes or oligonucleotide primers that detect the unique HNA-1 epitopes (polymorphisms) at nucleotides 141, nucleotide 147, nucleotide 227, nucleotide 277 or nucleotide 349 (HNA-1a vs. HNA-1b) and nucleotide 266 (HNA-1c vs. HNA-1b). The invention further contemplates methods of detecting HNA-2 nucleic acid in a biological sample in addition to detecting HNA-3 nucleic acid. Since HNA-2 only has one allele, the expression of the HNA-2 can be detected with oligonucleotide probes or primers homologous to any coding region.

Deoxyribonucleoside triphosphates (dNTPs) include 2'-deoxyadenosine 5'-triphosphate (dATP), 2'-deoxycytidine 5'-triphosphate (dCTP), 2'-deoxyguanosine 5'-triphosphate (dGTP), and 2'-deoxythymidine 5'-triphosphate (dTTP). Generally, the concentration of dNTP in the PCR reaction is about 200 μM. It is important to keep the four dNTP concentrations above the estimated Km of each dNTP (10 μM-15 μM) and balanced for best base incorporation. Lowering the concentrations of dNTP and magnesium ion by an equal molar concentration can improve fidelity. Modified dNTPs (dig-11-dUTP, 5-bromo-dUTP, inosine, biotin-11-dUTP, biotin-16-dUTP and 7-deaza dGTP) and 2'-deoxyuridine 5'-triphosphate (dUTP) also may be used.

Kits

The invention provides for kits to carry out any of the methods of the invention. Kits according to the invention comprises components for detecting HNA-3a or HNA-3b specific antibodies in a biological sample. The kit can comprise an isolated or recombinant HNA-3a or HNA-3b polypeptide or an antigenic fragment thereof that forms a complex with HNA-3a or HNA-3b specific antibodies in a biological sample and a known HNA-3a or HNA-3b specific antibody for a positive control. The invention further provides for kits for detecting antibodies specific for HNA-1 and HNA-2 in addition to antibodies specific for HNA-3a or HNA-3b, which will contain Fc-γ receptor IIIb or antigenic fragments thereof for HNA-1 detection and CD177 or antigenic fragments thereof for detection of HNA-2 and known antibodies that are specific for HNA-1 and HNA-2. The invention further provides for kits for detecting antibodies specific for HNA-4 and/or HNA-5 in addition to antibodies specific for HNA-3a or HNA-3b, which will contain CD11b (CR3) or antigenic fragments thereof for HNA-4 detection and CD11a (LFA-1) or antigenic fragments thereof for detection of HNA-5 and known antibodies that are specific for HNA-4 and HNA-5. Furthermore, the invention provides for kits for detecting antibodies specific for HLA in a biological sample in addition to antibodies specific for HNA, which will contain polypeptides containing the HLA antigen and known antibodies that are specific for HLA.

Kits useful for detecting antibodies specific for HNA-3a or HNA-3b and optionally antibodies specific for other HNA and/or HLA antigens may further comprise any components necessary to carry out the detection assays that are conventional in the art. For example, the kits may comprise the components necessary to carry out SRID, ELISA, HAI, MAIGA assay, GIIFT, MLAT, and GAT.

Kits according to the invention comprises components for detecting HNA-3a or HNA-3b in a biological sample. The kit can comprise an antibody that specifically binds to HNA-3a or HNA-3b, and an isolated or recombinant protein or a peptide comprising the HNA-3a or HNA-3b epitope for the antibody to use as a positive control. The invention further provides for kits for detecting HNA-1 and HNA-2 in addition to HNA-3a or HNA-3b, which will contain antibodies specific for HNA-1 and/or HNA-2 and recombinant proteins or peptides corresponding to the HNA-1 and HNA-2 epitopes. Furthermore, the invention provides for kits for detecting HLA in a biological sample in addition to HNA, which will contain antibodies specific for HLA and recombinant protein or peptides that correspond to the HLA epitope.

Kits useful for detecting HNA-3a or HNA-3b and optionally other HNA and/or HLA antigens may further comprise any components necessary to carry out the detection assays that are conventional in the art. For example, the kits may comprise buffers, loading dyes, gels such as polyacrylamide gels and molecular weight markers preparing SDS-PAGE gels to carry out Western blots. The kits may also comprise filters, membranes blocking buffers, control buffers, isotype control antibodies, wash buffers or buffers and reagents for detection to carry out immunoblotting or dot blotting analysis such as labeled secondary antibodies. The kit may also comprise fixing reagents, blocking buffers, control buffers, wash buffers, staining dyes and detection reagents including anti-idiospecific antibodies to carry out immunocytochemistry or immunohistochemistry. Furthermore, the kits may comprise the necessary reagents and tools to carryout flow cytometry, ELISA assays, RIA assays or microtoxicity assays.

Kits according to the invention comprise components for detecting HNA-3a or HNA-3b nucleic acid in a biological sample. The kit will comprise oligonucleotide probes that hybridize to a fragment of HNA-3a nucleic acid of SEQ ID NO: 3 and a fragment of the nucleic acid of SEQ ID NO: 3 that hybridizes to the oligonucleotide probes to use as a positive control. Alternatively, the kit will comprise oligonucleotide probes that hybridize to a fragment of HNA-3b nucleic acid of SEQ ID NO: 4 and a fragment of the nucleic acid of SEQ ID NO: 4 that hybridizes to the oligonucleotide probes to use as a positive control. The invention further provides for kits to detect HNA-1 and HNA-2 nucleic acid, in addition to HNA-3a or HNA-3b nucleic acid in a biological sample, which will contain oligonucleotide probes that are specific for HNA-1 and HNA-2, and corresponding fragments of the HNA-1 and HNA-2 nucleic acids as positive controls. In addition, the invention provides for kits for detecting HLA nucleic acid in addition to HNA nucleic acid in a biological sample, which will contain oligonucleotide probes specific for HLA nucleic acid and corresponding fragments of HLA nucleic acid as positive controls.

Alternatively, the kits for detecting HNA-3a nucleic acids will comprise oligonucleotide primers for amplifying a fragment of the HNA-3a nucleic acid of SEQ ID NO: 3, and a fragment of the HNA-3a nucleic acid that is known to be amplified by the oligonucleotide primers to serve as a positive control. The kits for detecting HNA-3b nucleic acids will comprise oligonucleotide primers for amplifying a fragment of the HNA-3b nucleic acid of SEQ ID NO: 4, and a fragment of the HNA-3b nucleic acid that is known to be amplified by the oligonucleotide primers to serve as a positive control. The invention further provides for kits that comprise oligonucleotide primers specific for HNA-1 and HNA-2 nucleic acids, and the fragments of the nucleic acids of HNA-1 and HNA-2 that are known to be amplified by the oligonucleotide primers. In addition, the invention provides for kits containing oligonucleotide primers specific for HLA nucleic acid in addition to oligonucleotide primers specific for HNA nucleic acids and a fragment of the HLA nucleic acid that is amplified by the oligonucleotide primers.

The kits of the invention may also comprise the components necessary to carry out PCR or other amplification methods. For example, the kit may contain one or more of the following: Taq polymerase or another thermostable polymerase, ATP, suitable amounts of each of the four deoxyribonucleoside triphosphates (dNTPs), and buffers, salts such as $MgCl_2$, preservatives, reducing agents or water.

Kits useful for detecting HNA-3a or HNA-3b nucleic acids and optionally other HNA and/or HLA nucleic acids may further comprise any components necessary to carry out the detection assays that are conventional in the art. For example, the kits may comprise the reagents necessary for extracting the nucleic acids from the biological sample. The kits may comprise buffers, loading dyes, gels, molecular weight markers, membranes, filters, blocking buffers and detection reagents for Northern Blot analysis, Southern Blot analysis, slot-blot analysis or in situ hybridization analysis and any other methods convention in the art, such as those techniques.

The present invention is illustrated by the following examples that are not intended to limit the invention. Example 1 describes isolation of granulocytes from donor blood. Example 2 described the method used to obtain HNA-3a positive and negative plasma. Example 3 describes biotinylation of granulocyte surface proteins. Example 4 describes a method of incubating granulocytes with plasma. Example 5 describes fluorescence activated cell sorting using flow cytometry. Example 6 describes a method of carrying out immunoprecipitation using magnetic beads. Example 7 describes a method of carrying out SDS-PAGE and Western blotting. Example 8 describes a method of using Fourier transform ion cyclotron resonance mass spectrometry (FTICR-MS). The experiments described in Examples 1-8 were used to identify the amino acid sequences of HNA-3a and HNA-3b, and these methods may be used to carry out the methods of the invention. Example 9 describes the heterologous expression of HNA-3a and HNA-3b, and these polypeptides may be used in the methods of the invention. Example 10 describes heterologous expression of HNA-3a peptide fragments, and these peptide fragments were used to map the epitope of HNA-3a, and these peptides may be used in the methods of the invention. Example 11 describes affinity purification of HNA-3a antibodies from human blood plasma. Example 12 described identification of antigenic fragments of HNA-3a, and these fragments may be used to carry out the methods of the invention. Example 13 describes a method of genotyping for HNA-3a and HNA-3b, which may be used to carry out the methods of the invention. Lastly, Example 14 describes methods of making anti-HNA-3 antibodies, and these antibodies may be used to carry out the methods of the invention.

EXAMPLES

Example 1

Granulocyte Isolation

Selected donor blood was mixed with 1.25% EDTA and 0.5% dextran. After sedimentation, the supernatant was further used for Ficoll density centrifugation. After washing of the obtained pellet, a haemolysis of the erythrocytes took place. Remaining granulocytes were washed and served in various cell concentrations as starting material.

Example 2

Obtaining HNA-3a Positive and Negative Plasma

Selected donor blood was mixed with 1.25% EDTA, then the cells were separated by centrifugation. The supernatant served as corresponding plasma.

Example 3

Biotinylation of Granulocyte Surface Proteins

For the analysis by Western blots, the purified granulocytes were biotinylated using the EZ-Link Sulfo-NHS-LC-LC-biotin (PIERCE; Rockford, Ill.).

Example 4

Incubation of the Granulocytes with Plasma

Granulocytes (biotinylated or non-biotinylated) were incubated with HNA-3a-positive or -negative plasma for at least 30 minutes at 37° C. After washing the batch, either a FACS analysis of whole cells took place, or the cell lysis by means of buffer containing Triton-X100 was carried out. After centrifuging off the cell debris, the supernatant containing protein was analyzed.

Example 5

Fluorescence Activated Cell Sorting (FACS Analysis) Flow Cytometry

Isolated granulocytes of HNA-3a-positive and -negative donors were incubated with plasma (with and without anti-HNA-3a antibodies) and washed. Subsequently, the cells were incubated with fluorescein isothiocyanate (FITC) labeled rabbit F(ab')2-anti-human IgG. After washing, the cell suspension was examined with FACS to determine for the fluorescence intensity of the granulocytes. High intensities pointed to HNA-3a-positive results.

Example 6

Immunoprecipitation by Means of Magnetic Beads

Protein-G coated magnetic beads were coupled with anti-human IgG (Fc specific). After washing, the beads were incubated with the supernatant containing protein, as described in Example 4. After renewed washing and demagnetizing of the beads, the proteins were eluted using sample buffer containing SDS, (for analysis via SDS-PAGE and Western blot) or digested directly in buffer containing trypsin (for analysis via Fourier transform ion cyclotron resonance mass spectrometry (FTICR-MS)).

Example 7

SDS-PAGE/Western Blot

The eluent of the immunoprecipitation (biotinylated batches) was separated by SDS-PAGE (7.5% separation gels) and blotted on nitrocellulose membrane. For coupling to the biotinylated proteins, the membrane, after blocking and washing steps, was incubated with alkaline phosphatase (AP) bonded to streptavidin. The detection took place by the addition of NBT (Nitro-Blue Tetrazolium Chloride)/BCIP (5-Bromo-4-Chloro-3'-Indolyphosphate p-Toluidine Salt) for 1-15 minutes.

Example 8

Fourier Transform Ion Cyclotron Resonance (FTICR-MS)

The tryptic digestion of the immunoprecipitated proteins (not biotinylated batches) was pre-cleaned using C18 material (ZipTip) and analyzed by MS. The evaluation of the peptide spectra took place by data bank comparisons using of SEQUEST Sorcerer- and Scaffold2 software (Data bank: uniprot-sprot-human_rel54).

Example 9

Heterologous Expression of HNA-3a and HNA-3b

A cDNA clone having a DNA sequence encoding the HNA-3a protein (SEQ ID NO: 1) was expressed in *E. coli* and in CHO cells. The synthesized protein was separated with SDS-PAGE gel electrophoresis (as described in Example 7) and the specificity was shown by binding of human anti-HNA-3a antibodies in Western blot. An analogous procedure was carried out for a cDNA clone with the DNA sequence for the expression of the protein HNA-3b (SEQ ID NO: 2).

The HNA-3a protein was expressed with a His-tag to allow for purification. In addition, solid phase ELISA was used to demonstrate binding of the recombinant human anti-HNA-3a or HNA-3b protein with its respective antibody.

Example 10

Heterologous Expression of Peptide Fragments

HNA-3a DNA fragments were cloned using the pGEX-2TK vector (GE Healthcare, Chalfont St Giles, UK) and the restriction enzymes BamHI and HindIII (Roche, Basel, Switzerland). The cDNA clone NM_020428.2 (OriGene, Rockville, Md.) was used as template DNA to generate Glutathione S-Transferase gene region (GST) fusions. DNA fragments encoding amino acids 22-231 of SEQ ID NO: 1 (denoted as "HNA-3a(22-231)"), and amino acids 145-167 of SEQ ID NO: 1 (denoted as "HNA-3a(145-167)") were inserted into the vector JHC27 to encode GST-HNA-3a fusion peptides. DNA fragments encoding amino acids 114-164 of SEQ ID NO: 1 (denoted as "HNA-3a(114-164)") were inserted into the pTB25 vector to encode the GST fusion peptide GST-HNA-3a(114-164).

*E. coli* BL21-Gold(DE3) cells (Stratagene, La Jolla, Calif.) were transformed with the above described vectors and grown at 37 C in YTG medium containing 100 µg/ml ampicillin to an OD600=0.7. Subsequently, the cells were incubated with Isopropyl β-D-1-thiogalactopyranoside (IPTG) (1 mM; 1 h), followed by centrifugation (7,000 g; 10 min) and washing in ice-cold PBS. The cells were then sonicated in denaturing buffer (8 M Urea), centrifuged (12,000 g) and the supernatant was dialyzed against denaturing-buffer (Tris-glycerin). The fusion protein supernatants were loaded onto a glutathione sepharose column and washed with PBS. A solution of 50 mM Tris-HCl (pH 8) containing 10 mM reduced glutathione was used for elution of the GST-HNA-3a fusion peptides.

Example 11

Affinity Purification of HNA-3a Antibodies from Human Blood Plasma

For affinity purification of HNA-3a antibodies from human blood plasma, GST-HNA-3a(114-164) was produced as described in Example 10), concentrated and dialyzed against coupling buffer (0.2 M NaHCO$_3$, 0.5 M NaCl, pH 8.3). A HiTrap NHS-activated HP column (GE Healthcare, Uppsala, Sweden) was equilibrated with 6 ml ice-cold 1 mM HCl; and subsequently, 1 ml of the concentrated GST-HNA-3a(114-164) peptide was injected (3 mg/ml) onto the column. After 30 minutes incubation at 25° C., the column was washed according to manufacturer's instructions.

Human plasma known to be positive for HNA-3a antibodies was diluted in wash buffer (1:25) (20 mM NaH2PO4, 150 mM NaCl, pH 7.4) and 50 ml was loaded onto the column at a flow rate of 0.8 ml/min. After washing with washing buffer, the antibodies were eluted from the column using 10 ml 0.1 M glycine buffer (pH 2.7). Aliquots of the collected fractions (750 µl) were mixed with 250 µl neutralization buffer (1 M Tris-HCl, pH 9). Fractions containing a protein concentration greater than 50 µg/ml were pooled and dialyzed against wash buffer.

A Granulocyte Activation Assay was used to test whether HNA-3a induced granulocyte aggregation. Granulocytes isolated from HNA-3a positive donors (as described in Example 1) were incubated with human plasma (30 min, 37° C.) known to contain anti-HNA-3a antibodies, and subsequently washed (140 g, 5 min). Bound antibodies were obtained using system for acid elution according to the manufacturer's instructions (BAG, Lich, Germany).

The HNA-3a specific antibodies, of the eluted antibodies obtained by affinity purification in combination with the GST-HNA-3a(114-164) peptide in the Granulocyte Activation Assay. The negative controls for this assay were the GST-fusion protein alone, a control serum containing HNA-3b antibodies and a negative control antibody (no HNA-3 antibodies). HNA-3a antibodies activated granulocytes to aggregation only in its native form and had little effect in denatured formed. Fixed granulocyte agglutinates were not positive.

Example 12

Identification of Antigenic Fragments of HNA-3a

In order to map the epitope of the HNA-3a amino acids sequence (SEQ ID NO: 1), recombinant peptides comprising extracellular fragments of the HNA-3a amino acid sequence were generated as GST-fusion peptides as described in Example 10. Reactivity of these peptides with HNA-3a sera as determined by Western blot is provided in Table 1 below

| SEQ ID NO: | Amino acids of HNA-3a (SEQ ID NO: 1) | Reactivity with HNA-3a |
|---|---|---|
| 27 | 55-231 | ++ |
| 14 | 55-183 | ++ |
| 28 | 55-105 | -- |
| 29 | 105-153 | -- |
| 30 | 155-200 | -- |
| 31 | 190-231 | -- |
| 32 | 150-159 | -- |
| 33 | 144-167 | (+) |
| 34 | 134-174 | ++ |
| 35 | 124-183 | ++ |
| 36 | 114-194 | ++ |
| 37 | 105-200 | ++ |
| 38 | 94-214 | ++ |
| 39 | 84-220 | ++ |
| 40 | 44-164 | ++ |
| 41 | 75-164 | ++ |
| 42 | 94-164 | ++ |
| 16 | 114-164 | ++ |
| 43 | 134-164 | (+) |
| 44 | 142-183 | -- |
| 45 | 142-200 | -- |
| 46 | 142-222 | -- |
| 47 | 142-231 | -- |

Isolated granulocytes from a representative HNA-3a positive (HNA-3a+) donor and a representative HNA-3a negative donor (HNA-3a−) were incubated with plasma known to contain HNA-3a antibodies (+) and with plasma known to be free of HNA-3a antibody (−). HNA-3a protein was then immunoprecipitated using anti-human IgG, coupled with Protein G coupled magnetic beads. For each donor/plasma combination was a sample was deglycosylated with Peptide-N-Glycosidase F (PNGase F).

The immunoprecipitated proteins were separated by SDS-PAGE and transferred to nitrocellulose using procedures well known in the art, and analyzed by immunoblotting with a HNA-3a+ and HNA-3a− plasma. The proteins were initially visualized using alkaline phosphatase conjugated to streptavidin (a) or anti-human IgG (b) and then incubated with NBT/BCIP for detection.

The GST-fusion peptides comprising amino acids 145-167 of SEQ ID NO: 1 (HNA-3a(145-167); SEQ ID NO: 48) and amino acids 55-231 of SEQ ID NO: 1 (HNA-3a(55-231); SEQ ID NO: 27) were analyzed using an immunoblot. A 50 kDa band represents the GST-HNA-3a(55-231) peptide bound to an antibody present in HNA-3a positive sera. A smaller band of 36 kDa represents the GST-HNA-3a(145-167) peptide bound to an antibody present in HNA-3a positive sera. Only antibodies from HNA-3+ plasma reacted with the HNA-3a fusion peptides. Antibodies from the HNA-3a− plasma did not react with the HNA-3a fusion proteins. The binding to the longer HNA-3a amino acids 55-231 peptide is shown for two HNA-3a positive plasmas and the binding for the smaller fragment HNA-3a amino acids 145-167 is displayed for HNA-3a positive plasma.

The GST-fusion peptide HNA-3a amino acids 145-167 also induced aggregation in HNA-3a positive granulocytes.

This analysis demonstrated that the critical minimum antigenic fragment of the HNA-3a polypeptide sequence is amino acids 154-164 of SEQ ID NO: 1 (SEQ ID NO: 25).

This method may be used to identify the antigenic fragments of HNA-3a or any other antigen such as HNA-1, HNA-2, HNA-5 or HLA.

Example 13

Genotyping for HNA-3a and HNA-3b

PCR for HNA-3 polymorphisms were carried out as follows. Aliquots of 50-100 ng DNA were amplified using 0.5 pmol allele-specific sense primers (5'-AGT GGC TGA GGT GCT TCG-3; SEQ ID NO: 49; HNA-3a) or 5'-GAG TGG CTG AGG TGC TTC A-3'; SEQ ID NO: 50; HNA-3b)) and a partial intronic antisense primer (5'-GTG CGC CAA TAT CCT CAC TTG-3'(SEQ ID NO: 51)). Polymerase chain reaction (PCR) was performed with 0.2 mmol deoxyribonucleotide triphosphate and 2.0 units Hot Start Taq DNA Polymerase (GeneCraft, Germany) on a Thermal Cycler (GeneAmp PCR System 2700, Applied Biosystems, Germany) in a total volume of 20 μL. After heating at 95° C. for 10 minutes, 2-step PCR was performed under the following conditions: denaturing (30 seconds, 95° C.), annealing (40 seconds, 64° C.), extension (30 seconds, 72° C.) for 10 cycles, denaturing (30 seconds, 95° C.), annealing (30 seconds, 61° C.), extension (30 seconds, 72° C.) for 20 cycles, and final extension (5 minutes, 72° C.). As internal positive control, 0.0625 pmol human growth hormone (hGH) primers amplifying a 439-bp fragment of the hGH gene were used (5'-CAG TGC CTT CCC AAC CAT TCC CTT A-3' (SEQ ID NO: 52), 5'-ATC CAC TCA CGG ATT TCT GTT GTG TTT C-3' (SEQ ID NO: 53)). PCR products (291 bp) were analysed on 1.5% agarose gels using Tris borate EDTA buffer (TBE-buffer; 5 Prime, Germany).

This method may be used to genotype for any antigen allele such as HNA-1, HNA-2, HNA-4, HNA-5 or HLA.

Example 14

Methods of Making Anti-HNA-3 Antibodies

Antibodies specific for HNA-3a or HNA-3b protein may be obtained by immunization with peptide comprising a particular HNA-3 epitope. Suitable procedures for generating antibodies include those described in Hudson and Hay, Practical Immunology, 2nd Edition, Blackwell Scientific Publications (1980). Exemplary antigenic fragments that may be used to generate HNA-3a specific antibodies include SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42. Exemplary antigenic fragments that may be used to generate HNA-3b specific antibodies include SEQ ID NO: 19, SEQ ID NO: 20, SEQ ID NO: 21, SEQ ID NO: 22, SEQ ID NO: 23, SEQ ID NO: 24 and SEQ ID NO: 26.

In one procedure for the production of antibodies, animals (typically mice or rabbits) are injected with a HNA-3a or HNA-3b epitope containing peptide and the resulting polyclonal antibodies in the serum are isolated. In addition, those animals with sufficient serum titer levels as determined by ELISA are selected for hybridoma production. Spleens of immunized animals are collected and prepared as single cell suspensions from which splenocytes are recovered. The splenocytes are fused to mouse myeloma cells (such as Sp2/0-Ag14 cells; ATCC no. CRL-1581), allowed to incubate in DMEM with 200 U/ml penicillin, 200 g/ml streptomycin sulfate, and 4 mM glutamine, and then incubated in HAT selection medium (Hypoxanthine; Aminopterin; Thymidine). After selection, the tissue culture supernatants are taken from each well containing a hybridoma and tested for anti-HNA-3a or HNA-3b antibody production by ELISA.

Alternative procedures for obtaining anti-HNA-3a or anti-HNA-3b antibodies may also be employed, such as the immunization of transgenic mice harboring human Ig loci for the production of human antibodies, and the screening of synthetic antibody libraries, such as those generated by mutagenesis of an antibody variable domain.

Furthermore, human antibodies can be produced from phage-display libraries (Hoogenboom et al., *J. Mol. Biol.* 227:381 (1991); Marks et al., *J. Mol. Biol.* 222:581 (1991). These processes mimic immune selection through the display of antibody repertoires on the surface of filamentous bacteriophage, and subsequent selection of phage by their binding to an antigen of choice. One such technique is described in PCT Application no. PCT/US98/17364, which describes the isolation of high affinity and functional agonistic antibodies for MPL- and msk-receptors using such an approach.

These methods are used to generate antibodies specific for any antigenic protein such as HNA-1, HNA-2, HNA-4, HNA-5 or HLA.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A method of determining whether a donor tissue intended for transplant or transfusion will induce transfusion related acute lung injury (TRALI) or graft versus host disease (GVHD) in a human recipient wherein the human recipient expresses the HNA-3a antigen comprising the amino acid sequence of SEQ ID: 1 or antigenic fragment thereof, the method comprising
   a) obtaining a sample from the donor of the tissue intended for transplant or transfusion in the human subject, wherein the sample is blood, blood derivative, plasma or serum,
   b) contacting the sample with a polypeptide comprising the amino acid sequence of SEQ ID NO: 1 or an antigenic fragment thereof to form a complex with HNA-3a specific antibodies in the sample, and
   c) detecting the complex, wherein the presence of the complex indicates that the donor tissue is likely to induce TRALI or GVHD in a human recipient that expresses the HNA-3a antigen.

2. The method of claim 1 wherein the antigenic fragment comprises an amino acid sequence selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO:32, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

3. The method of claim 1 further comprising one or more of the steps of
   d) contacting the sample with Fc-γ receptor IIIb polypeptide comprising the amino acid sequence of SEQ ID: 6 or an antigenic fragment thereof to form a complex with HNA-1 specific antibodies in the sample,
   e) contacting the sample with CD177 polypeptide comprising the amino acid sequence of SEQ ID: 8 or an antigenic fragment thereof to form a complex with HNA-2 specific antibodies in the sample,
   f) contacting the sample with CD11b polypeptide comprising the amino acid sequence of SEQ ID:10 or an antigenic fragment thereof to form a complex with HNA-4 specific antibodies in the sample,
   g) contacting the sample with CD11a polypeptide comprising the amino acid sequence of SEQ ID: 12 or an antigenic fragment thereof to form a complex with HNA-5 specific antibodies in the sample, or h) contacting the sample with an HLA antigen to form a complex with HLA specific antibodies in the sample, and i) detecting the complex, wherein the presence of any of the complexes indicates that the sample is likely to induce TRALI or GVHD in a human recipient.

4. A method of determining the susceptibility of a human transplant or transfusion recipient for rejecting transplanted or transfused tissue, wherein the donor tissue contains HNA-3a polypeptide comprising the amino acid sequence of SEQ ID:1 or an antigenic fragment thereof, comprising a) obtaining a biological sample from the human transplant or transfusion recipient prior to transplantation or transfusion, wherein the sample is blood, blood derivative, plasma or serum, b) contacting the biological sample with polypeptide comprising the amino acid sequence of SEQ ID NO: 1 or an antigenic fragment thereof to form a complex with HNA-3a specific antibodies in the biological sample, and c) detecting the complex, wherein the presence of the complex in the biological sample indicates that the human transplant or transfusion recipient is susceptible for rejecting the transplanted or transfused tissue.

5. The method of claim 4 wherein the antigenic fragment comprises an amino acid sequence selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 25, SEQ ID NO: 27, SEQ ID NO:32, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 and SEQ ID NO: 42.

6. The method of claim 1, wherein the antibody comprises a label selected from the group consisting of a radioactive label, fluorescent label, enzymatic label, avidin label or biotin label.

7. The method of claim 1, wherein the complex is detected with a secondary antibody.

8. The method of claim 7, wherein the secondary antibody comprises a label selected from the group consisting of a radioactive label, fluorescent label, enzymatic label, avidin label or biotin label.

9. The method of claim 4, wherein the antibody comprises a label selected from the group consisting of a radioactive label, fluorescent label, enzymatic label, avidin label or biotin label.

10. The method of claim 4, wherein the complex is detected with a secondary antibody.

11. The method of claim 10, wherein the secondary antibody comprises a label selected from the group consisting of a radioactive label, fluorescent label, enzymatic label, avidin label or biotin label.

12. The method of claim 2 further comprising one or more of the steps of d) contacting the sample with Fc-y receptor IIIb polypeptide comprising the amino acid sequence of SEQ ID NO:6 or an antigenic fragment thereof to form a complex with HNA-1 specific antibodies in the sample, e) contacting the sample with CD 177 polypeptide comprising the amino acid sequence of SEQ ID NO:8 or an antigenic fragment thereof to form a complex with HNA-2 specific antibodies in the sample;

f) contacting the sample with CD11b polypeptide comprising the amino acid sequence of SEQ ID NO:10 or an antigenic fragment thereof to form a complex with HNA-4 specific antibodies in the sample;

g) contacting the sample with CD11a polypeptide comprising the amino acid sequence of SEQ ID NO:12 or an antigenic fragment thereof to form a complex with HNA-5 specific antibodies in the sample, or h) contacting the sample with an HLA antigen to form a complex with HLA specific antibodies in the sample, and i) detecting the complex, wherein the presence of any of the complexes indicates that the sample is likely to induce TRALI or GVHD in a human recipient.

13. The method of claim 4 further comprising one or more of the steps of d) contacting the sample with Fc-y receptor IIIb polypeptide comprising the amino acid sequence of SEQ ID NO:6 or an antigenic fragment thereof to form a complex with HNA-1 specific antibodies in the sample, e) contacting the sample with CD 177 polypeptide comprising the amino acid sequence of SEQ ID NO:8 or an antigenic fragment thereof to form a complex with HNA-2 specific antibodies in the sample;

f) contacting the sample with CD11b polypeptide comprising the amino acid sequence of SEQ ID NO:10 or an antigenic fragment thereof to form a complex with HNA-4 specific antibodies in the sample;

g) contacting the sample with CD11a polypeptide comprising the amino acid sequence of SEQ ID NO:12 or an antigenic fragment thereof to form a complex with HNA-5 specific antibodies in the sample, or h) contacting the sample with an HLA antigen to form a complex with HLA specific antibodies in the sample, and i) detecting the complex, wherein the presence of any of the complexes in the biological sample indicates that that the human transplant or transfusion recipient is susceptible for developing rejecting the transplanted or transfused tissue, wherein the donor tissue contains any of HNA-1, HNA-2, HNA-3a, HNA4, HNA-5 and HLA.

14. The method of claim 5 further comprising one or more of the steps of d) contacting the sample with Fc-y receptor IIIb polypeptide comprising the amino acid sequence of SEQ ID NO:6 or an antigenic fragment thereof to form a complex with HNA-1 specific antibodies in the sample, e) contacting the sample with CD 177 polypeptide comprising the amino acid sequence of SEQ ID NO:8 or an antigenic fragment thereof to form a complex with HNA-2 specific antibodies in the sample;

f) contacting the sample with CD11b polypeptide comprising the amino acid sequence of SEQ ID NO:10 or an antigenic fragment thereof to form a complex with HNA-4 specific antibodies in the sample;

g) contacting the sample with CD11a polypeptide comprising the amino acid sequence of SEQ ID NO:12 or an antigenic fragment thereof to form a complex with HNA-5 specific antibodies in the sample, or h) contacting the sample with an HLA antigen to form a complex with HLA specific antibodies in the sample, and i) detecting the complex, wherein the presence of any of the complexes in the biological sample indicates that that the human transplant or transfusion recipient is susceptible for developing rejecting the transplanted or transfused tissue, wherein the donor tissue contains any of HNA-1, HNA-2, HNA-3a, HNA4, HNA-5 and HLA.

* * * * *

UNITED STATES PATENT AND TRADEMARK OFFICE
CERTIFICATE OF CORRECTION

| | | |
|---|---|---|
| PATENT NO. | : 8,084,216 B2 | Page 1 of 1 |
| APPLICATION NO. | : 12/553487 | |
| DATED | : December 27, 2011 | |
| INVENTOR(S) | : Greinacher et al. | |

It is certified that error appears in the above-identified patent and that said Letters Patent is hereby corrected as shown below:

<u>On the Title Page:</u>
Item [74], under "Attorney, Agent, or Firm", at Column 2, Lines 1-2,
"Marshall, Gerstein & Bourn LLP" should be -- Marshall, Gerstein & Borun LLP --.

<u>In the Claims:</u>
Column 113, Line 55, in Claim 12, "Fc-y" should be -- Fc-$\gamma$ --.

Column 114, Line 13, in Claim 13, "Fc-y" should be -- Fc-$\gamma$ --.

Column 114, Line 33, in Claim 13, "that that" should be -- that --.

Column 114, Line 37, in Claim 13, "HNA4," should be -- HNA-4, --.

Column 114, Line 40, in Claim 14, "Fc-y" should be -- Fc-$\gamma$ --.

Column 114, Line 60, in Claim 14, "that that" should be -- that --.

Column 114, Line 64, in Claim 14, "HNA4," should bet -- HNA-4, --.

Signed and Sealed this
Ninth Day of September, 2014

Michelle K. Lee
*Deputy Director of the United States Patent and Trademark Office*